US010856987B2

(12) United States Patent
Cabiri et al.

(10) Patent No.: US 10,856,987 B2
(45) Date of Patent: *Dec. 8, 2020

(54) MULTIPLE ANCHOR DELIVERY TOOL

(71) Applicant: Valtech Cardio, Ltd., Or Yehuda (IL)

(72) Inventors: Oz Cabiri, Hod Hasharon (IL); Amir Gross, Tel Aviv-Jaffa (IL); Tal Hammer, Ramat Gan (IL); Tal Reich, Moledet (IL); Ehud Iflah, Tel Aviv-Jaffa (IL)

(73) Assignee: Valtech Cardio, Ltd., Or Yehuda (IL)

( * ) Notice: Subject to any disclaimer, the term of this patent is extended or adjusted under 35 U.S.C. 154(b) by 299 days.

This patent is subject to a terminal disclaimer.

(21) Appl. No.: 15/948,140

(22) Filed: Apr. 9, 2018

(65) Prior Publication Data

US 2018/0256333 A1 Sep. 13, 2018
US 2019/0269513 A9 Sep. 5, 2019

Related U.S. Application Data

(63) Continuation of application No. 14/837,783, filed on Aug. 27, 2015, now Pat. No. 9,937,042, which is a
(Continued)

(51) Int. Cl.
*A61F 2/24* (2006.01)
*A61B 17/064* (2006.01)
(Continued)

(52) U.S. Cl.
CPC ...... *A61F 2/2466* (2013.01); *A61B 17/00234* (2013.01); *A61B 17/064* (2013.01);
(Continued)

(58) Field of Classification Search
CPC .... A61F 2/2442; A61F 2/2445; A61F 2/2448; A61F 2/2451; A61F 2/2466;
(Continued)

(56) References Cited

U.S. PATENT DOCUMENTS 3,604,488 A 9/1971 Wishart et al.
3,656,185 A 4/1972 Carpentier
(Continued)

FOREIGN PATENT DOCUMENTS

EP 0611561 A1 8/1994
EP 1034753 A1 9/2000
(Continued)

OTHER PUBLICATIONS

Agarwal et al. International Cardiology Perspective Functional Tricuspid Regurgitation, Circ Cardiovasc Interv 2009;2;2;565-573 (2009).
(Continued)

*Primary Examiner* — Robert A Lynch
(74) *Attorney, Agent, or Firm* — Thomas C. Richardson

(57) ABSTRACT

Anchor deployment systems and tools are provided. An anchor deployment tool can include a flexible tube including a distal anchor manipulation portion. The tool can also include a deployment element, which is positionable within the flexible tube, and is configured to, while the distal anchor manipulation portion is proximate an implantable device, (i) engage the anchors in the flexible tube, (ii) advance each of the anchors in a distal direction to the distal anchor manipulation portion, and (iii) anchor the implantable device to tissue of a subject by deploying each of the tissue anchors through the implantable device and into the tissue.

18 Claims, 30 Drawing Sheets

Related U.S. Application Data continuation of application No. 13/749,153, filed on Jan. 24, 2013, now Pat. No. 9,119,719, which is a continuation-in-part of application No. PCT/IL2011/000600, filed on Jul. 26, 2011, which is a continuation-in-part of application No. 12/843,412, filed on Jul. 26, 2010, now Pat. No. 8,523,881, which is a continuation-in-part of application No. 12/437,103, filed on May 7, 2009, now Pat. No. 8,715,342.

(51) Int. Cl.
*A61B 17/068* (2006.01)
*A61B 17/00* (2006.01)

(52) U.S. Cl.
CPC .......... *A61B 17/068* (2013.01); *A61F 2/2442* (2013.01); *A61F 2/2445* (2013.01); *A61B 2017/00243* (2013.01); *A61B 2017/0647* (2013.01); *A61B 2017/0649* (2013.01); *A61F 2220/0016* (2013.01)

(58) Field of Classification Search
CPC ..... A61F 2220/0008; A61F 2220/0016; A61B 17/00234; A61B 17/064; A61B 17/068; A61B 2017/00243; A61B 2017/0647; A61B 2017/0649; A61B 2017/07207
See application file for complete search history.

(56) References Cited

U.S. PATENT DOCUMENTS

| | | |
|---|---|---|
| 3,840,018 A | 10/1974 | Heifetz |
| 3,881,366 A | 5/1975 | Bradley et al. |
| 3,898,701 A | 8/1975 | La Russa |
| 4,042,979 A | 8/1977 | Angell |
| 4,118,805 A | 10/1978 | Reimels |
| 4,214,349 A | 7/1980 | Munch |
| 4,261,342 A | 4/1981 | Aranguren Duo |
| 4,290,151 A | 9/1981 | Massana |
| 4,434,828 A | 3/1984 | Trincia |
| 4,473,928 A | 10/1984 | Johnson |
| 4,602,911 A | 7/1986 | Ahmadi et al. |
| 4,625,727 A | 12/1986 | Leiboff |
| 4,712,549 A | 12/1987 | Peters et al. |
| 4,778,468 A | 10/1988 | Hunt et al. |
| 4,917,698 A | 4/1990 | Carpentier et al. |
| 4,935,027 A | 6/1990 | Yoon |
| 4,961,738 A | 10/1990 | Mackin |
| 5,042,707 A | 8/1991 | Taheri |
| 5,061,277 A | 10/1991 | Carpentier et al. |
| 5,064,431 A | 11/1991 | Gilbertson et al. |
| 5,104,407 A | 4/1992 | Lam et al. |
| 5,108,420 A | 4/1992 | Marks |
| 5,201,880 A | 4/1993 | Wright et al. |
| 5,258,008 A | 11/1993 | Wilk |
| 5,300,034 A | 4/1994 | Behnke et al. |
| 5,306,296 A | 4/1994 | Wright et al. |
| 5,325,845 A | 7/1994 | Adair |
| 5,346,498 A | 9/1994 | Greelis et al. |
| 5,383,852 A | 1/1995 | Stevens-Wright |
| 5,449,368 A | 9/1995 | Kuzmak |
| 5,450,860 A | 9/1995 | O'Connor |
| 5,464,404 A | 11/1995 | Abela et al. |
| 5,474,518 A | 12/1995 | Farrer Velazquez |
| 5,477,856 A | 12/1995 | Lundquist |
| 5,593,424 A | 1/1997 | Northrup, III |
| 5,601,572 A | 2/1997 | Middleman et al. |
| 5,626,609 A | 5/1997 | Zvenyatsky et al. |
| 5,643,317 A | 7/1997 | Pavcnik et al. |
| 5,669,919 A | 9/1997 | Sanders et al. |
| 5,674,279 A | 10/1997 | Wright et al. |
| 5,676,653 A | 10/1997 | Taylor et al. |
| 5,683,402 A | 11/1997 | Cosgrove et al. |
| 5,702,397 A | 12/1997 | Goble et al. |
| 5,702,398 A | 12/1997 | Tarabishy |
| 5,709,695 A | 1/1998 | Northrup, III |
| 5,716,370 A | 2/1998 | Williamson, IV et al. |
| 5,716,397 A | 2/1998 | Myers |
| 5,728,116 A | 3/1998 | Rosenman |
| 5,730,150 A | 3/1998 | Peppel et al. |
| 5,749,371 A | 5/1998 | Zadini et al. |
| 5,782,844 A | 7/1998 | Yoon et al. |
| 5,810,882 A | 9/1998 | Bolduc et al. |
| 5,824,066 A | 10/1998 | Gross |
| 5,830,221 A | 11/1998 | Stein et al. |
| 5,843,120 A | 12/1998 | Israel et al. |
| 5,855,614 A | 1/1999 | Stevens et al. |
| 5,876,373 A | 3/1999 | Giba et al. |
| 5,935,098 A | 8/1999 | Blaisdell et al. |
| 5,957,953 A | 9/1999 | DiPoto et al. |
| 5,961,440 A | 10/1999 | Schweich, Jr. et al. |
| 5,961,539 A | 10/1999 | Northrup, III et al. |
| 5,984,959 A | 11/1999 | Robertson et al. |
| 6,042,554 A | 3/2000 | Rosenman et al. |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,074,341 A | 6/2000 | Anderson et al. |
| 6,074,401 A | 6/2000 | Gardiner et al. |
| 6,074,417 A | 6/2000 | Peredo |
| 6,086,582 A | 7/2000 | Altman et al. |
| 6,102,945 A | 8/2000 | Campbell |
| 6,106,550 A | 8/2000 | Magovern et al. |
| 6,110,200 A | 8/2000 | Hinnenkamp |
| 6,132,390 A | 10/2000 | Cookston et al. |
| 6,143,024 A | 11/2000 | Campbell et al. |
| 6,159,240 A | 12/2000 | Sparer et al. |
| 6,165,119 A | 12/2000 | Schweich, Jr. et al. |
| 6,174,332 B1 | 1/2001 | Loch et al. |
| 6,183,411 B1 | 2/2001 | Mortier et al. |
| 6,187,040 B1 | 2/2001 | Wright |
| 6,210,347 B1 | 4/2001 | Forsell |
| 6,217,610 B1 | 4/2001 | Carpentier et al. |
| 6,231,602 B1 | 5/2001 | Carpentier et al. |
| 6,251,092 B1 | 6/2001 | Qin et al. |
| 6,296,656 B1 | 10/2001 | Bolduc et al. |
| 6,315,784 B1 | 11/2001 | Djurovic |
| 6,319,281 B1 | 11/2001 | Patel |
| 6,328,746 B1 | 12/2001 | Gambale |
| 6,332,893 B1 | 12/2001 | Mortier et al. |
| 6,355,030 B1 | 3/2002 | Aldrich et al. |
| 6,361,559 B1 | 3/2002 | Houser et al. |
| 6,368,348 B1 | 4/2002 | Gabbay |
| 6,402,780 B2 | 6/2002 | Williamson, IV et al. |
| 6,406,420 B1 | 6/2002 | McCarthy et al. |
| 6,406,493 B1 | 6/2002 | Tu et al. |
| 6,419,696 B1 | 7/2002 | Ortiz et al. |
| 6,451,054 B1 | 9/2002 | Stevens |
| 6,458,076 B1 | 10/2002 | Pruitt |
| 6,461,336 B1 | 10/2002 | Larre |
| 6,461,366 B1 | 10/2002 | Seguin |
| 6,470,892 B1 | 10/2002 | Forsell |
| 6,503,274 B1 | 1/2003 | Howanec, Jr. et al. |
| 6,524,338 B1 | 2/2003 | Gundry |
| 6,527,780 B1 | 3/2003 | Wallace et al. |
| 6,530,952 B2 | 3/2003 | Vesely |
| 6,533,772 B1 | 3/2003 | Sherts et al. |
| 6,537,314 B2 | 3/2003 | Langberg et al. |
| 6,547,801 B1 | 4/2003 | Dargent et al. |
| 6,554,845 B1 | 4/2003 | Fleenor et al. |
| 6,564,805 B2 | 5/2003 | Garrison et al. |
| 6,565,603 B2 | 5/2003 | Cox |
| 6,569,198 B1 | 5/2003 | Wilson et al. |
| 6,579,297 B2 | 6/2003 | Bicek et al. |
| 6,589,160 B2 | 7/2003 | Schweich, Jr. et al. |
| 6,592,593 B1 | 7/2003 | Parodi et al. |
| 6,602,288 B1 | 8/2003 | Cosgrove et al. |
| 6,602,289 B1 | 8/2003 | Colvin et al. |
| 6,613,078 B1 | 9/2003 | Barone |
| 6,613,079 B1 | 9/2003 | Wolinsky et al. |
| 6,619,291 B2 | 9/2003 | Hlavka et al. |
| 6,626,899 B2 | 9/2003 | Houser et al. |
| 6,626,917 B1 | 9/2003 | Craig |

(56) References Cited

U.S. PATENT DOCUMENTS

| | | |
|---|---|---|
| 6,626,930 B1 | 9/2003 | Allen et al. |
| 6,629,534 B1 | 10/2003 | St. Goar et al. |
| 6,629,921 B1 | 10/2003 | Schweich, Jr. et al. |
| 6,651,671 B1 | 11/2003 | Donlon et al. |
| 6,652,556 B1 | 11/2003 | VanTassel et al. |
| 6,682,558 B2 | 1/2004 | Tu et al. |
| 6,689,125 B1 | 2/2004 | Keith et al. |
| 6,689,164 B1 | 2/2004 | Seguin |
| 6,695,866 B1 | 2/2004 | Kuehn et al. |
| 6,702,826 B2 | 3/2004 | Liddicoat et al. |
| 6,702,846 B2 | 3/2004 | Mikus et al. |
| 6,706,065 B2 | 3/2004 | Langberg et al. |
| 6,709,385 B2 | 3/2004 | Forsell |
| 6,709,456 B2 | 3/2004 | Langberg et al. |
| 6,711,444 B2 | 3/2004 | Koblish |
| 6,719,786 B2 | 4/2004 | Ryan et al. |
| 6,723,038 B1 | 4/2004 | Schroeder et al. |
| 6,726,716 B2 | 4/2004 | Marquez |
| 6,726,717 B2 | 4/2004 | Alfieri et al. |
| 6,730,121 B2 | 5/2004 | Ortiz et al. |
| 6,749,630 B2 | 6/2004 | McCarthy et al. |
| 6,752,813 B2 | 6/2004 | Goldfarb et al. |
| 6,764,310 B1 | 7/2004 | Ichihashi et al. |
| 6,764,510 B2 | 7/2004 | Vidlund et al. |
| 6,764,810 B2 | 7/2004 | Ma et al. |
| 6,770,083 B2 | 8/2004 | Seguin |
| 6,786,924 B2 | 9/2004 | Ryan et al. |
| 6,786,925 B1 | 9/2004 | Schoon et al. |
| 6,790,231 B2 | 9/2004 | Liddicoat et al. |
| 6,797,001 B2 | 9/2004 | Mathis et al. |
| 6,797,002 B2 | 9/2004 | Spence et al. |
| 6,802,319 B2 | 10/2004 | Stevens et al. |
| 6,805,710 B2 | 10/2004 | Bolling et al. |
| 6,805,711 B2 | 10/2004 | Quijano et al. |
| 6,855,126 B2 | 2/2005 | Flinchbaugh |
| 6,858,039 B2 | 2/2005 | McCarthy |
| 6,884,250 B2 | 4/2005 | Monassevitch et al. |
| 6,893,459 B1 | 5/2005 | Macoviak |
| 6,908,478 B2 | 6/2005 | Alferness et al. |
| 6,908,482 B2 | 6/2005 | McCarthy et al. |
| 6,918,917 B1 | 7/2005 | Nguyen et al. |
| 6,926,730 B1 | 8/2005 | Nguyen et al. |
| 6,960,217 B2 | 11/2005 | Bolduc |
| 6,964,684 B2 | 11/2005 | Ortiz et al. |
| 6,964,686 B2 | 11/2005 | Gordon |
| 6,976,995 B2 | 12/2005 | Mathis et al. |
| 6,986,775 B2 | 1/2006 | Morales et al. |
| 6,989,028 B2 | 1/2006 | Lashinski et al. |
| 6,997,951 B2 | 2/2006 | Solem et al. |
| 7,004,176 B2 | 2/2006 | Lau |
| 7,007,798 B2 | 3/2006 | Happonen et al. |
| 7,011,669 B2 | 3/2006 | Kimblad |
| 7,011,682 B2 | 3/2006 | Lashinski et al. |
| 7,018,406 B2 | 3/2006 | Seguin et al. |
| 7,037,334 B1 | 5/2006 | Hlavka et al. |
| 7,077,850 B2 | 7/2006 | Kortenbach |
| 7,077,862 B2 | 7/2006 | Vidlund et al. |
| 7,087,064 B1 | 8/2006 | Hyde |
| 7,101,395 B2 | 9/2006 | Tremulis et al. |
| 7,101,396 B2 | 9/2006 | Artof et al. |
| 7,112,207 B2 | 9/2006 | Allen et al. |
| 7,118,595 B2 | 10/2006 | Ryan et al. |
| 7,125,421 B2 | 10/2006 | Tremulis et al. |
| 7,150,737 B2 | 12/2006 | Purdy et al. |
| 7,159,593 B2 | 1/2007 | McCarthy et al. |
| 7,166,127 B2 | 1/2007 | Spence et al. |
| 7,169,187 B2 | 1/2007 | Datta et al. |
| 7,172,625 B2 | 2/2007 | Shu et al. |
| 7,175,660 B2 | 2/2007 | Cartledge et al. |
| 7,186,262 B2 | 3/2007 | Saadat |
| 7,186,264 B2 | 3/2007 | Liddicoat et al. |
| 7,189,199 B2 | 3/2007 | McCarthy et al. |
| 7,192,443 B2 | 3/2007 | Solem et al. |
| 7,220,277 B2 | 5/2007 | Arru et al. |
| 7,226,467 B2 | 6/2007 | Lucatero et al. |
| 7,226,477 B2 | 6/2007 | Cox |
| 7,226,647 B2 | 6/2007 | Kasperchik et al. |
| 7,229,452 B2 | 6/2007 | Kayan |
| 7,238,191 B2 | 7/2007 | Bachmann |
| 7,288,097 B2 | 10/2007 | Seguin |
| 7,294,148 B2 | 11/2007 | McCarthy |
| 7,311,728 B2 | 12/2007 | Solem et al. |
| 7,311,729 B2 | 12/2007 | Mathis et al. |
| 7,314,485 B2 | 1/2008 | Mathis |
| 7,316,710 B1 | 1/2008 | Cheng et al. |
| 7,329,279 B2 | 2/2008 | Haug et al. |
| 7,329,280 B2 | 2/2008 | Bolling et al. |
| 7,335,213 B1 | 2/2008 | Hyde et al. |
| 7,361,190 B2 | 4/2008 | Shaoulian et al. |
| 7,364,588 B2 | 4/2008 | Mathis et al. |
| 7,377,941 B2 | 5/2008 | Rhee et al. |
| 7,390,329 B2 | 6/2008 | Westra et al. |
| 7,404,824 B1 | 7/2008 | Webler et al. |
| 7,431,692 B2 | 10/2008 | Zollinger et al. |
| 7,442,207 B2 | 10/2008 | Rafiee |
| 7,452,376 B2 | 11/2008 | Lim et al. |
| 7,455,690 B2 | 11/2008 | Cartledge et al. |
| 7,485,142 B2 | 2/2009 | Milo |
| 7,485,143 B2 | 2/2009 | Webler et al. |
| 7,500,989 B2 | 3/2009 | Solem et al. |
| 7,507,252 B2 | 3/2009 | Lashinski et al. |
| 7,510,575 B2 | 3/2009 | Spenser et al. |
| 7,510,577 B2 | 3/2009 | Moaddeb et al. |
| 7,527,647 B2 | 5/2009 | Spence |
| 7,530,995 B2 | 5/2009 | Quijano et al. |
| 7,549,983 B2 | 6/2009 | Roue et al. |
| 7,559,936 B2 | 7/2009 | Levine |
| 7,562,660 B2 | 7/2009 | Saadat |
| 7,563,267 B2 | 7/2009 | Goldfarb et al. |
| 7,563,273 B2 | 7/2009 | Goldfarb et al. |
| 7,569,062 B1 | 8/2009 | Kuehn et al. |
| 7,585,321 B2 | 9/2009 | Cribier |
| 7,588,582 B2 | 9/2009 | Starksen et al. |
| 7,591,826 B2 | 9/2009 | Alferness et al. |
| 7,604,646 B2 | 10/2009 | Goldfarb et al. |
| 7,608,091 B2 | 10/2009 | Goldfarb et al. |
| 7,608,103 B2 | 10/2009 | McCarthy |
| 7,625,403 B2 | 12/2009 | Krivoruchko |
| 7,632,303 B1 | 12/2009 | Stalker et al. |
| 7,635,329 B2 | 12/2009 | Goldfarb et al. |
| 7,635,386 B1 | 12/2009 | Gammie |
| 7,655,015 B2 | 2/2010 | Goldfarb et al. |
| 7,666,204 B2 | 2/2010 | Thornton et al. |
| 7,682,319 B2 | 3/2010 | Martin et al. |
| 7,682,369 B2 | 3/2010 | Seguin |
| 7,686,822 B2 | 3/2010 | Shayani |
| 7,699,892 B2 | 4/2010 | Rafiee et al. |
| 7,704,269 B2 | 4/2010 | St. Goar et al. |
| 7,704,277 B2 | 4/2010 | Zakay et al. |
| 7,722,666 B2 | 5/2010 | Lafontaine |
| 7,736,388 B2 | 6/2010 | Goldfarb et al. |
| 7,748,389 B2 | 7/2010 | Salahieh et al. |
| 7,753,924 B2 | 7/2010 | Starksen et al. |
| 7,758,632 B2 | 7/2010 | Hojeibane et al. |
| 7,780,726 B2 | 8/2010 | Seguin |
| 7,871,368 B2 | 1/2011 | Zollinger et al. |
| 7,871,433 B2 | 1/2011 | Lattouf |
| 7,883,475 B2 | 2/2011 | Dupont et al. |
| 7,883,538 B2 | 2/2011 | To et al. |
| 7,892,281 B2 | 2/2011 | Seguin et al. |
| 7,927,370 B2 | 4/2011 | Webler et al. |
| 7,927,371 B2 | 4/2011 | Navia et al. |
| 7,942,927 B2 | 5/2011 | Kaye et al. |
| 7,947,056 B2 | 5/2011 | Griego et al. |
| 7,955,315 B2 | 6/2011 | Feinberg et al. |
| 7,955,377 B2 | 6/2011 | Melsheimer |
| 7,992,567 B2 | 8/2011 | Hirotsuka et al. |
| 7,993,368 B2 | 8/2011 | Gambale et al. |
| 7,993,397 B2 | 8/2011 | Lashinski et al. |
| 8,012,201 B2 | 9/2011 | Lashinski et al. |
| 8,034,103 B2 | 10/2011 | Burriesci et al. |
| 8,052,592 B2 | 11/2011 | Goldfarb et al. |
| 8,057,493 B2 | 11/2011 | Goldfarb et al. |
| 8,062,355 B2 | 11/2011 | Figulla et al. |

(56) References Cited

U.S. PATENT DOCUMENTS

| | | |
|---|---|---|
| 8,070,804 B2 | 12/2011 | Hyde et al. |
| 8,070,805 B2 | 12/2011 | Vidlund et al. |
| 8,075,616 B2 | 12/2011 | Solem et al. |
| 8,100,964 B2 | 1/2012 | Spence |
| 8,123,801 B2 | 2/2012 | Milo |
| 8,142,493 B2 | 3/2012 | Spence et al. |
| 8,142,495 B2 | 3/2012 | Hasenkam et al. |
| 8,142,496 B2 | 3/2012 | Berreklouw |
| 8,147,542 B2 | 4/2012 | Maisano et al. |
| 8,152,844 B2 | 4/2012 | Rao et al. |
| 8,163,013 B2 | 4/2012 | Machold et al. |
| 8,187,299 B2 | 5/2012 | Goldfarb et al. |
| 8,187,324 B2 | 5/2012 | Webler et al. |
| 8,202,315 B2 | 6/2012 | Hlavka et al. |
| 8,206,439 B2 | 6/2012 | Gomez Duran |
| 8,216,302 B2 | 7/2012 | Wilson et al. |
| 8,231,671 B2 | 7/2012 | Kim |
| 8,262,725 B2 | 9/2012 | Subramanian |
| 8,265,758 B2 | 9/2012 | Policker et al. |
| 8,277,502 B2 | 10/2012 | Miller et al. |
| 8,287,584 B2 | 10/2012 | Salahieh et al. |
| 8,287,591 B2 | 10/2012 | Keidar et al. |
| 8,292,884 B2 | 10/2012 | Levine et al. |
| 8,303,608 B2 | 11/2012 | Goldfarb et al. |
| 8,323,334 B2 | 12/2012 | Deem et al. |
| 8,328,868 B2 | 12/2012 | Paul et al. |
| 8,333,777 B2 | 12/2012 | Schaller et al. |
| 8,343,173 B2 | 1/2013 | Starksen et al. |
| 8,343,174 B2 | 1/2013 | Goldfarb et al. |
| 8,343,213 B2 | 1/2013 | Salahieh et al. |
| 8,349,002 B2 | 1/2013 | Milo |
| 8,353,956 B2 | 1/2013 | Miller et al. |
| 8,357,195 B2 | 1/2013 | Kuehn |
| 8,382,829 B1 | 2/2013 | Call et al. |
| 8,388,680 B2 | 3/2013 | Starksen et al. |
| 8,393,517 B2 | 3/2013 | Milo |
| 8,419,825 B2 | 4/2013 | Burgler et al. |
| 8,430,926 B2 | 4/2013 | Kirson |
| 8,449,573 B2 | 5/2013 | Chu |
| 8,449,599 B2 | 5/2013 | Chau et al. |
| 8,454,686 B2 | 6/2013 | Alkhatib |
| 8,460,370 B2 | 6/2013 | Zakay |
| 8,460,371 B2 | 6/2013 | Hlavka et al. |
| 8,475,491 B2 | 7/2013 | Milo |
| 8,475,525 B2 | 7/2013 | Maisano et al. |
| 8,480,732 B2 | 7/2013 | Subramanian |
| 8,518,107 B2 | 8/2013 | Tsukashima et al. |
| 8,523,940 B2 | 9/2013 | Richardson et al. |
| 8,551,161 B2 | 10/2013 | Dolan |
| 8,585,755 B2 | 11/2013 | Chau et al. |
| 8,591,576 B2 | 11/2013 | Hasenkam et al. |
| 8,608,797 B2 | 12/2013 | Gross et al. |
| 8,628,569 B2 | 1/2014 | Benichou et al. |
| 8,628,571 B1 | 1/2014 | Hacohen et al. |
| 8,641,727 B2 | 2/2014 | Starksen et al. |
| 8,652,202 B2 | 2/2014 | Alon et al. |
| 8,652,203 B2 | 2/2014 | Quadri et al. |
| 8,679,174 B2 | 3/2014 | Ottma et al. |
| 8,685,086 B2 | 4/2014 | Navia et al. |
| 8,715,342 B2 | 5/2014 | Zipory et al. |
| 8,728,097 B1 | 5/2014 | Sugimoto et al. |
| 8,728,155 B2 | 5/2014 | Montorfano et al. |
| 8,734,467 B2 | 5/2014 | Miller et al. |
| 8,734,699 B2 | 5/2014 | Heideman et al. |
| 8,740,920 B2 | 6/2014 | Goldfarb et al. |
| 8,747,463 B2 | 6/2014 | Fogarty et al. |
| 8,778,021 B2 | 7/2014 | Cartledge |
| 8,784,481 B2 | 7/2014 | Alkhatib et al. |
| 8,790,367 B2 | 7/2014 | Nguyen et al. |
| 8,790,394 B2 | 7/2014 | Miller et al. |
| 8,795,298 B2 | 8/2014 | Hernlund et al. |
| 8,795,355 B2 | 8/2014 | Alkhatib |
| 8,795,356 B2 | 8/2014 | Quadri et al. |
| 8,795,357 B2 | 8/2014 | Yohanan et al. |
| 8,808,366 B2 | 8/2014 | Braido et al. |
| 8,808,368 B2 | 8/2014 | Maisano et al. |
| 8,845,717 B2 | 9/2014 | Khairkhahan et al. |
| 8,845,723 B2 | 9/2014 | Spence et al. |
| 8,852,261 B2 | 10/2014 | White |
| 8,852,272 B2 | 10/2014 | Gross et al. |
| 8,858,623 B2 | 10/2014 | Miller et al. |
| 8,864,822 B2 | 10/2014 | Spence et al. |
| 8,870,948 B1 | 10/2014 | Erzberger et al. |
| 8,870,949 B2 | 10/2014 | Rowe |
| 8,888,843 B2 | 11/2014 | Khairkhahan et al. |
| 8,889,861 B2 | 11/2014 | Skead et al. |
| 8,894,702 B2 | 11/2014 | Quadri et al. |
| 8,911,461 B2 | 12/2014 | Traynor et al. |
| 8,911,494 B2 | 12/2014 | Hammer et al. |
| 8,926,696 B2 | 1/2015 | Cabiri et al. |
| 8,926,697 B2 | 1/2015 | Gross et al. |
| 8,932,343 B2 | 1/2015 | Alkhatib et al. |
| 8,932,348 B2 | 1/2015 | Solem et al. |
| 8,940,044 B2 | 1/2015 | Hammer et al. |
| 8,945,211 B2 | 2/2015 | Sugimoto |
| 8,951,285 B2 | 2/2015 | Sugimoto et al. |
| 8,951,286 B2 | 2/2015 | Sugimoto et al. |
| 8,961,595 B2 | 2/2015 | Alkhatib |
| 8,961,602 B2 | 2/2015 | Kovach et al. |
| 8,979,922 B2 | 3/2015 | Jayasinghe et al. |
| 8,992,604 B2 | 3/2015 | Gross et al. |
| 9,005,273 B2 | 4/2015 | Salahieh et al. |
| 9,011,520 B2 | 4/2015 | Miller et al. |
| 9,011,530 B2 | 4/2015 | Reich et al. |
| 9,017,399 B2 | 4/2015 | Gross et al. |
| 9,023,100 B2 | 5/2015 | Quadri et al. |
| 9,072,603 B2 | 7/2015 | Tuval et al. |
| 9,107,749 B2 | 8/2015 | Bobo et al. |
| 9,119,719 B2 | 9/2015 | Zipory et al. |
| 9,125,632 B2 | 9/2015 | Loulmet et al. |
| 9,125,742 B2 | 9/2015 | Yoganathan et al. |
| 9,138,316 B2 | 9/2015 | Bielefeld |
| 9,173,646 B2 | 11/2015 | Fabro |
| 9,180,005 B1 | 11/2015 | Lashinski et al. |
| 9,180,007 B2 | 11/2015 | Reich et al. |
| 9,192,472 B2 | 11/2015 | Gross et al. |
| 9,198,756 B2 | 12/2015 | Aklog et al. |
| 9,226,825 B2 | 1/2016 | Starksen et al. |
| 9,265,608 B2 | 2/2016 | Miller et al. |
| 9,326,857 B2 | 5/2016 | Cartledge et al. |
| 9,414,921 B2 | 8/2016 | Miller et al. |
| 9,427,316 B2 | 8/2016 | Schweich, Jr. et al. |
| 9,474,606 B2 | 10/2016 | Zipory et al. |
| 9,526,613 B2 | 12/2016 | Gross et al. |
| 9,561,104 B2 | 2/2017 | Miller et al. |
| 9,579,090 B1 | 2/2017 | Simms et al. |
| 9,693,865 B2 | 7/2017 | Gilmore et al. |
| 9,730,793 B2 | 8/2017 | Reich et al. |
| 9,788,941 B2 | 10/2017 | Hacohen |
| 9,801,720 B2 | 10/2017 | Gilmore et al. |
| 9,907,547 B2 | 3/2018 | Gilmore et al. |
| 10,368,852 B2 | 8/2019 | Gerhardt et al. |
| 2001/0021874 A1 | 9/2001 | Carpentier et al. |
| 2002/0022862 A1 | 2/2002 | Grafton et al. |
| 2002/0082525 A1 | 6/2002 | Oslund et al. |
| 2002/0087048 A1 | 7/2002 | Brock et al. |
| 2002/0103532 A1 | 8/2002 | Langberg et al. |
| 2002/0120292 A1 | 8/2002 | Morgan |
| 2002/0133180 A1 | 9/2002 | Ryan et al. |
| 2002/0151916 A1 | 10/2002 | Muramatsu et al. |
| 2002/0151970 A1 | 10/2002 | Garrison et al. |
| 2002/0169358 A1 | 11/2002 | Mortier et al. |
| 2002/0177904 A1 | 11/2002 | Huxel et al. |
| 2002/0188301 A1 | 12/2002 | Dallara et al. |
| 2002/0188350 A1 | 12/2002 | Arru et al. |
| 2002/0198586 A1 | 12/2002 | Inoue |
| 2003/0050693 A1 | 3/2003 | Quijano et al. |
| 2003/0078465 A1 | 4/2003 | Pai et al. |
| 2003/0078653 A1 | 4/2003 | Vesely et al. |
| 2003/0105519 A1 | 6/2003 | Fasol et al. |
| 2003/0114901 A1 | 6/2003 | Loeb et al. |
| 2003/0120340 A1 | 6/2003 | Liska et al. |
| 2003/0144657 A1 | 7/2003 | Bowe et al. |
| 2003/0171760 A1 | 9/2003 | Gambale |

(56) References Cited

U.S. PATENT DOCUMENTS

| | | |
|---|---|---|
| 2003/0199974 A1 | 10/2003 | Lee et al. |
| 2003/0204193 A1 | 10/2003 | Gabriel et al. |
| 2003/0204195 A1 | 10/2003 | Keane et al. |
| 2003/0229350 A1 | 12/2003 | Kay |
| 2003/0229395 A1 | 12/2003 | Cox |
| 2004/0010287 A1 | 1/2004 | Bonutti |
| 2004/0019359 A1 | 1/2004 | Worley et al. |
| 2004/0019377 A1 | 1/2004 | Taylor et al. |
| 2004/0024451 A1 | 2/2004 | Johnson et al. |
| 2004/0039442 A1 | 2/2004 | St. Goar et al. |
| 2004/0044350 A1 | 3/2004 | Martin et al. |
| 2004/0059413 A1 | 3/2004 | Argento |
| 2004/0068273 A1 | 4/2004 | Fariss et al. |
| 2004/0111095 A1 | 6/2004 | Gordon et al. |
| 2004/0122514 A1 | 6/2004 | Fogarty et al. |
| 2004/0127982 A1 | 7/2004 | Machold et al. |
| 2004/0133274 A1 | 7/2004 | Webler et al. |
| 2004/0133374 A1 | 7/2004 | Kattan |
| 2004/0138744 A1 | 7/2004 | Lashinski et al. |
| 2004/0138745 A1 | 7/2004 | Macoviak et al. |
| 2004/0148019 A1 | 7/2004 | Vidlund et al. |
| 2004/0148020 A1 | 7/2004 | Vidlund et al. |
| 2004/0148021 A1 | 7/2004 | Cartledge et al. |
| 2004/0176788 A1 | 9/2004 | Opolski |
| 2004/0181287 A1 | 9/2004 | Gellman |
| 2004/0186566 A1 | 9/2004 | Hindrichs et al. |
| 2004/0193191 A1 | 9/2004 | Starksen et al. |
| 2004/0243227 A1 | 12/2004 | Starksen et al. |
| 2004/0260317 A1 | 12/2004 | Bloom et al. |
| 2004/0260344 A1 | 12/2004 | Lyons et al. |
| 2004/0260393 A1 | 12/2004 | Randert et al. |
| 2004/0260394 A1 | 12/2004 | Douk et al. |
| 2004/0267358 A1 | 12/2004 | Reitan |
| 2005/0004668 A1 | 1/2005 | Aklog et al. |
| 2005/0010287 A1 | 1/2005 | Macoviak et al. |
| 2005/0010787 A1 | 1/2005 | Tarbouriech |
| 2005/0016560 A1 | 1/2005 | Voughlohn |
| 2005/0049692 A1 | 3/2005 | Numamoto et al. |
| 2005/0055038 A1 | 3/2005 | Kelleher et al. |
| 2005/0055087 A1 | 3/2005 | Starksen |
| 2005/0060030 A1 | 3/2005 | Lashinski et al. |
| 2005/0065601 A1 | 3/2005 | Lee et al. |
| 2005/0070999 A1 | 3/2005 | Spence |
| 2005/0075727 A1 | 4/2005 | Wheatley |
| 2005/0085903 A1 | 4/2005 | Lau |
| 2005/0090827 A1 | 4/2005 | Gedebou |
| 2005/0090834 A1 | 4/2005 | Chiang et al. |
| 2005/0096740 A1 | 5/2005 | Langberg et al. |
| 2005/0107871 A1 | 5/2005 | Realyvasquez et al. |
| 2005/0119734 A1 | 6/2005 | Spence et al. |
| 2005/0125002 A1 | 6/2005 | Baran et al. |
| 2005/0125011 A1 | 6/2005 | Spence et al. |
| 2005/0131533 A1 | 6/2005 | Alfieri et al. |
| 2005/0137686 A1 | 6/2005 | Salahieh et al. |
| 2005/0137688 A1 | 6/2005 | Salahieh et al. |
| 2005/0137695 A1 | 6/2005 | Salahieh et al. |
| 2005/0159728 A1 | 7/2005 | Armour et al. |
| 2005/0171601 A1 | 8/2005 | Cosgrove et al. |
| 2005/0177180 A1 | 8/2005 | Kaganov et al. |
| 2005/0177228 A1 | 8/2005 | Solem et al. |
| 2005/0187568 A1 | 8/2005 | Klenk et al. |
| 2005/0192596 A1 | 9/2005 | Jugenheimer et al. |
| 2005/0203549 A1 | 9/2005 | Realyvasquez |
| 2005/0203606 A1 | 9/2005 | VanCamp |
| 2005/0216039 A1 | 9/2005 | Lederman |
| 2005/0216079 A1 | 9/2005 | MaCoviak |
| 2005/0222665 A1 | 10/2005 | Aranyi |
| 2005/0256532 A1 | 11/2005 | Nayak et al. |
| 2005/0267478 A1* | 12/2005 | Corradi ................. A61L 31/06 606/916 |
| 2005/0273138 A1 | 12/2005 | To et al. |
| 2005/0288778 A1 | 12/2005 | Shaoulian et al. |
| 2006/0004442 A1 | 1/2006 | Spenser et al. |
| 2006/0004443 A1 | 1/2006 | Liddicoat et al. |
| 2006/0020326 A9 | 1/2006 | Bolduc et al. |
| 2006/0020327 A1 | 1/2006 | Lashinski et al. |
| 2006/0020333 A1 | 1/2006 | Lashinski et al. |
| 2006/0020336 A1 | 1/2006 | Liddicoat |
| 2006/0025787 A1 | 2/2006 | Morales et al. |
| 2006/0025858 A1 | 2/2006 | Alameddine |
| 2006/0030885 A1 | 2/2006 | Hyde |
| 2006/0041319 A1 | 2/2006 | Taylor et al. |
| 2006/0069429 A1 | 3/2006 | Spence et al. |
| 2006/0074486 A1 | 4/2006 | Liddicoat et al. |
| 2006/0085012 A1 | 4/2006 | Dolan |
| 2006/0095009 A1 | 5/2006 | Lampropoulos et al. |
| 2006/0106423 A1 | 5/2006 | Weisel et al. |
| 2006/0116757 A1 | 6/2006 | Lashinski et al. |
| 2006/0122633 A1 | 6/2006 | To et al. |
| 2006/0129166 A1 | 6/2006 | Lavelle |
| 2006/0142694 A1 | 6/2006 | Bednarek et al. |
| 2006/0149280 A1 | 7/2006 | Harvie et al. |
| 2006/0149368 A1 | 7/2006 | Spence |
| 2006/0161265 A1 | 7/2006 | Levine et al. |
| 2006/0184240 A1 | 8/2006 | Jimenez et al. |
| 2006/0184242 A1 | 8/2006 | Lichtenstein |
| 2006/0195134 A1 | 8/2006 | Crittenden |
| 2006/0206203 A1 | 9/2006 | Yang et al. |
| 2006/0241622 A1 | 10/2006 | Zergiebel |
| 2006/0241656 A1 | 10/2006 | Starksen et al. |
| 2006/0241748 A1 | 10/2006 | Lee et al. |
| 2006/0247763 A1 | 11/2006 | Slater |
| 2006/0259135 A1 | 11/2006 | Navia et al. |
| 2006/0271175 A1 | 11/2006 | Woolfson et al. |
| 2006/0276871 A1 | 12/2006 | Lamson et al. |
| 2006/0282161 A1 | 12/2006 | Huynh et al. |
| 2006/0287661 A1 | 12/2006 | Bolduc et al. |
| 2006/0287716 A1 | 12/2006 | Banbury et al. |
| 2007/0001627 A1 | 1/2007 | Lin et al. |
| 2007/0010800 A1 | 1/2007 | Weitzner et al. |
| 2007/0016287 A1 | 1/2007 | Cartledge et al. |
| 2007/0016288 A1 | 1/2007 | Gurskis et al. |
| 2007/0021781 A1 | 1/2007 | Jervis et al. |
| 2007/0027533 A1 | 2/2007 | Douk |
| 2007/0027536 A1 | 2/2007 | Mihaljevic et al. |
| 2007/0032823 A1 | 2/2007 | Tegg |
| 2007/0038221 A1 | 2/2007 | Fine et al. |
| 2007/0038293 A1 | 2/2007 | St.Goar et al. |
| 2007/0038296 A1 | 2/2007 | Navia et al. |
| 2007/0039425 A1 | 2/2007 | Wang |
| 2007/0049942 A1* | 3/2007 | Hindrichs ............. A61F 2/2451 623/13.14 |
| 2007/0049970 A1 | 3/2007 | Belef et al. |
| 2007/0051377 A1 | 3/2007 | Douk et al. |
| 2007/0055206 A1 | 3/2007 | To et al. |
| 2007/0061010 A1 | 3/2007 | Hauser et al. |
| 2007/0066863 A1 | 3/2007 | Rafiee et al. |
| 2007/0078297 A1 | 4/2007 | Rafiee et al. |
| 2007/0080188 A1 | 4/2007 | Spence et al. |
| 2007/0083168 A1 | 4/2007 | Whiting et al. |
| 2007/0100427 A1 | 5/2007 | Perouse |
| 2007/0106328 A1 | 5/2007 | Wardle et al. |
| 2007/0112359 A1 | 5/2007 | Kimura et al. |
| 2007/0112422 A1 | 5/2007 | Dehdashtian |
| 2007/0118151 A1 | 5/2007 | Davidson |
| 2007/0118154 A1 | 5/2007 | Crabtree |
| 2007/0118213 A1 | 5/2007 | Loulmet |
| 2007/0118215 A1 | 5/2007 | Moaddeb |
| 2007/0142907 A1 | 6/2007 | Moaddeb et al. |
| 2007/0162111 A1 | 7/2007 | Fukamachi et al. |
| 2007/0198082 A1 | 8/2007 | Kapadia et al. |
| 2007/0219558 A1 | 9/2007 | Deutsch |
| 2007/0239208 A1 | 10/2007 | Crawford |
| 2007/0255397 A1 | 11/2007 | Ryan et al. |
| 2007/0255400 A1 | 11/2007 | Parravicini et al. |
| 2007/0270679 A1 | 11/2007 | Nguyen et al. |
| 2007/0270755 A1 | 11/2007 | Von Oepen et al. |
| 2007/0276437 A1 | 11/2007 | Call et al. |
| 2007/0282375 A1 | 12/2007 | Hindrichs et al. |
| 2007/0282429 A1 | 12/2007 | Hauser et al. |
| 2007/0295172 A1 | 12/2007 | Swartz |
| 2007/0299424 A1 | 12/2007 | Cumming et al. |
| 2008/0004697 A1 | 1/2008 | Lichtenstein et al. |
| 2008/0027483 A1 | 1/2008 | Cartledge et al. |

(56) References Cited

U.S. PATENT DOCUMENTS

| | | |
|---|---|---|
| 2008/0027555 A1 | 1/2008 | Hawkins |
| 2008/0035160 A1 | 2/2008 | Woodson et al. |
| 2008/0039935 A1 | 2/2008 | Buch et al. |
| 2008/0051703 A1 | 2/2008 | Thornton et al. |
| 2008/0058595 A1 | 3/2008 | Snoke et al. |
| 2008/0065011 A1 | 3/2008 | Marchand et al. |
| 2008/0065204 A1 | 3/2008 | Macoviak et al. |
| 2008/0071366 A1 | 3/2008 | Tuval et al. |
| 2008/0086138 A1 | 4/2008 | Stone et al. |
| 2008/0086203 A1 | 4/2008 | Roberts |
| 2008/0091169 A1 | 4/2008 | Heideman et al. |
| 2008/0091257 A1 | 4/2008 | Andreas et al. |
| 2008/0097483 A1 | 4/2008 | Ortiz et al. |
| 2008/0097523 A1 | 4/2008 | Bolduc et al. |
| 2008/0103572 A1 | 5/2008 | Gerber |
| 2008/0125861 A1 | 5/2008 | Webler et al. |
| 2008/0140116 A1 | 6/2008 | Bonutti |
| 2008/0167713 A1 | 7/2008 | Bolling |
| 2008/0167714 A1 | 7/2008 | St. Goar et al. |
| 2008/0195126 A1 | 8/2008 | Solem |
| 2008/0195200 A1 | 8/2008 | Vidlund et al. |
| 2008/0208265 A1 | 8/2008 | Frazier et al. |
| 2008/0221672 A1 | 9/2008 | Lamphere et al. |
| 2008/0228265 A1 | 9/2008 | Spence et al. |
| 2008/0234729 A1 | 9/2008 | Page et al. |
| 2008/0262480 A1 | 10/2008 | Stahler et al. |
| 2008/0262609 A1 | 10/2008 | Gross et al. |
| 2008/0275300 A1 | 11/2008 | Rothe et al. |
| 2008/0275469 A1 | 11/2008 | Fanton et al. |
| 2008/0275551 A1 | 11/2008 | Alfieri |
| 2008/0281353 A1 | 11/2008 | Aranyi et al. |
| 2008/0281411 A1 | 11/2008 | Berreklouw |
| 2008/0287862 A1 | 11/2008 | Weitzner et al. |
| 2008/0288044 A1 | 11/2008 | Osborne |
| 2008/0288062 A1 | 11/2008 | Andrieu et al. |
| 2008/0300537 A1 | 12/2008 | Bowman |
| 2008/0300629 A1 | 12/2008 | Surti |
| 2008/0312506 A1 | 12/2008 | Spivey et al. |
| 2009/0024110 A1 | 1/2009 | Heideman et al. |
| 2009/0028670 A1 | 1/2009 | Garcia et al. |
| 2009/0043381 A1 | 2/2009 | Macoviak et al. |
| 2009/0054723 A1 | 2/2009 | Khairkhahan et al. |
| 2009/0054969 A1 | 2/2009 | Salahieh et al. |
| 2009/0062866 A1 | 3/2009 | Jackson |
| 2009/0076586 A1 | 3/2009 | Hauser et al. |
| 2009/0076600 A1 | 3/2009 | Quinn |
| 2009/0088837 A1 | 4/2009 | Gillinov et al. |
| 2009/0093877 A1 | 4/2009 | Keidar et al. |
| 2009/0099650 A1 | 4/2009 | Bolduc et al. |
| 2009/0105816 A1 | 4/2009 | Olsen et al. |
| 2009/0125102 A1 | 5/2009 | Cartledge et al. |
| 2009/0166913 A1 | 7/2009 | Guo et al. |
| 2009/0171439 A1 | 7/2009 | Nissl |
| 2009/0177266 A1 | 7/2009 | Powell et al. |
| 2009/0177274 A1 | 7/2009 | Scorsin et al. |
| 2009/0222083 A1 | 9/2009 | Nguyen et al. |
| 2009/0248148 A1 | 10/2009 | Shaolian et al. |
| 2009/0254103 A1 | 10/2009 | Deutsch |
| 2009/0264994 A1 | 10/2009 | Saadat |
| 2009/0287231 A1 | 11/2009 | Brooks et al. |
| 2009/0287304 A1 | 11/2009 | Dahlgren et al. |
| 2009/0299409 A1 | 12/2009 | Coe et al. |
| 2009/0326648 A1 | 12/2009 | Machold et al. |
| 2010/0001038 A1* | 1/2010 | Levin ............... A61B 17/068 227/179.1 |
| 2010/0010538 A1 | 1/2010 | Juravic et al. |
| 2010/0023118 A1 | 1/2010 | Medlock et al. |
| 2010/0030014 A1 | 2/2010 | Ferrazzi |
| 2010/0030328 A1 | 2/2010 | Seguin et al. |
| 2010/0042147 A1 | 2/2010 | Janovsky et al. |
| 2010/0063542 A1 | 3/2010 | van der Burg et al. |
| 2010/0063550 A1 | 3/2010 | Felix et al. |
| 2010/0076499 A1 | 3/2010 | McNamara et al. |
| 2010/0094248 A1 | 4/2010 | Nguyen et al. |
| 2010/0106141 A1 | 4/2010 | Osypka et al. |
| 2010/0114180 A1 | 5/2010 | Rock et al. |
| 2010/0121349 A1 | 5/2010 | Meier et al. |
| 2010/0121435 A1 | 5/2010 | Subramanian et al. |
| 2010/0121437 A1 | 5/2010 | Subramanian et al. |
| 2010/0130989 A1* | 5/2010 | Bourque ............ A61B 17/0401 606/144 |
| 2010/0130992 A1 | 5/2010 | Machold et al. |
| 2010/0152845 A1 | 6/2010 | Bloom et al. |
| 2010/0161043 A1 | 6/2010 | Maisano et al. |
| 2010/0168827 A1 | 7/2010 | Schultz |
| 2010/0168845 A1 | 7/2010 | Wright |
| 2010/0174358 A1 | 7/2010 | Rabkin et al. |
| 2010/0179574 A1 | 7/2010 | Longoria et al. |
| 2010/0217184 A1 | 8/2010 | Koblish et al. |
| 2010/0217382 A1 | 8/2010 | Chau et al. |
| 2010/0234935 A1 | 9/2010 | Bashiri et al. |
| 2010/0249497 A1 | 9/2010 | Peine et al. |
| 2010/0249908 A1 | 9/2010 | Chau et al. |
| 2010/0249915 A1 | 9/2010 | Zhang |
| 2010/0249920 A1 | 9/2010 | Bolling et al. |
| 2010/0262232 A1 | 10/2010 | Annest |
| 2010/0262233 A1 | 10/2010 | He |
| 2010/0286628 A1 | 11/2010 | Gross |
| 2010/0305475 A1 | 12/2010 | Hinchliffe et al. |
| 2010/0324598 A1 | 12/2010 | Anderson |
| 2011/0004210 A1 | 1/2011 | Johnson et al. |
| 2011/0004298 A1 | 1/2011 | Lee et al. |
| 2011/0009956 A1 | 1/2011 | Cartledge et al. |
| 2011/0011917 A1 | 1/2011 | Loulmet |
| 2011/0026208 A1 | 2/2011 | Utsuro et al. |
| 2011/0029066 A1 | 2/2011 | Gilad et al. |
| 2011/0035000 A1 | 2/2011 | Nieminen et al. |
| 2011/0066231 A1 | 3/2011 | Cartledge et al. |
| 2011/0067770 A1 | 3/2011 | Pederson et al. |
| 2011/0071626 A1 | 3/2011 | Wright et al. |
| 2011/0082538 A1 | 4/2011 | Dahlgren et al. |
| 2011/0087146 A1 | 4/2011 | Ryan et al. |
| 2011/0093002 A1 | 4/2011 | Rucker et al. |
| 2011/0106247 A1 | 5/2011 | Miller et al. |
| 2011/0118832 A1 | 5/2011 | Punjabi |
| 2011/0137410 A1 | 6/2011 | Hacohen |
| 2011/0144703 A1 | 6/2011 | Krause et al. |
| 2011/0202130 A1 | 8/2011 | Cartledge et al. |
| 2011/0208283 A1 | 8/2011 | Rust |
| 2011/0230941 A1 | 9/2011 | Markus |
| 2011/0230961 A1 | 9/2011 | Langer et al. |
| 2011/0238088 A1 | 9/2011 | Bolduc et al. |
| 2011/0257433 A1 | 10/2011 | Walker |
| 2011/0257633 A1 | 10/2011 | Cartledge et al. |
| 2011/0264208 A1 | 10/2011 | Duffy et al. |
| 2011/0276062 A1 | 11/2011 | Bolduc |
| 2011/0288435 A1 | 11/2011 | Christy et al. |
| 2011/0301498 A1 | 12/2011 | Maenhout et al. |
| 2012/0053628 A1 | 3/2012 | Sojka et al. |
| 2012/0078355 A1 | 3/2012 | Zipory et al. |
| 2012/0078359 A1 | 3/2012 | Li et al. |
| 2012/0089022 A1 | 4/2012 | House et al. |
| 2012/0089125 A1 | 4/2012 | Scheibe et al. |
| 2012/0095552 A1 | 4/2012 | Spence et al. |
| 2012/0109155 A1 | 5/2012 | Robinson et al. |
| 2012/0150290 A1 | 6/2012 | Gabbay |
| 2012/0158021 A1 | 6/2012 | Morrill |
| 2012/0179086 A1 | 7/2012 | Shank et al. |
| 2012/0191182 A1 | 7/2012 | Hauser et al. |
| 2012/0226349 A1 | 9/2012 | Tuval et al. |
| 2012/0239142 A1 | 9/2012 | Liu et al. |
| 2012/0245604 A1 | 9/2012 | Tegzes |
| 2012/0271198 A1 | 10/2012 | Whittaker et al. |
| 2012/0296349 A1 | 11/2012 | Smith et al. |
| 2012/0296417 A1 | 11/2012 | Hill et al. |
| 2012/0310330 A1 | 12/2012 | Buchbinder et al. |
| 2012/0323313 A1 | 12/2012 | Seguin |
| 2013/0030522 A1 | 1/2013 | Rowe et al. |
| 2013/0046373 A1 | 2/2013 | Cartledge et al. |
| 2013/0053884 A1 | 2/2013 | Roorda |
| 2013/0079873 A1 | 3/2013 | Migliazza et al. |
| 2013/0085529 A1 | 4/2013 | Housman |
| 2013/0090724 A1 | 4/2013 | Subramanian et al. |
| 2013/0096673 A1 | 4/2013 | Hill et al. |

(56) References Cited

U.S. PATENT DOCUMENTS

| | | |
|---|---|---|
| 2013/0116776 A1 | 5/2013 | Gross et al. |
| 2013/0123910 A1 | 5/2013 | Cartledge et al. |
| 2013/0131791 A1 | 5/2013 | Hlavka et al. |
| 2013/0166017 A1 | 6/2013 | Cartledge et al. |
| 2013/0190863 A1 | 7/2013 | Call et al. |
| 2013/0204361 A1 | 8/2013 | Adams et al. |
| 2013/0226289 A1 | 8/2013 | Shaolian et al. |
| 2013/0226290 A1 | 8/2013 | Yellin et al. |
| 2013/0268069 A1 | 10/2013 | Zakai et al. |
| 2013/0282059 A1 | 10/2013 | Ketai et al. |
| 2013/0289718 A1 | 10/2013 | Tsukashima et al. |
| 2013/0297013 A1 | 11/2013 | Klima et al. |
| 2013/0304093 A1 | 11/2013 | Serina et al. |
| 2013/0331930 A1 | 12/2013 | Rowe et al. |
| 2014/0067054 A1 | 3/2014 | Chau et al. |
| 2014/0088368 A1 | 3/2014 | Park |
| 2014/0088646 A1 | 3/2014 | Wales et al. |
| 2014/0094826 A1 | 4/2014 | Sutherland et al. |
| 2014/0094903 A1 | 4/2014 | Miller et al. |
| 2014/0094906 A1 | 4/2014 | Spence et al. |
| 2014/0114390 A1 | 4/2014 | Tobis et al. |
| 2014/0135799 A1 | 5/2014 | Henderson |
| 2014/0142619 A1 | 5/2014 | Serina et al. |
| 2014/0142695 A1 | 5/2014 | Gross et al. |
| 2014/0148849 A1 | 5/2014 | Serina et al. |
| 2014/0155783 A1 | 6/2014 | Starksen et al. |
| 2014/0163670 A1 | 6/2014 | Alon et al. |
| 2014/0163690 A1 | 6/2014 | White |
| 2014/0188108 A1 | 7/2014 | Goodine et al. |
| 2014/0188140 A1 | 7/2014 | Meier et al. |
| 2014/0188215 A1 | 7/2014 | Hlavka et al. |
| 2014/0194976 A1 | 7/2014 | Starksen et al. |
| 2014/0207231 A1 | 7/2014 | Hacohen et al. |
| 2014/0243859 A1 | 8/2014 | Robinson |
| 2014/0243894 A1 | 8/2014 | Groothuis et al. |
| 2014/0243963 A1 | 8/2014 | Sheps et al. |
| 2014/0251042 A1 | 9/2014 | Asselin et al. |
| 2014/0275757 A1 | 9/2014 | Goodwin et al. |
| 2014/0276648 A1 | 9/2014 | Hammer et al. |
| 2014/0296962 A1 | 10/2014 | Cartledge et al. |
| 2014/0303649 A1 | 10/2014 | Nguyen et al. |
| 2014/0303720 A1 | 10/2014 | Sugimoto et al. |
| 2014/0309661 A1 | 10/2014 | Sheps et al. |
| 2014/0309730 A1 | 10/2014 | Alon et al. |
| 2014/0343668 A1 | 11/2014 | Zipory et al. |
| 2014/0350660 A1 | 11/2014 | Cocks et al. |
| 2014/0379006 A1 | 12/2014 | Sutherland et al. |
| 2015/0018940 A1 | 1/2015 | Quill et al. |
| 2015/0051697 A1 | 2/2015 | Spence et al. |
| 2015/0081014 A1 | 3/2015 | Gross et al. |
| 2015/0094800 A1 | 4/2015 | Chawla |
| 2015/0100116 A1 | 4/2015 | Mohl et al. |
| 2015/0112432 A1 | 4/2015 | Reich et al. |
| 2015/0127097 A1 | 5/2015 | Neumann et al. |
| 2015/0133997 A1 | 5/2015 | Deitch et al. |
| 2015/0182336 A1 | 7/2015 | Zipory et al. |
| 2015/0230919 A1 | 8/2015 | Chau et al. |
| 2015/0272586 A1 | 10/2015 | Herman et al. |
| 2015/0272734 A1 | 10/2015 | Sheps et al. |
| 2015/0282931 A1 | 10/2015 | Brunnett et al. |
| 2015/0351906 A1 | 12/2015 | Hammer et al. |
| 2015/0351910 A1 | 12/2015 | Gilmore et al. |
| 2016/0008132 A1 | 1/2016 | Cabiri et al. |
| 2016/0058557 A1 | 3/2016 | Reich et al. |
| 2016/0113767 A1 | 4/2016 | Miller et al. |
| 2016/0120642 A1 | 5/2016 | Shaolian et al. |
| 2016/0120645 A1 | 5/2016 | Alon |
| 2016/0158008 A1 | 6/2016 | Miller et al. |
| 2016/0242762 A1 | 8/2016 | Gilmore et al. |
| 2016/0262755 A1 | 9/2016 | Zipory et al. |
| 2016/0302917 A1 | 10/2016 | Schewel |
| 2016/0317302 A1 | 11/2016 | Madjarov et al. |
| 2016/0361058 A1 | 12/2016 | Bolduc et al. |
| 2016/0361168 A1 | 12/2016 | Gross et al. |
| 2016/0361169 A1 | 12/2016 | Gross et al. |
| 2017/0000609 A1 | 1/2017 | Gross et al. |
| 2017/0042670 A1 | 2/2017 | Shaolian et al. |
| 2017/0224489 A1 | 8/2017 | Starksen et al. |
| 2017/0245993 A1 | 8/2017 | Gross et al. |
| 2017/0325959 A1 | 11/2017 | Sheps et al. |
| 2018/0008409 A1 | 1/2018 | Kutzik et al. |
| 2018/0049875 A1 | 2/2018 | Iflah et al. |
| 2018/0168803 A1 | 6/2018 | Pesce et al. |
| 2018/0289480 A1 | 10/2018 | D'ambra et al. |
| 2018/0318080 A1 | 11/2018 | Quill et al. |
| 2018/0318083 A1 | 11/2018 | Bolling et al. |
| 2019/0029498 A1 | 1/2019 | Mankowski et al. |
| 2019/0038411 A1 | 2/2019 | Alon |
| 2019/0111239 A1 | 4/2019 | Bolduc et al. |
| 2019/0117400 A1 | 4/2019 | Medema et al. |
| 2019/0125325 A1 | 5/2019 | Sheps et al. |
| 2019/0151093 A1 | 5/2019 | Keidar et al. |
| 2019/0175346 A1 | 6/2019 | Schaffner et al. |
| 2019/0183648 A1 | 6/2019 | Trapp et al. |
| 2019/0290260 A1 | 9/2019 | Caffes et al. |
| 2019/0290431 A1 | 9/2019 | Genovese et al. |
| 2019/0343633 A1 | 11/2019 | Garvin et al. |

FOREIGN PATENT DOCUMENTS

| | | |
|---|---|---|
| EP | 2273928 A2 | 1/2011 |
| EP | 3531975 A1 | 9/2019 |
| WO | 9205093 A1 | 4/1992 |
| WO | 9846149 A1 | 10/1998 |
| WO | 0009048 A1 | 2/2000 |
| WO | 02085250 A3 | 2/2003 |
| WO | 03047467 A1 | 6/2003 |
| WO | 2008014144 A3 | 6/2008 |
| WO | 2008031103 A3 | 10/2008 |
| WO | 2009130631 A2 | 10/2009 |
| WO | 2010000454 A1 | 1/2010 |
| WO | 2010065274 A1 | 6/2010 |
| WO | 2010150178 A2 | 12/2010 |
| WO | 2012106346 A1 | 8/2012 |
| WO | 2012176195 A3 | 3/2013 |
| WO | 2014064964 A1 | 5/2014 |
| WO | 2016087934 A1 | 6/2016 |
| WO | 2019145941 A1 | 8/2019 |
| WO | 2019145947 A1 | 8/2019 |
| WO | 2019182645 A1 | 9/2019 |
| WO | 2019224814 A1 | 11/2019 |

OTHER PUBLICATIONS

Ahmadi, A., G. Spillner, and Th Johannesson. "Hemodynamic changes following experimental production and correction of acute mitral regurgitation with an adjustable ring prosthesis." The Thoracic and cardiovascular surgeon36.06 (1988): 313-319.

Ahmadi, Ali et al. "Percutaneously adjustable pulmonary artery band." The Annals of thoracic surgery 60 (1995): S520-S522.

Alfieri et al., "An effective technique to correct anterior mitral leaflet prolapse," J Card 14(6):468-470 (1999).

Alfieri et al., "The double orifice technique in mitral valve repair: a simple solution for complex problems," Journal of Thoracic Cardiovascular Surgery 122:674-681 (2001).

Alfieri et al., "The edge to edge technique," The European Association for Cardio-Thoracic Surgery 14th Annual Meeting Oct. 7-11, Book of Procees. (2000).

Alfieri et al."Novel Suture Device for Beating-Heart Mitral Leaflet Approximation", Ann Thorac Surg. 2002, 74:1488-1493.

Alfieri, "The edge-to-edge repair of the mitral valve," [Abstract] 6th Annual NewEra Cardiac Care: Innovation & Technology, Heart Surgery Forum pp. 103. (2000).

Amplatzer Cardiac Plug brochure (English pages), AGA Medical Corporation (Plymouth, MN) (copyright 2008-2010, downloaded Jan. 11, 2011).

AMPLATZER® Cribriform Occluder. A patient guide to Percutaneous, Transcatheter, Atrial Septal Defect Closuer, AGA Medical Corporation, Apr. 2008.

AMPLATZER® Septal Occluder. A patient guide to the Non-Surgical Closuer of the Atrial Septal Defect Using the AMPLATZER Septal Occluder System, AGA Medical Corporation, Apr. 2008.

(56) References Cited

OTHER PUBLICATIONS

Assad, Renato S. "Adjustable Pulmonary Artery Banding." (2014).
Brennan, Jennifer, 510(k) Summary of safety and effectiveness, Jan. 2008.
Daebritz, S. et al. "Experience with an adjustable pulmonary artery banding device in two cases: initial success-midterm failure." The Thoracic and cardiovascular surgeon 47.01 (1999): 51-52.
Dang NC et al. "Simplified Placement of Multiple Artificial Mitral Valve Chords," The Heart Surgery Forum #2005-1005, 8 (3) (2005).
Dictionary.com definition of "lock", Jul. 29, 2013.
Dieter RS, "Percutaneous valve repair: Update on mitral regurgitation and endovascular approaches to the mitral valve," Applications in Imaging, Cardiac Interventions, Supported by an educational grant from Amersham Health pp. 11-14 (2003).
Elliott, Daniel S., Gerald W. Timm, and David M. Barrett. "An implantable mechanical urinary sphincter: a new nonhydraulic design concept." Urology52.6 (1998): 1151-1154.
Langer et al. Ring plus String: Papillary muscle repositioning as an adjunctive repair technique for ischemic mitral regurgitation, The Journal of Thoracic Cardiovascular surgery vol. 133 No. 1, Jan. 2007.
Langer et al. RING+STRING, Successful Repair technique for ischemic mitral regurgitation with severe leaflet Tethering, The Department of Thoracic Cardiovascular surgery, Hamburg, Germany, Nov. 2008.
Maisano, The double-orifice technique as a standardized approach to treat mitral . . . , European Journal of Cardio-thoracic Surgery 17 (2000) 201-205.
Odell JA et al., "Early Results o4yf a Simplified Method of Mitral Valve Annuloplasty," Circulation 92:150-154 (1995).
O'Reilly S et al., "Heart valve surgery pushes the envelope," Medtech Insight 8(3): 73, 99-108 (2006).
Park, Sang C. et al. "A percutaneously adjustable device for banding of the pulmonary trunk." International journal of cardiology 9.4 (1985): 477-484.
Swain CP et al., "An endoscopically deliverable tissue-transfixing device for securing biosensors in the gastrointestinal tract," Gastrointestinal Endoscopy 40(6): 730-734 (1994).
Swenson, O. An experimental implantable urinary sphincter. Invest Urol. Sep. 1976;14(2):100-3.
Swenson, O. and Malinin, T.I., 1978. An improved mechanical device for control of urinary incontinence. Investigative urology, 15(5), pp. 389-391.
Swenson, Orvar. "Internal device for control of urinary incontinence." Journal of pediatric surgery 7.5 (1972): 542-545.
Tajik, Abdul, "Two dimensional real-time ultrasonic imaging of the heart and great vessels", Mayo Clin Proc. vol. 53:271-303, 1978.

* cited by examiner

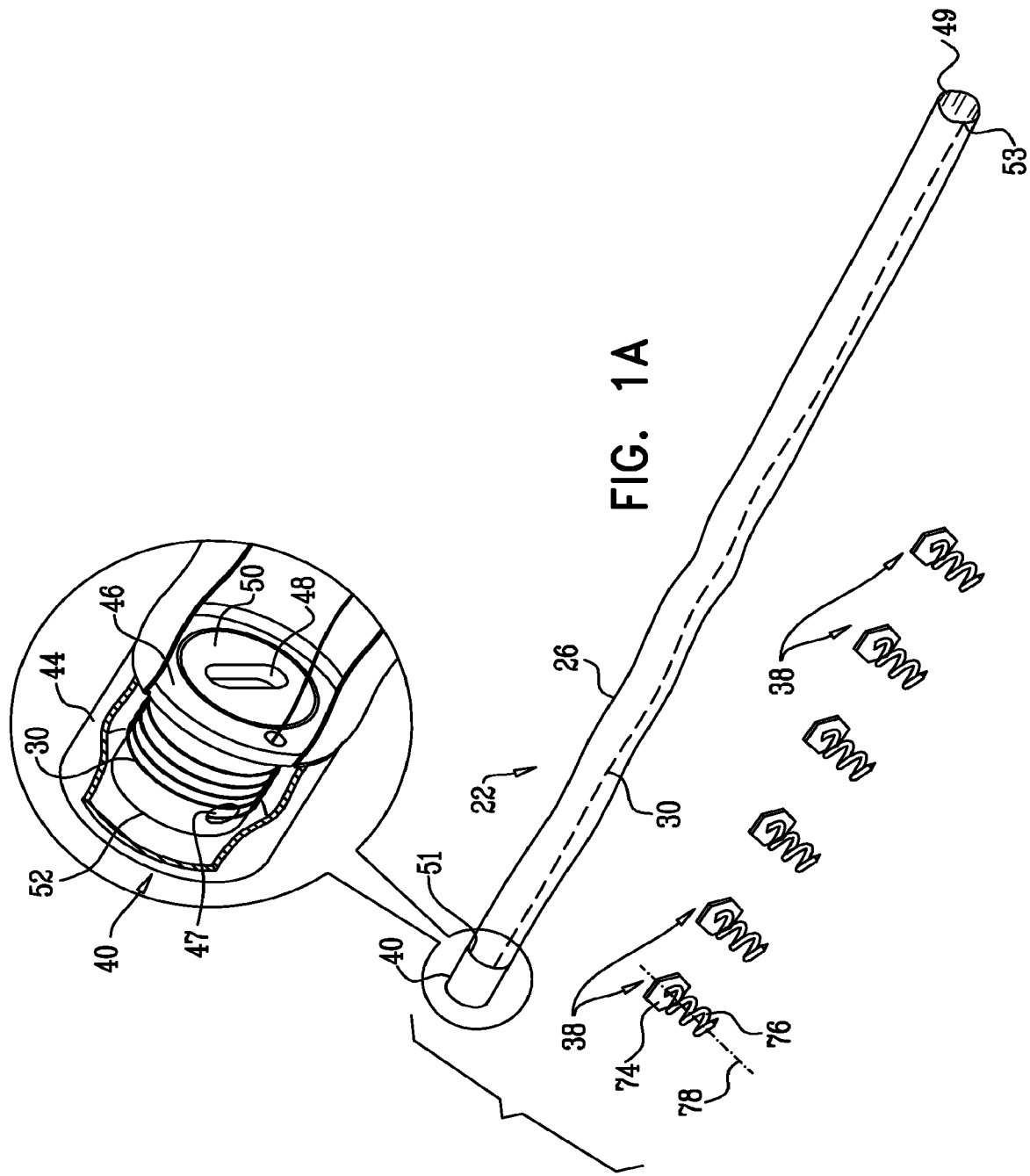

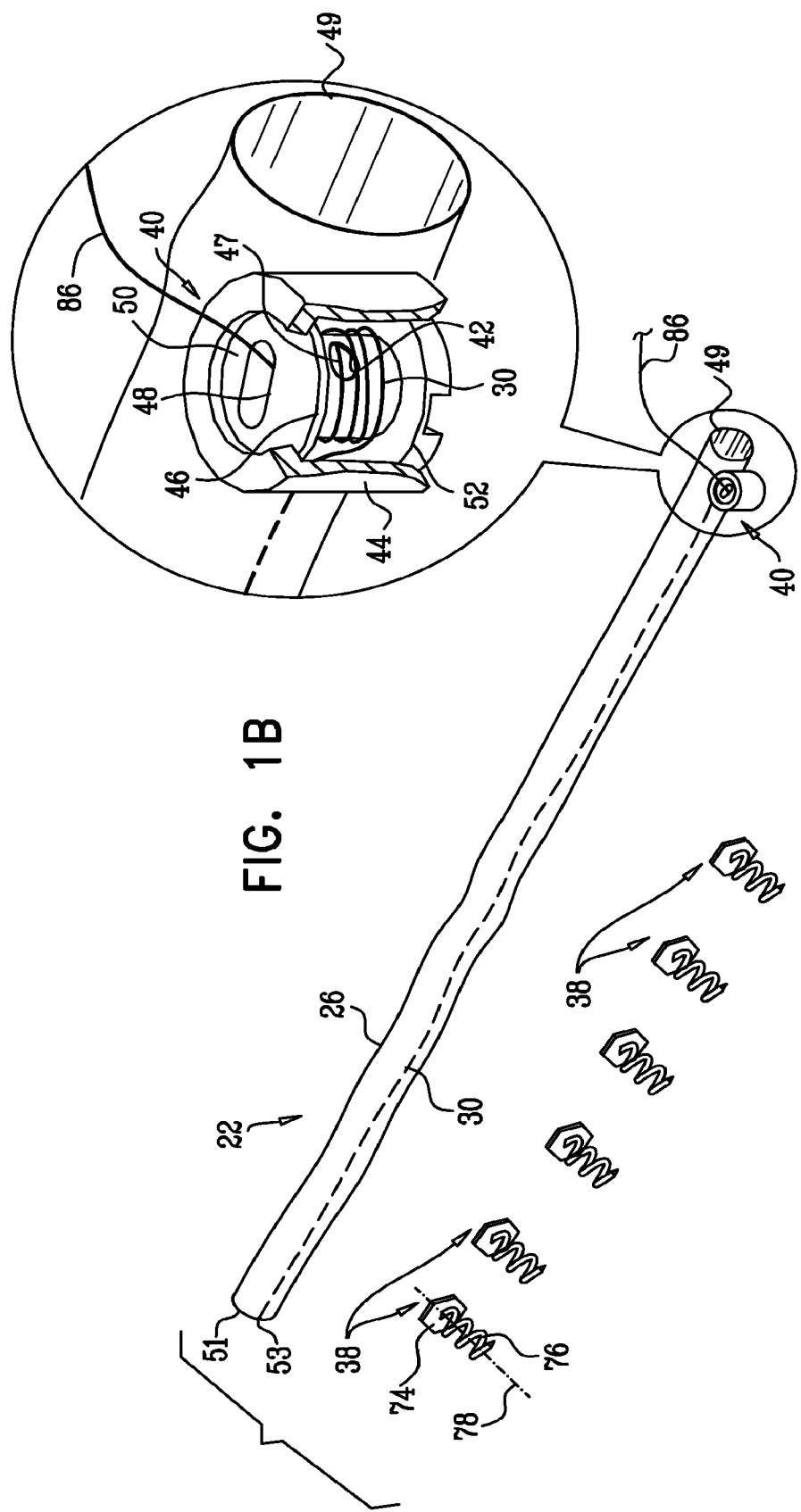

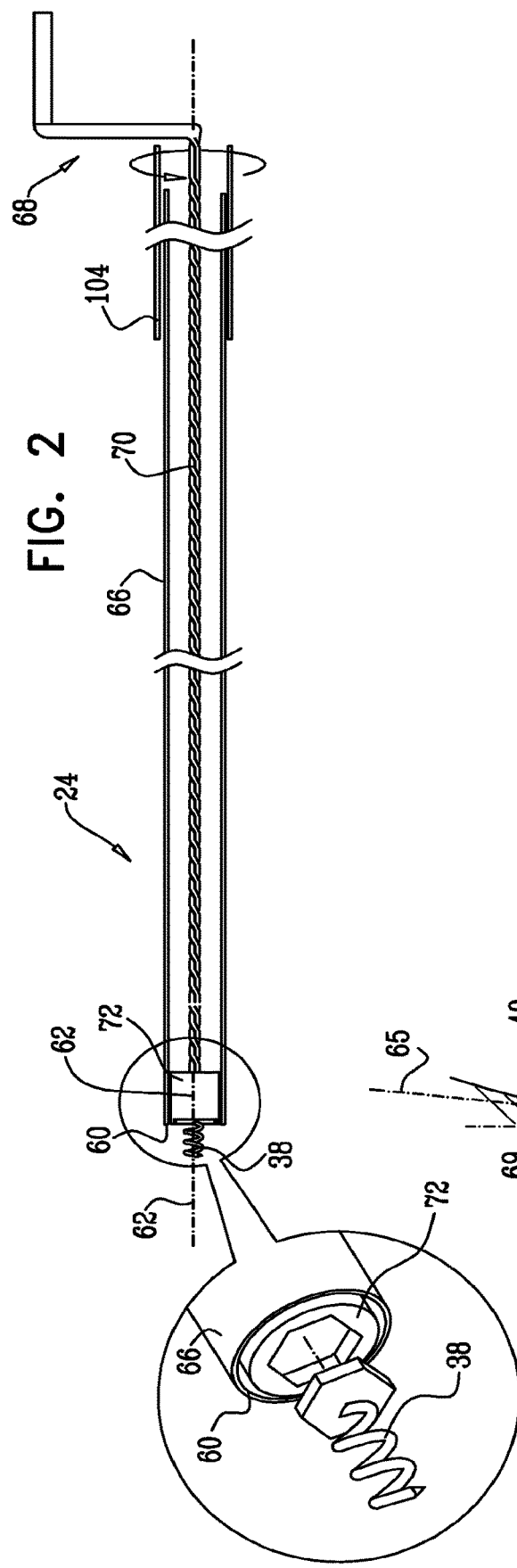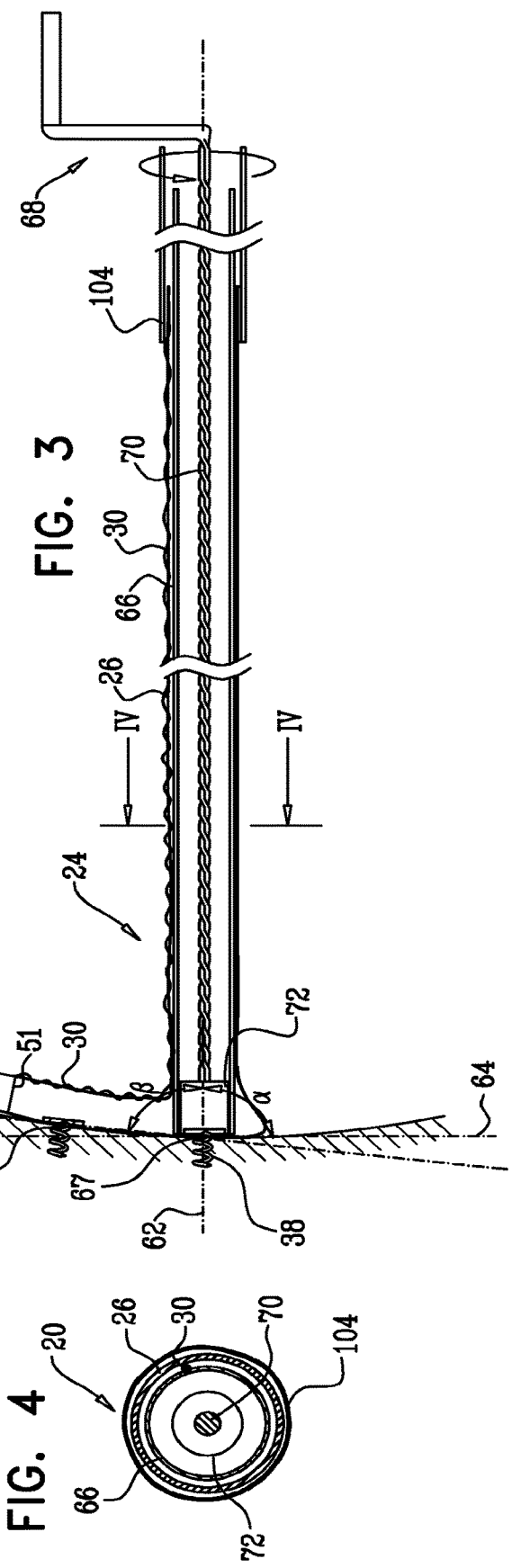

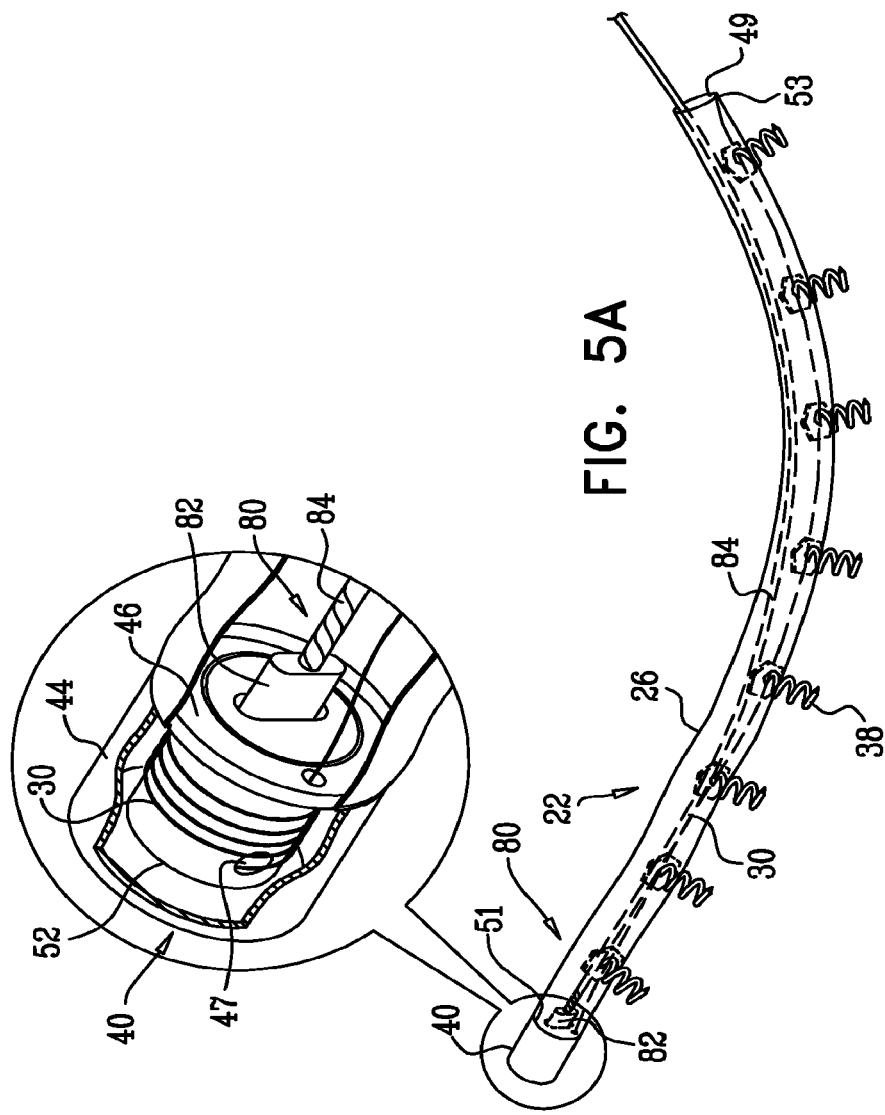

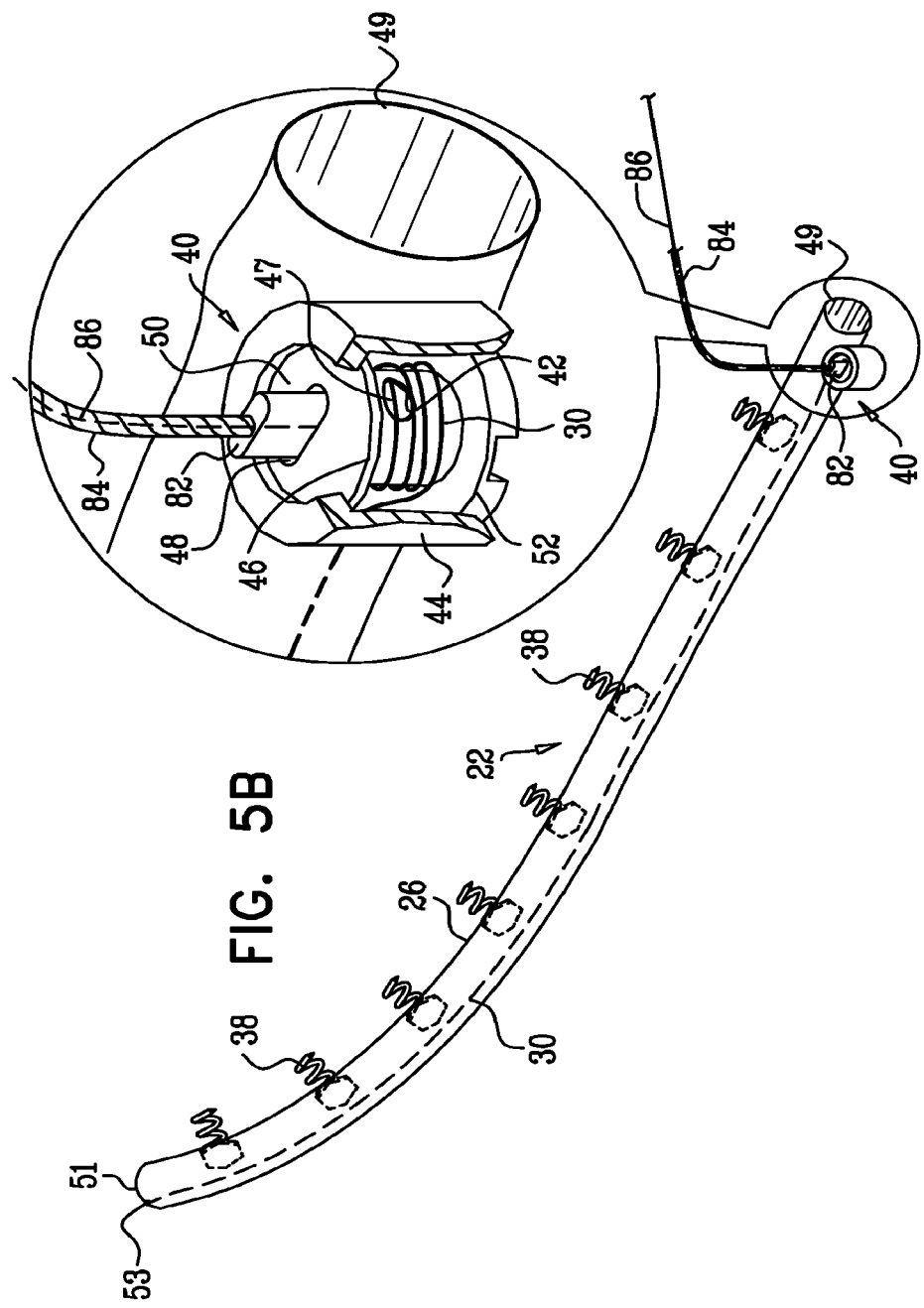

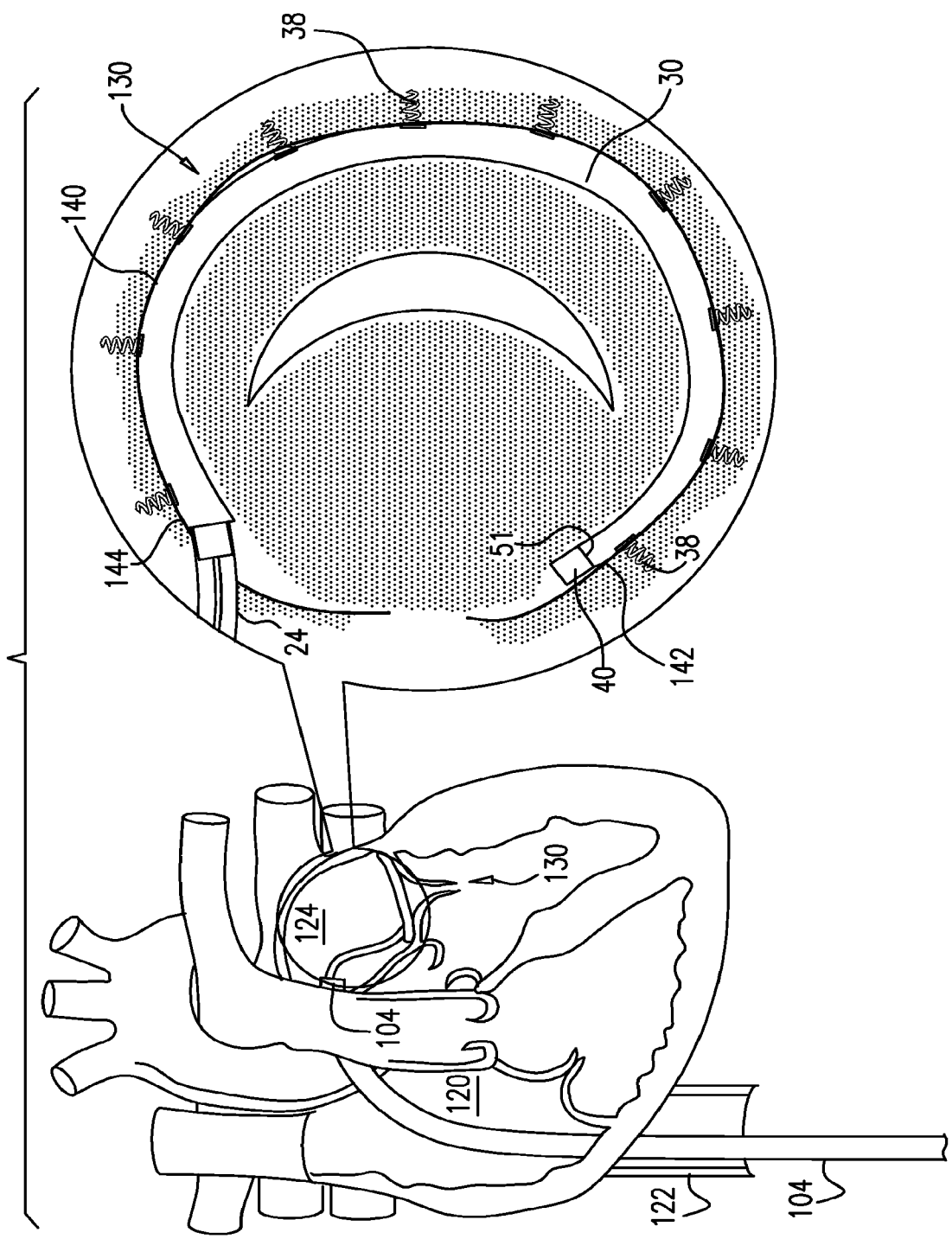

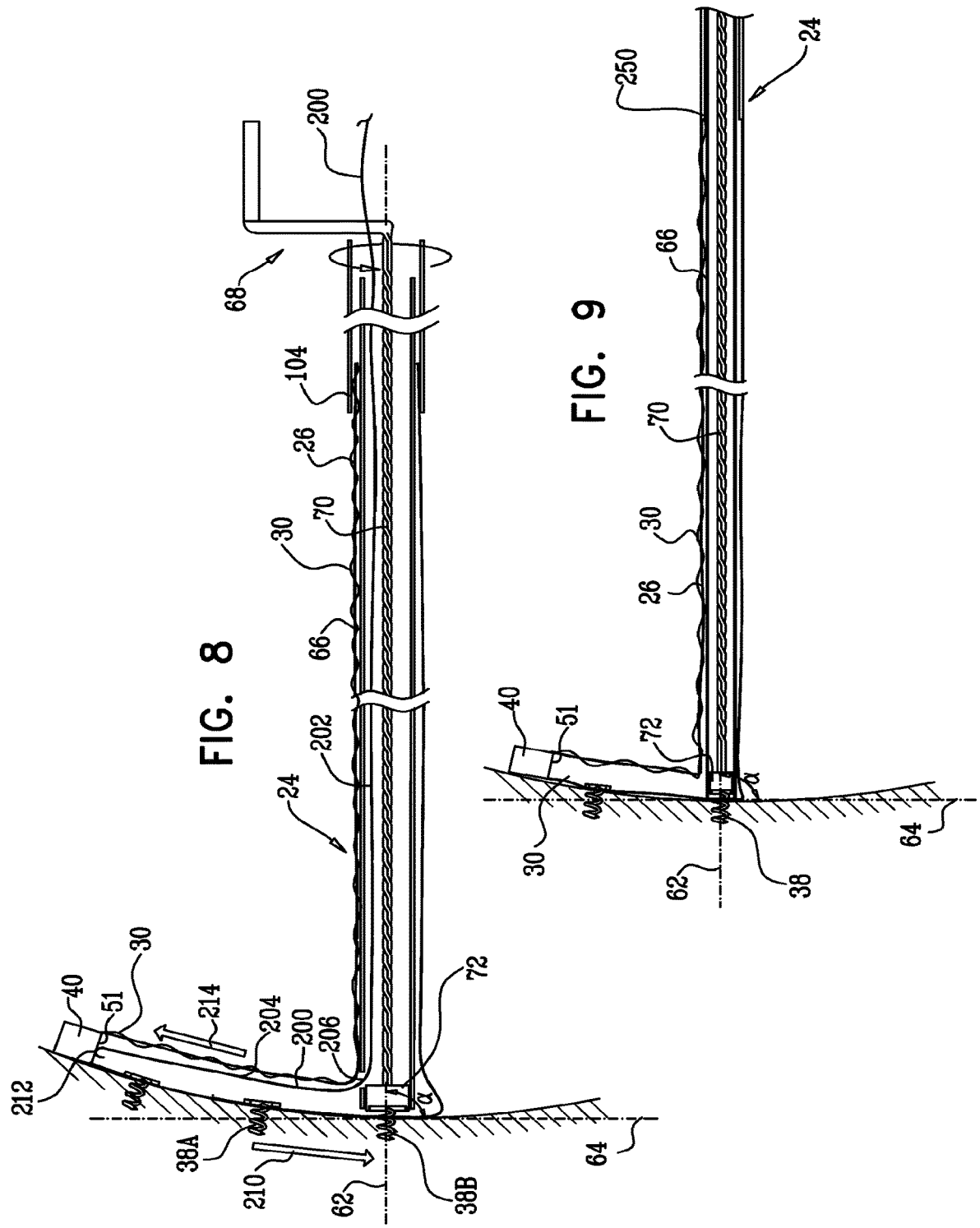

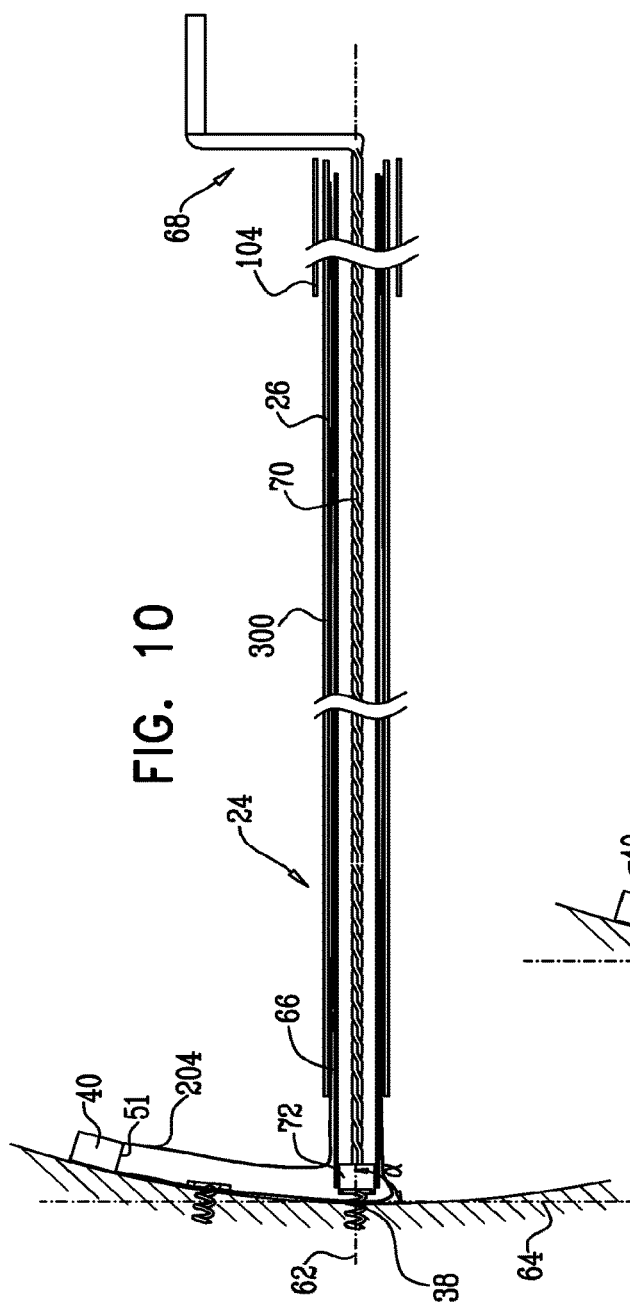
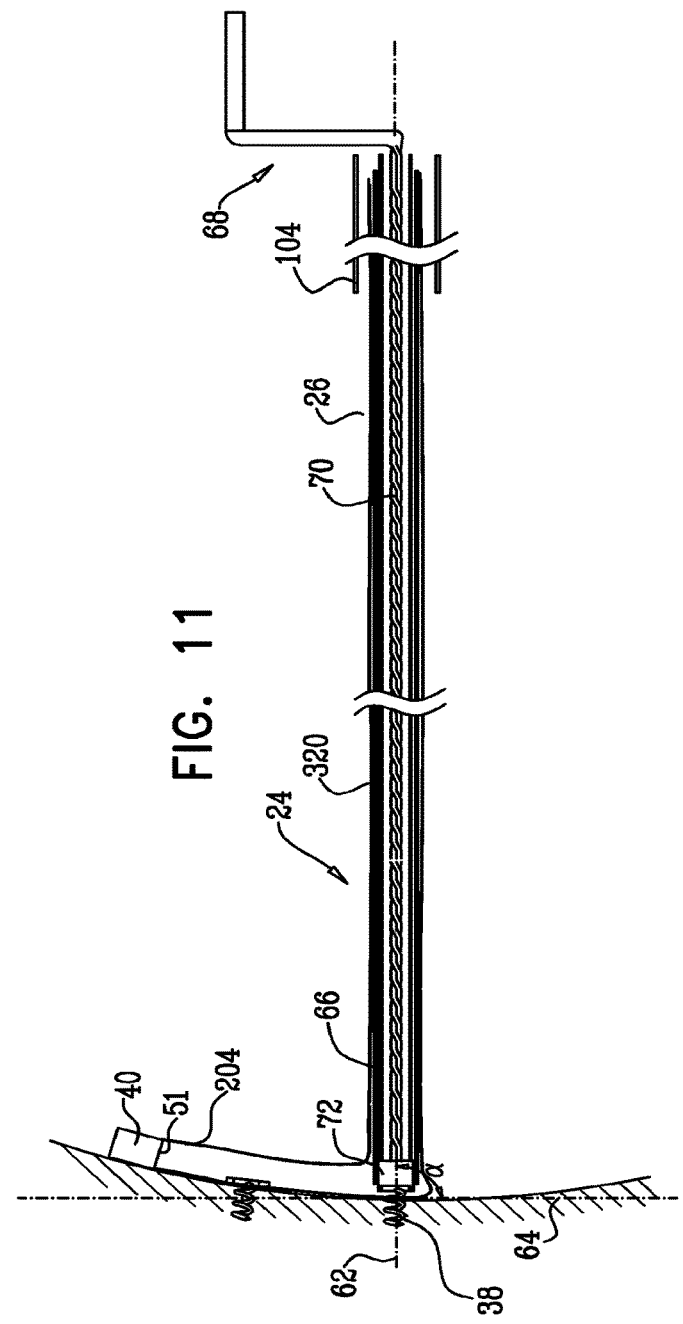

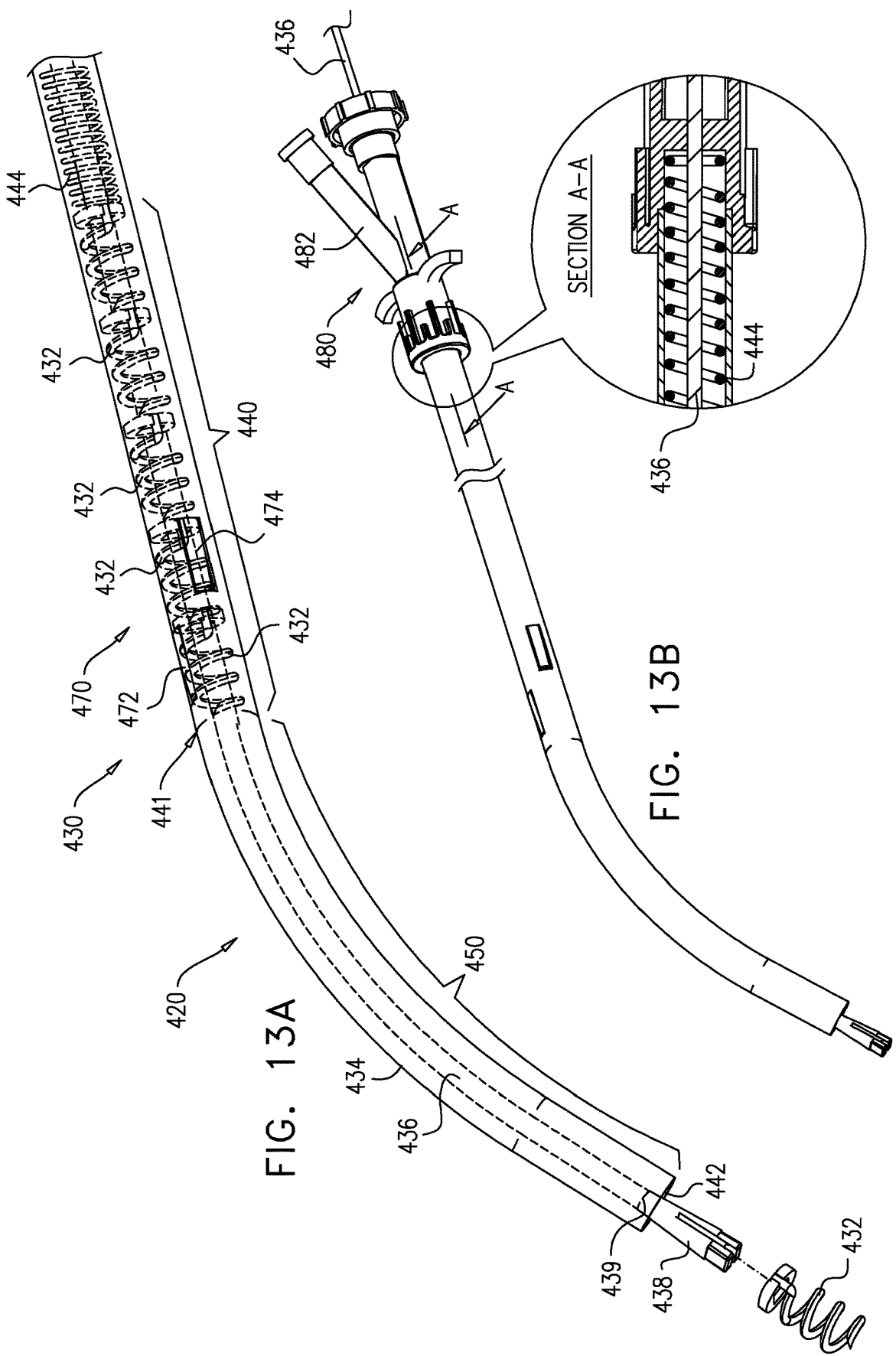

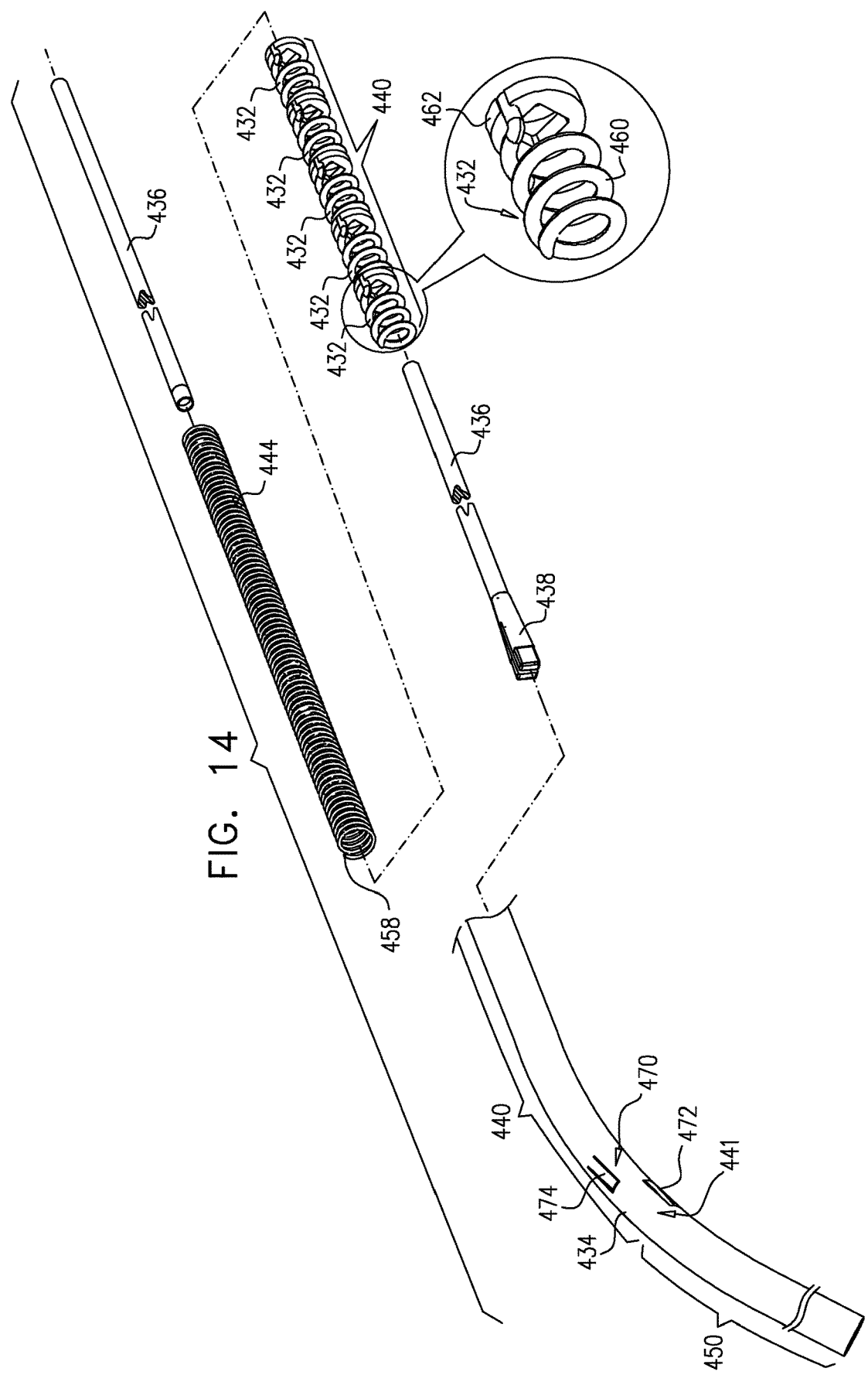

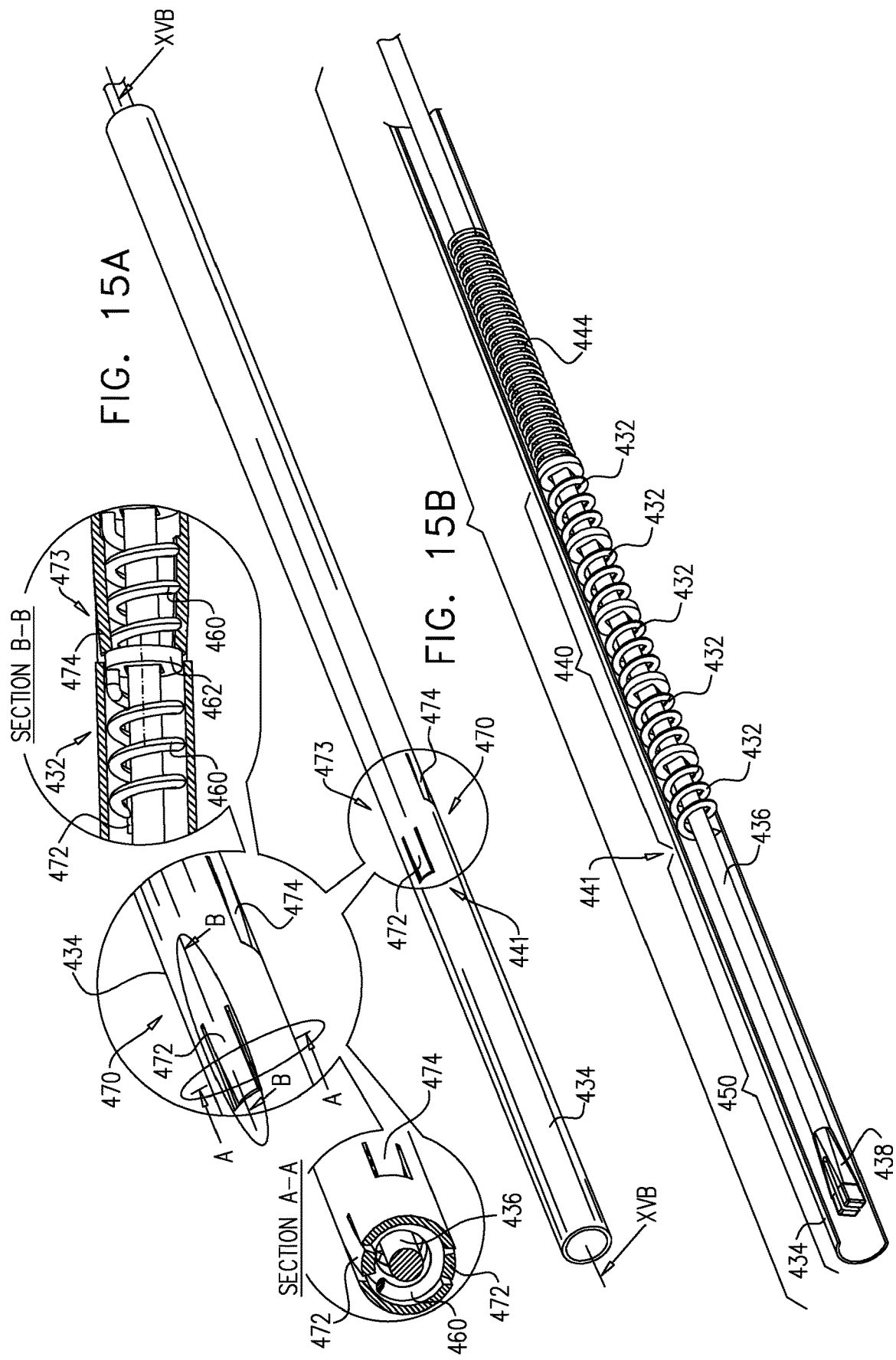

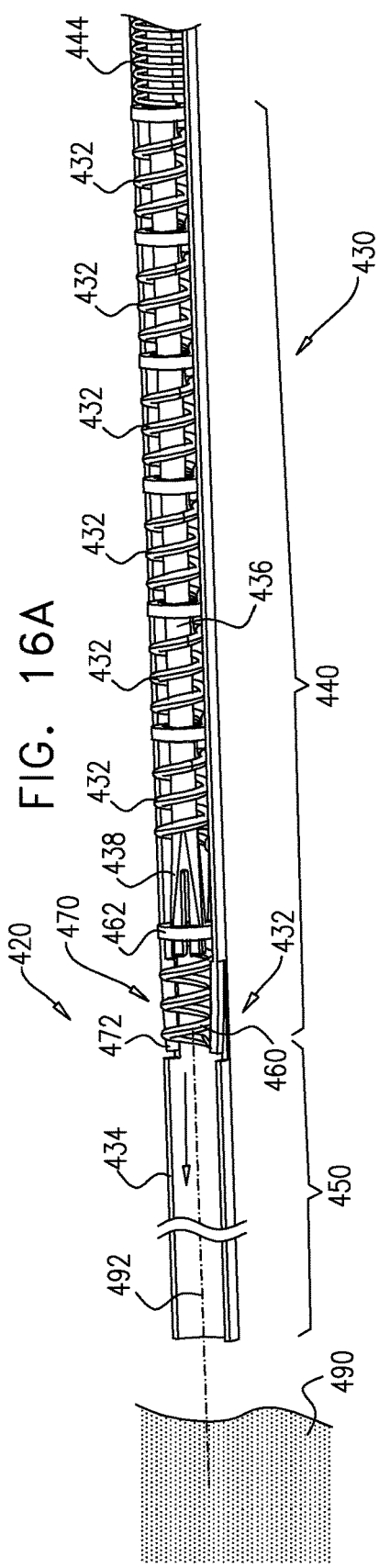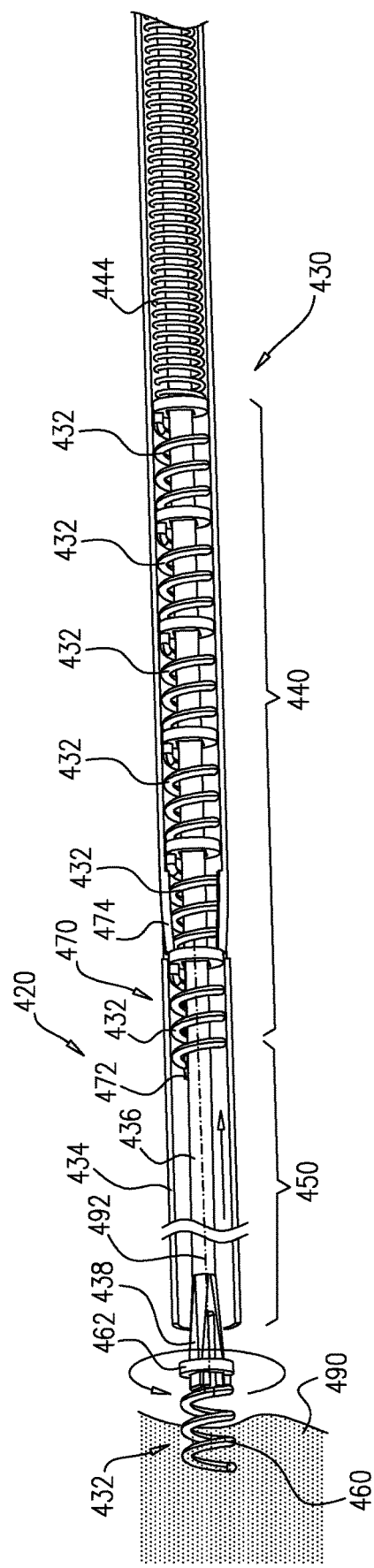

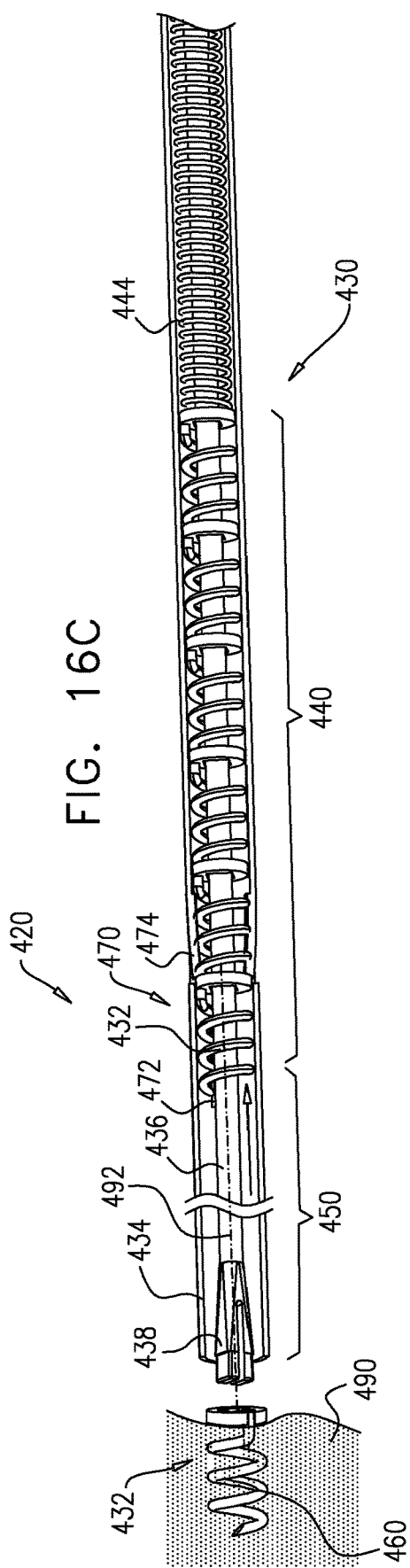
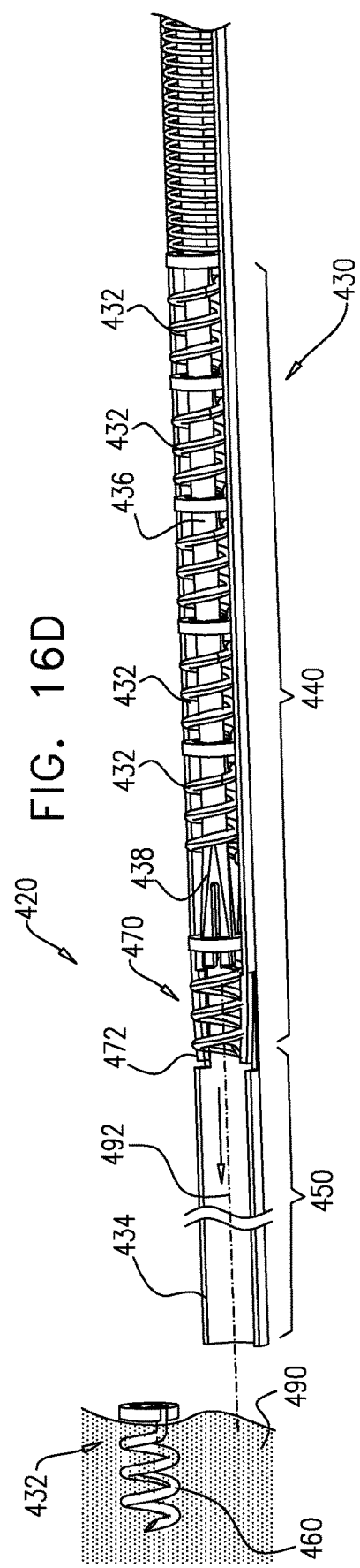
FIG. 16C
FIG. 16D

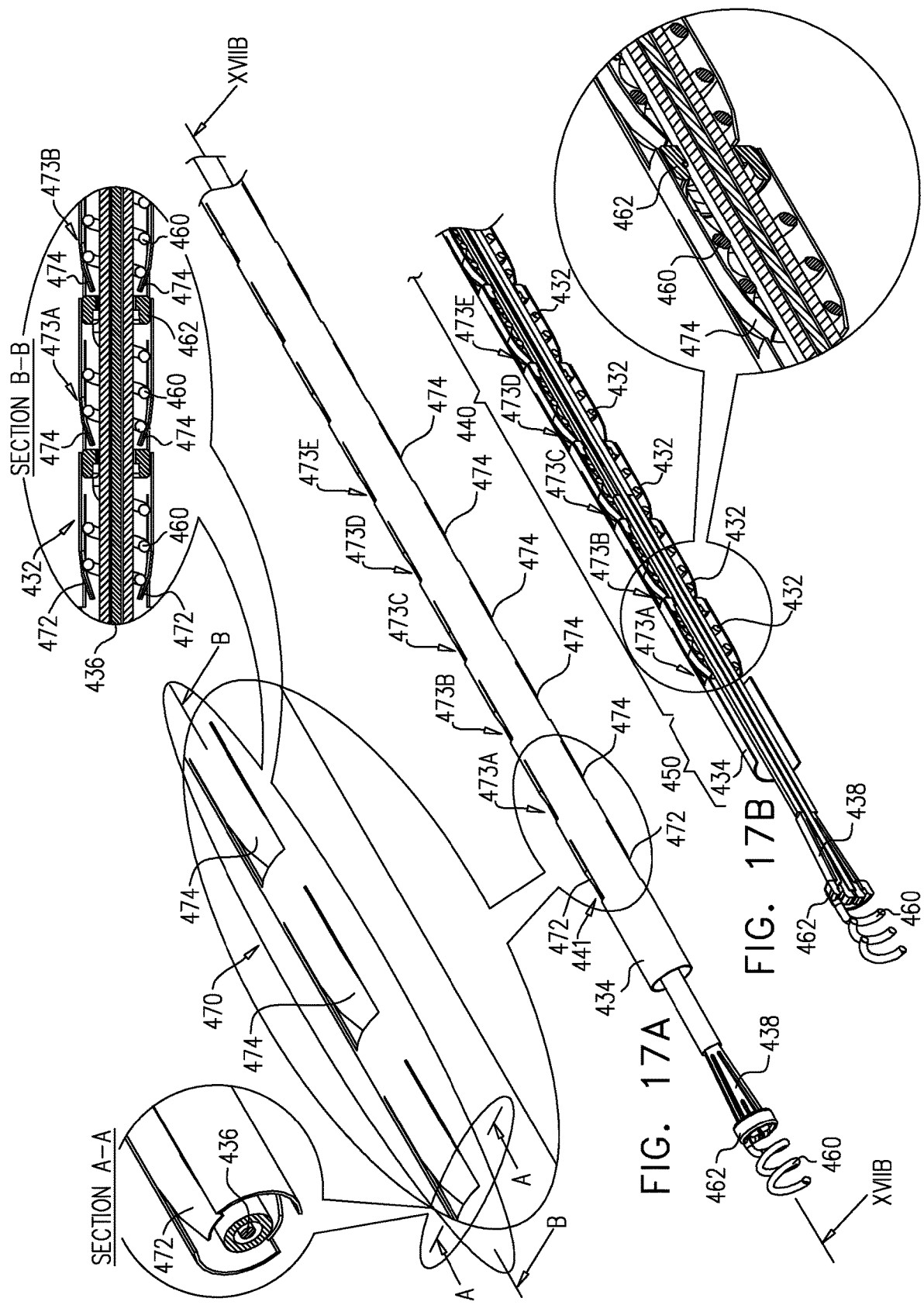

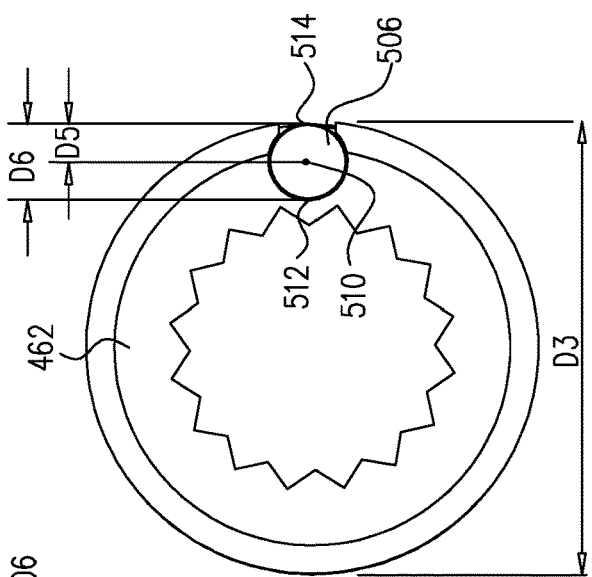
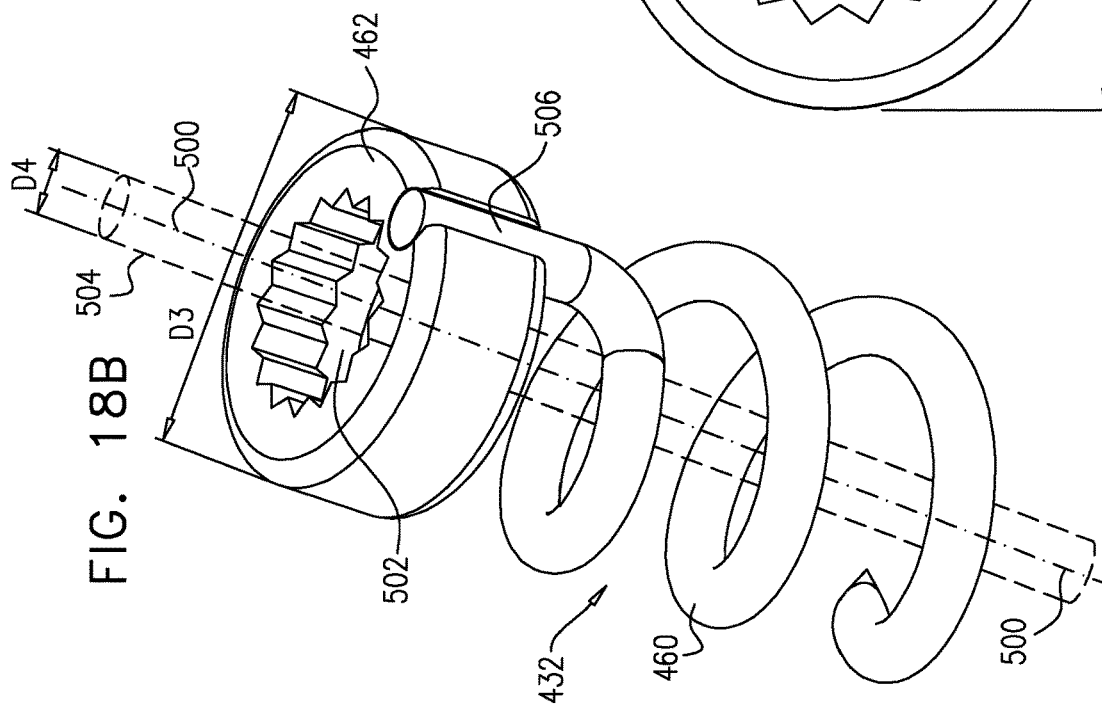
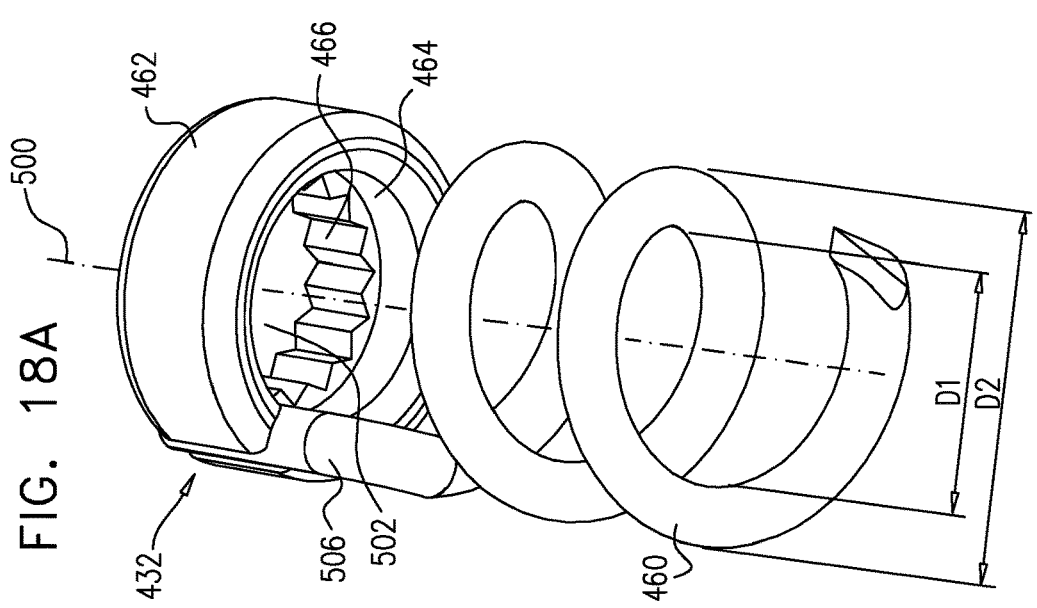

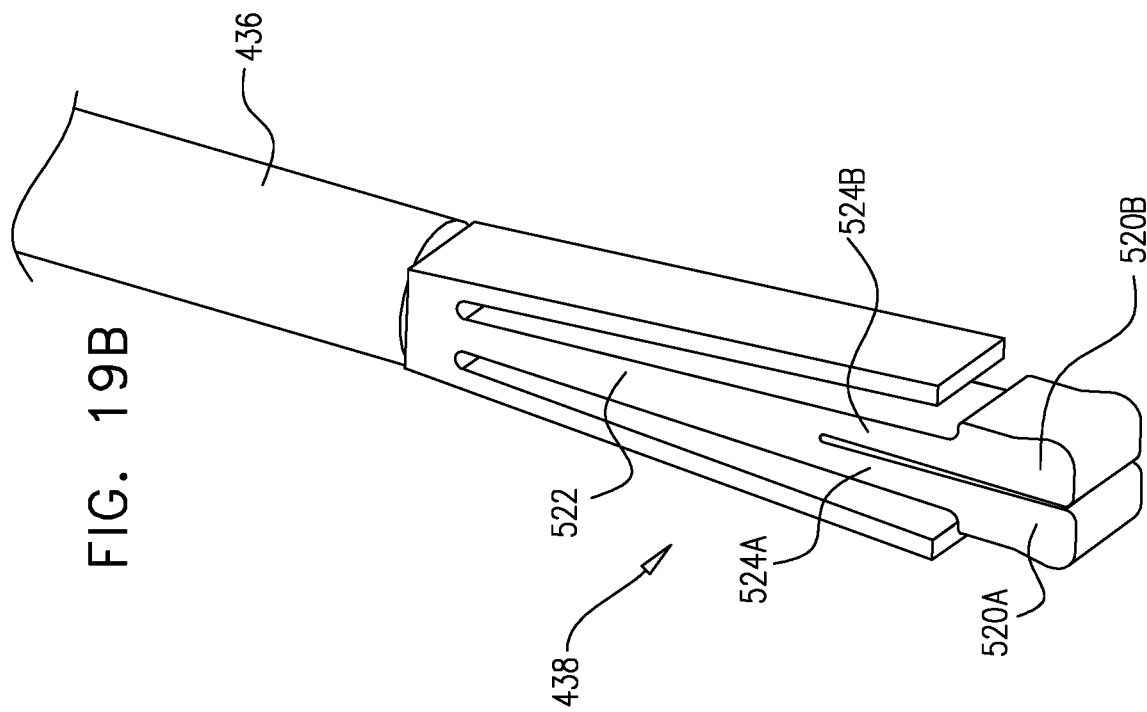
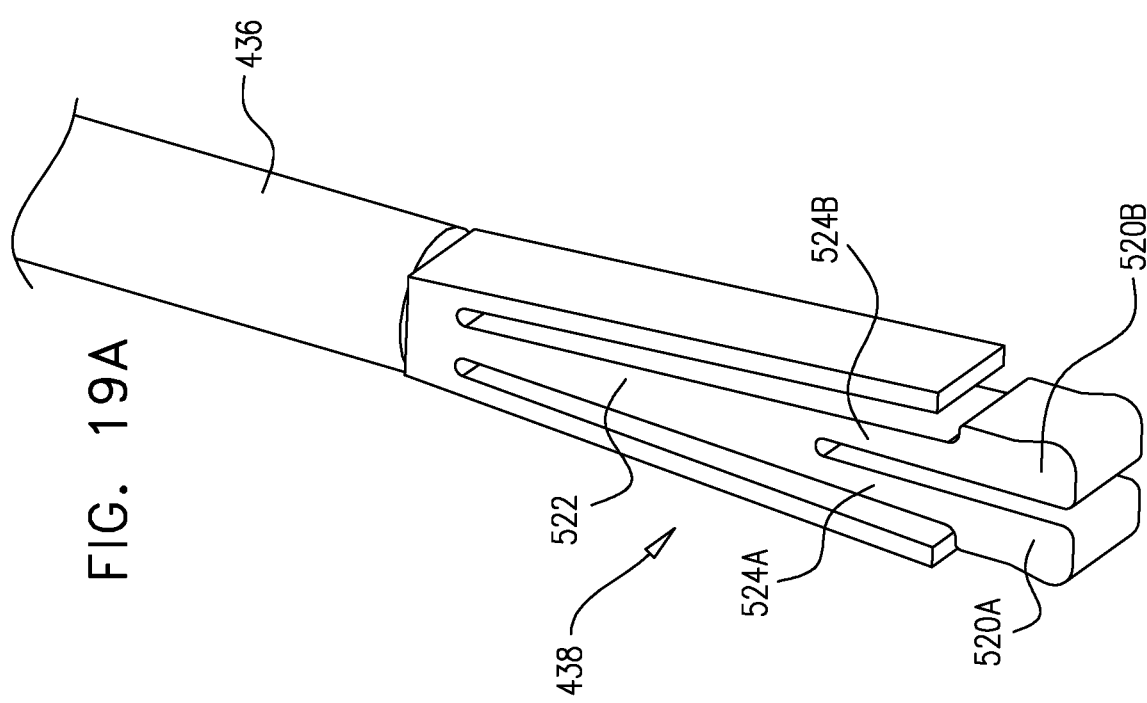

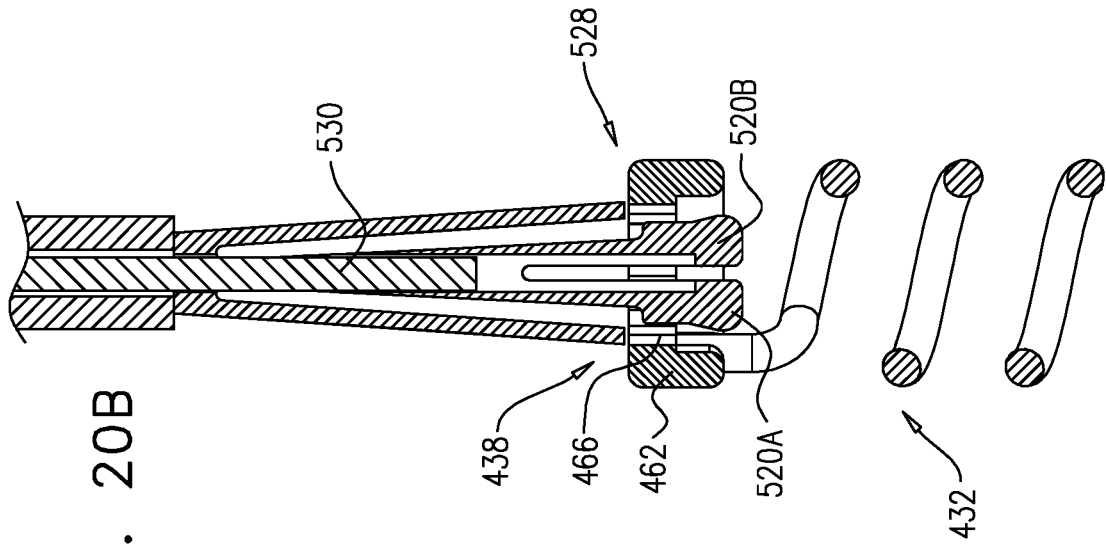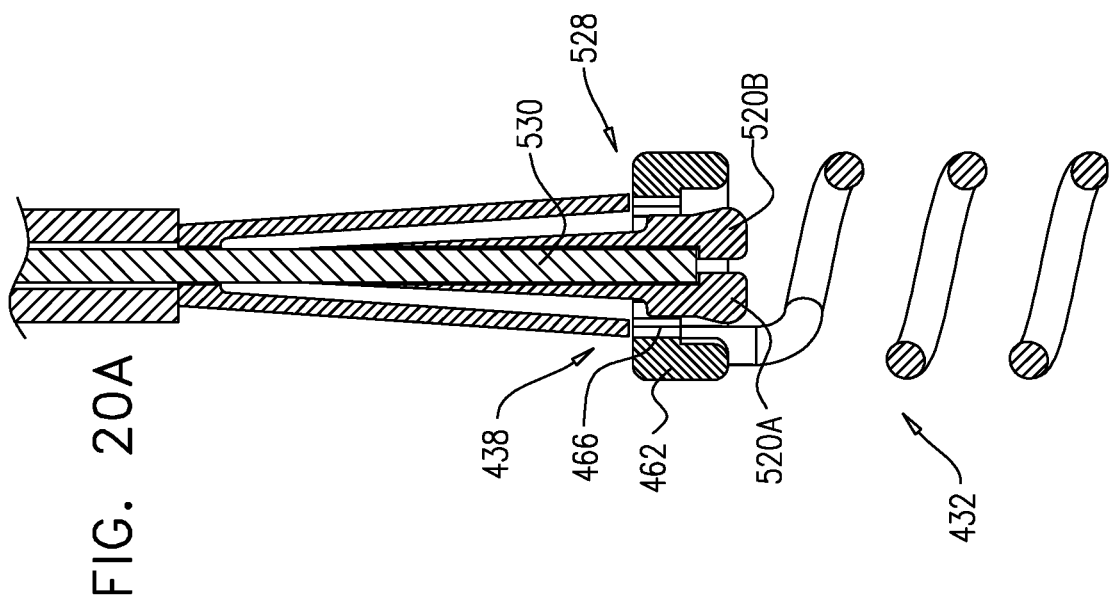

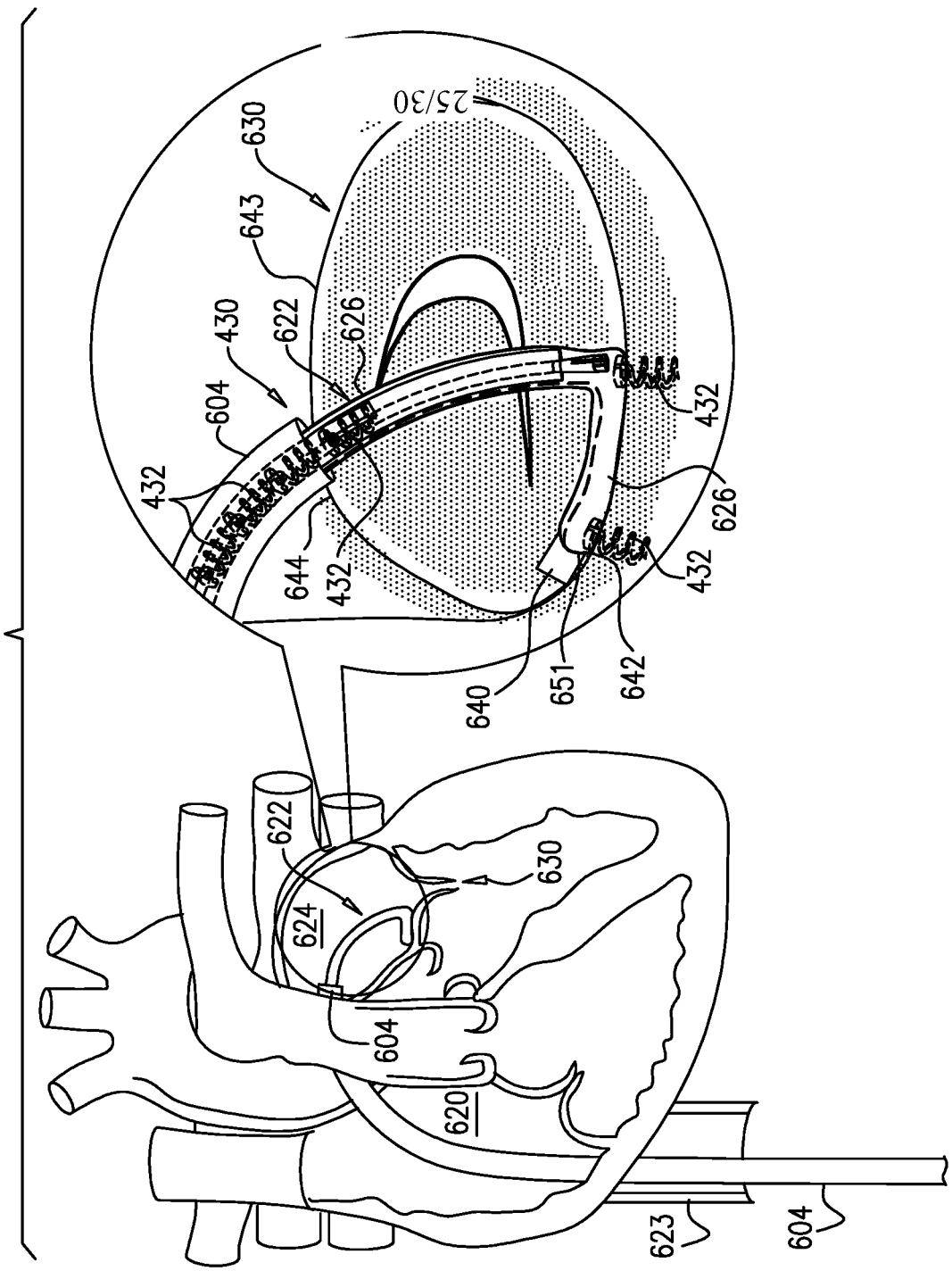

MULTIPLE ANCHOR DELIVERY TOOL

CROSS-REFERENCE TO RELATED APPLICATIONS

The present application is a continuation of U.S. application Ser. No. 14/837,783, filed Aug. 27, 2015, now U.S. Pat. No. 9,937,042, which is a continuation of U.S. application Ser. No. 13/749,153, filed Jan. 24, 2013, now U.S. Pat. No. 9,119,719; and U.S. application Ser. No. 13/749, 153 is
  (a) a continuation-in-part of U.S. application Ser. No. 12/437,103, filed May 7, 2009, now U.S. Pat. No. 8,715,342; and
  (b) a continuation-in-part of International Application No. PCT/IL2011/000600, filed Jul. 26, 2011, which published as PCT Publication WO 2012/014201, which is a continuation-in-part of U.S. application Ser. No. 12/843,412, filed Jul. 26, 2010, now U.S. Pat. No. 8,523,881.

All of the above-mentioned applications are incorporated herein by reference.

FIELD OF THE INVENTION

The present invention relates in general to valve repair, and more specifically to repair of an atrioventricular valve of a patient.

BACKGROUND OF THE INVENTION

Ischemic heart disease causes mitral regurgitation by the combination of ischemic dysfunction of the papillary muscles, and the dilatation of the left ventricle that is present in ischemic heart disease, with the subsequent displacement of the papillary muscles and the dilatation of the mitral valve annulus. Dilation of the annulus of the mitral valve prevents the valve leaflets from fully coapting when the valve is closed. Mitral regurgitation of blood from the left ventricle into the left atrium results in increased total stroke volume and decreased cardiac output, and ultimate weakening of the left ventricle secondary to a volume overload and a pressure overload of the left atrium.

Dilation of the annulus of the mitral valve prevents the valve leaflets from fully coapting when the valve is closed. Mitral regurgitation of blood from the left ventricle into the left atrium results in increased total stroke volume and decreased cardiac output, and ultimate weakening of the left ventricle secondary to a volume overload and a pressure overload of the left atrium.

US Patent Application Publication 2007/0055206 to To et al., which is incorporated herein by reference, describes devices, methods, and kits for deployment of tissue anchors. In some variations, the devices comprise a shaft defining a lumen for housing at least one anchor therein (the anchor having an eyelet) and a mechanism for deploying the anchor distally from the lumen, wherein the inner diameter of the lumen is the same size or smaller than the diameter of the eyelet of the anchor to be disposed therein when the anchor is in an expanded configuration. In some variations, the methods comprise loading an anchor within a lumen of a shaft (where the anchor comprises an eyelet and the shaft has a slot therethrough), passing a linking member through the slot and through the eyelet of the anchor, and deploying the anchor. Other methods comprise loading an anchor within a lumen of a shaft, and deploying the anchor distally from the lumen.

US Patent Application Publication 2007/0080188 to Spence et al., which is incorporated herein by reference, describes systems and methods for securing tissue including the annulus of a mitral valve. The systems and methods may employ catheter based techniques and devices to plicate tissue and perform an annuloplasty. Magnets may be used for guidance in deploying fasteners from a catheter. The fasteners are cinched with a flexible tensile member.

U.S. Pat. No. 6,619,291 to Hlavka et al., which is incorporated herein by reference, describes a minimally invasive method of performing annuloplasty. A method for performing a procedure on a mitral valve of a heart includes inserting an implant into a left ventricle and orienting the implant in the left ventricle substantially below the mitral valve. The implant and tissue around the mitral valve are connected and tension is provided to the implant, in one embodiment, in order to substantially reduce an arc length associated with the mitral valve. In another embodiment, the implant is inserted into the left ventricle through the aorta and the aortic valve.

US Patent Application Publication 2006/0241656 to Starksen et al., which is incorporated herein by reference, describes devices, systems and methods for facilitating positioning of a cardiac valve annulus treatment device, thus enhancing treatment of the annulus. Methods generally involve advancing an anchor delivery device through vasculature of the patient to a location in the heart for treating the valve annulus, contacting the anchor delivery device with a length of the valve annulus, delivering a plurality of coupled anchors from the anchor delivery device to secure the anchors to the annulus, and drawing the anchors together to circumferentially tighten the valve annulus. Devices generally include an elongate catheter having at least one tensioning member and at least one tensioning actuator for deforming a distal portion of the catheter to help it conform to a valve annulus. The catheter device may be used to navigate a subannular space below a mitral valve to facilitate positioning of an anchor delivery device.

US Patent Application Publication 2007/0051377 to Douk et al., which is incorporated herein by reference, describes a catheter-based, annulus reduction device and system for cardiac valve repair and method of using the same. The system is usable for treating mitral valve regurgitation and comprises a catheter, a reduction ring carried within the catheter, the reduction ring including a plurality of exit ports formed in a side wall of the reduction ring and filament received in the reduction ring. The filament includes a plurality of radially extendible barbs corresponding to the sidewall openings. The reduction ring carrying the filament is deployed, adjacent a mitral valve annulus and the filament is translated relative to the reduction ring to deploy the barbs through the exit ports and into the annulus and to further translate the reduction ring with deployed barbs to reshape the annulus.

US Patent Application Publication 2006/0025787 to Morales et al., which is incorporated herein by reference, describes methods and devices that provide constriction of a heart valve annulus to treat cardiac valve regurgitation and other conditions. Embodiments typically include a device for attaching a cinching or tightening apparatus to a heart valve annulus to reduce the circumference of the annulus, thus reducing valve regurgitation. Tightening devices may include multiple tethered clips, multiple untethered crimping clips, stabilizing devices, visualization devices, and the like. In one embodiment, a plurality of tethered clips is secured circumferentially to a valve annulus, and the tether coupling the clips is cinched to reduce the circumference of at least a portion of the annulus. Methods and devices may be used in open heart surgical procedures, minimally invasive procedures, catheter-based procedures, and/or procedures on beating hearts or stopped hearts.

U.S. Pat. No. 7,431,692 to Zollinger et al., which is incorporated herein by reference, describes an adjustable support pad for adjustably holding a tensioning line used to apply tension to a body organ. The adjustable support pad can include a locking mechanism for preventing slidable movement of the tensioning element in one or both directions. The locking mechanism may include spring-loaded locks, rotatable cam-like structures, and/or rotatable spool structures. The adjustable support pad may be formed from rigid, semi-rigid, and/or flexible materials, and may be formed to conform to the outer surface of a body organ. The adjustable support pad can be configured to adjustably hold one or more separate tensioning lines, and to provide for independent adjustment of one or more tensioning lines or groups thereof.

US Patent Application Publication 2007/0016287 to Cartledge et al., which is incorporated herein by reference, describes an implantable device for controlling shape and/or size of an anatomical structure or lumen. The implantable device has an adjustable member configured to adjust the dimensions of the implantable device. The implantable device is housed in a catheter and insertable from a minimally invasive surgical entry. An adjustment tool actuates the adjustable member and provide for adjustment before, during or after the anatomical structure or lumen resumes near normal to normal physiologic function.

US Patent Application Publication 2004/0236419 to Milo, which is incorporated herein by reference, describes methods for reconfiguring an atrioventricular heart valve that may use systems comprising a partial or complete annuloplasty rings proportioned to reconfigure a heart valve that has become in some way incompetent, a pair of trigonal sutures or implantable anchors, and a plurality of staples which may have pairs of legs that are sized and shaped for association with the ring at spaced locations along its length. These systems permit relative axial movement between the staples and the ring, whereby a patient's heart valve can be reconfigured in a manner that does not deter subtle shifting of the native valve components. Shape-memory alloy material staples may have legs with free ends that interlock following implantation. Annuloplasty rings may be complete or partial and may be fenestrated. One alternative method routes a flexible wire, preferably of shape-memory material, through the bights of pre-implanted staples. Other alternative systems use linkers of shape-memory material having hooked ends to interengage with staples or other implanted supports which, following implantation, decrease in effective length and pull the staples or other supports toward one another so as to create desired curvature of the reconfigured valve. These linkers may be separate from the supports or may be integral with them and may have a variety of shapes and forms. Various ones of these systems are described as being implanted non-invasively using a delivery catheter.

US Patent Application Publication 2005/0171601 to Cosgrove et al., which is incorporated herein by reference, describes an annuloplasty repair segment and template for heart valve annulus repair. The elongate flexible template may form a distal part of a holder that also has a proximal handle. Alternatively, the template may be releasably attached to a mandrel that slides within a delivery sheath, the template being released from the end of the sheath to enable manipulation by a surgeon. A tether connecting the template and mandrel may also be provided. The template may be elastic, temperature responsive, or multiple linked segments. The template may be aligned with the handle and form a two- or three-dimensional curve out of alignment with the handle such that the annuloplasty repair segment attached thereto conforms to the curve. The template may be actively or passively converted between its straight and curved positions. The combined holder and ring is especially suited for minimally-invasive surgeries in which the combination is delivered to an implantation site through a small access incision with or without a cannula, or through a catheter passed though the patient's vasculature.

U.S. Pat. No. 6,296,656 to Bolduc et al. describes a helical fastener having a high retentive surface area. The helical fastener has a first end for enhancing penetration into tissue and a second end comprising a coil sectioning a diameter of the fastener for receiving longitudinal and rotational forces. The helical fasteners are attached to body tissue by a fastener applicator having a proximal portion comprising a handle and an actuator and an elongate distal portion for housing a plurality of fasteners. A transferring action of the actuator provides longitudinal and rotational movement of the fasteners out of the distal portion and into body tissue.

U.S. Pat. No. 7,229,452 to Kayan describes a surgical tack for securing a surgical mesh material to body tissue. The tack includes a pair of legs and an arcuate cross-member. A surgical tack applier is also disclosed, for applying the surgical tack. The applier includes an elongate tubular portion having a jacket with a main channel and a pair of longitudinally extending sub-channels. A rotatable drive rod having a helical thread is coupled to the applier, and the sub-channels receive the legs of the tack. The helical thread receives the arcuate cross-member of the surgical tack. Rotation of the drive rod drives the tack from the distal end of the applier.

The following patents and patent application publications, all of which are incorporated herein by reference, may be of interest:

U.S. Pat. No. 5,306,296 to Wright et al.
U.S. Pat. No. 5,674,279 to Wright et al.
U.S. Pat. No. 5,961,539 to Northrup, III et al.
U.S. Pat. No. 6,524,338 to Gundry
U.S. Pat. No. 6,569,198 to Wilson et al.
U.S. Pat. No. 6,602,288 to Cosgrove et al.
U.S. Pat. No. 6,602,289 to Colvin et al.
U.S. Pat. No. 6,689,164 to Seguin
U.S. Pat. No. 6,702,826 to Liddicoat et al.
U.S. Pat. No. 6,718,985 to Hlavka et al.
U.S. Pat. No. 6,764,510 to Vidlund et al.
U.S. Pat. No. 7,004,176 to Lau
U.S. Pat. No. 7,101,395 to Tremulis et al.
U.S. Pat. No. 7,175,660 to Cartledge et al.
U.S. Pat. No. 7,186,262 to Saadat
U.S. Pat. No. 7,686,822 to Shayani
US Patent Application Publication 2002/0087048 to Brock et al.
US Patent Application Publication 2002/0173841 to Ortiz et al.
US Patent Application Publication 2003/0050693 to Quijano et al.
US Patent Application Publication 2003/0167062 to Gambale et al.
US Patent Application Publication 2004/0024451 to Johnson et al.
US Patent Application Publication 2004/0122514 to Fogarty et al.

US Patent Application Publication 2004/0148021 to Cartledge et al.
US Patent Application Publication 2005/0055087 to Starksen
US Patent Application Publication 2005/0288781 to Moaddeb et al.
US Patent Application Publication 2006/0069429 to Spence et al.
US Patent Application Publication 2007/0162111 to Fukamachi et al.
US Patent Application Publication 2007/0255400 to Parravicini et al.
US Patent Application Publication 2008/0004697 to Lichtenstein et al.
PCT Publication WO 01/26586 to Seguin
PCT Publication WO 02/085251 to Hlavka et al.
PCT Publication WO 02/085252 to Hlavka et al.
PCT Publication WO 06/097931 to Gross et al.
PCT Publication WO 07/136783 to Cartledge et al.
PCT Publication WO 08/068756 to Gross et al.
PCT Publication WO 10/004546 to Gross et al.

The following articles, all of which are incorporate herein by reference, may be of interest:

O'Reilly S et al., "Heart valve surgery pushes the envelope," Medtech Insight 8(3): 73, 99-108 (2006)

Dieter R S, "Percutaneous valve repair: Update on mitral regurgitation endovascular approaches to the mitral valve," Applications in Imaging, Cardiac Interventions, Supported by an educational grant from Amersham Health pp. 11-14 (2003)

Swain C P et al., "An endoscopically deliverable tissue-transfixing device for securing biosensors in the gastrointestinal tract," Gastrointestinal Endoscopy 40(6): 730-734 (1994)

Odell J A et al., "Early Results of a Simplified Method of Mitral Valve Annuloplasty," Circulation 92:150-154 (1995)

Brennan, Jennifer, "510(k) Summary of Safety and Effectiveness," January 2008

Odell J A et al., "Early Results of a Simplified Method of Mitral Valve Annuloplasty," Circulation 92:150-154 (1995)

SUMMARY OF THE INVENTION

In some embodiments of the present invention, an adjustable partial annuloplasty ring is provided for repairing a dilated valve annulus of an atrioventricular valve, such as a mitral valve. The annuloplasty ring comprises a flexible sleeve and a plurality of anchors. An anchor deployment manipulator is advanced into a lumen of the sleeve, and, from within the lumen, deploys the anchors through a wall of the sleeve and into cardiac tissue, thereby anchoring the sleeve around a portion of the valve annulus. The anchors are typically deployed from a distal end of the manipulator while the distal end is positioned such that a central longitudinal axis through the distal end of the manipulator forms an angle with a surface of the cardiac tissue of between about 45 and 90 degrees, e.g., between about 75 and 90 degrees, such as about 90 degrees. Typically, the anchors are deployed from the distal end of the manipulator into the cardiac tissue in a direction parallel to the central longitudinal axis through the distal end of the manipulator.

In some embodiments of the present invention, the anchors are deployed from the left atrium into the upper region of the ventricular wall near the atrium, tissue of which generally provides more secure anchoring than does the atrial wall. The above-mentioned angle of deployment enables such deployment into the upper region of the ventricular wall.

In some embodiments of the present invention, the anchor deployment manipulator comprises a steerable outer tube in which is positioned an anchor driver having an elongated, flexible shaft. Rotation of the anchor driver screws the anchors into the cardiac tissue. The anchors may, for example, be helical in shape. For some applications, the plurality of anchors are applied using the manipulator by loading a first one of the anchors onto the anchor driver, and deploying the anchor into the cardiac tissue. The anchor driver is withdrawn from the body of the subject, and a second one of the anchors is loaded onto the anchor driver. The anchor driver is reintroduced into the sleeve of the annuloplasty ring, and the second anchor is deployed. These steps are repeated until all of the anchors have been deployed. Alternatively, the anchor driver is configured to simultaneously hold a plurality of anchors, and to deploy them one at a time.

Typically, the manipulator is gradually withdrawn in a proximal direction during the anchoring procedure as anchors are deployed. The first anchor is thus deployed most distally in the sleeve (generally at or within a few millimeters of the distal tip of the sleeve), and each subsequent anchor is deployed more proximally.

The annuloplasty ring is typically configured to be placed only partially around the valve annulus (i.e., to assume a C-shape), and, once anchored in place, to be contracted so as to circumferentially tighten the valve annulus. To this end, the annuloplasty ring comprises a flexible contracting member such as a wire, which is typically positioned within the lumen of the sleeve. The annuloplasty ring further comprises a contracting mechanism which facilitates contracting of the annuloplasty ring. For some applications, the contracting mechanism comprises a spool to which a first end of the contracting member is coupled. The spool is positioned in a vicinity of either the proximal or the distal end of the sleeve. A second end of the contracting member is coupled to the sleeve in a vicinity of the end of the sleeve opposite the end to which the spool is positioned. Rotation of the spool winds a portion of the contracting member around the spool, thereby pulling the far end of the ring toward the spool and tightening the ring. For some applications, the spool is positioned in a vicinity of the distal end of the sleeve, and is oriented such that a driving interface thereof is accessible from within the sleeve. A screwdriver tool is inserted into the sleeve, and used to rotate the spool via the driving interface of the spool.

All of the tools and elements of the annuloplasty system that are introduced into left atrium are contained within the sleeve of the annuloplasty ring, which reduces the risk that any elements of the system will accidentally be released to the blood circulation, or damage surrounding tissue. In addition, the lumen of the sleeve provides guidance if it should be necessary to return to a previously deployed anchor, such as to tighten, loosen, remove, or relocate the anchor. For some applications, the anchors comprise helical screws, which facilitate such adjusting or removing.

The annuloplasty ring may be advanced toward the annulus of a valve in any suitable procedure, e.g., a transcatheter procedure, a minimally invasive procedure, or an open heart procedure.

In some embodiments of the present invention, an anchor tissue deployment system comprises an anchor deployment tool and a plurality of tissue anchors. The anchor deployment tool comprises a flexible outer tube, a flexible inner shaft, which is positioned within the flexible outer tube, and a rotating deployment element, which is coupled to the distal end of the shaft. The anchor deployment tool is configured to provide an anchor storage area. The storage area initially stores the plurality of tissue anchors, such that the flexible inner shaft passes through channels that pass through each of the anchors, and the anchors are within the flexible outer tube. The rotating deployment element is configured to directly engage the anchors in the anchor storage area one at a time, advance each of the anchors while engaged in a distal direction, and deploy each of the anchors through the distal end of the outer tube and into tissue of a subject. Typically, the anchor deployment tool is configured to provide steering functionality to a distal anchor manipulation area of the anchor deployment tool between the anchor storage area and the distal tube end.

For some applications, the anchor deployment tool is configured such that, as the rotating deployment element advances each of the anchors in the distal direction, only the single anchor currently being advanced is within the distal anchor manipulation area of the anchor deployment tool. For some applications, the anchor deployment tool is configured to deploy each of the anchors into the tissue in a direction parallel to a central longitudinal axis of the outer tube through the distal tube end, and parallel to a central longitudinal axis of the anchor.

For some applications, the rotating deployment element is configured to pass through one or more of the anchors without engaging the anchors when the rotating deployment element is withdrawn in a proximal direction within the outer tube, and to directly engage one of the anchors when the rotating deployment element is advanced in the distal direction against the one of the anchors. Typically, the rotating deployment element is configured to assume a radially-compressed state when passing through the one or more of the anchors without engaging the anchors, and to assume a radially-expanded state when engaging the one of the anchors.

For some applications, the anchor deployment tool further comprises an anchor restraining mechanism in a vicinity of the distal anchor storage end. The mechanism is configured to temporarily restrain at least the distal-most anchor currently stored in the anchor storage area from advancing in the distal direction.

For some applications, each of the anchors comprises a helical tissue coupling element, and a tool-engaging head, fixed to one end of the tissue coupling element. The tool-engaging head is shaped so as to define an engaging opening that is at least partially non-circular, and that passes entirely through the tool-engaging head along the axis. The end of the tissue coupling element is fixed to the tool-engaging head near an outer perimeter of the tool-engaging head, such that the tissue coupling element does not block the engaging opening. The tissue coupling element and the tool-engaging head together define a channel along an entire length of the tissue anchor, which channel is sized and shaped such that a right circular cylinder could be placed within the channel, coaxial with the tissue anchor, and along the entire length of the tissue anchor. The cylinder typically has a diameter of at least 1 mm, such as at least 2 mm.

For some applications, the rotating deployment element is capable of unscrewing an already-deployed anchor from the tissue, withdrawing the anchor in a proximal direction, and subsequently redeploying the anchor into the tissue. For some applications, to enable such redeployment, the rotating deployment element is configured to selectively assume (a) a locked state, in which the rotating deployment element engages one of the anchors, such that the rotating deployment element can withdraw the anchor in the proximal direction, and (b) an unlocked state, in which the rotating deployment element does not engage the anchor.

For some applications, the anchor deployment system is used to deploy anchors for coupling an annuloplasty ring to tissue of a native cardiac valve of the subject, such as a mitral valve. For example, the annuloplasty ring may comprise a sleeve having a lumen, and the anchor deployment tool may be configured to be removably positioned within the lumen of the sleeve, and, while so positioned, to deploy the anchors from the distal tube end through a wall of the sleeve into the tissue. Alternatively applications for the anchor deployment system include delivery anchors via a working channel of an endoscope, such as to mount and secure a support mesh for treating a hernia.

There is therefore provided, in accordance with an embodiment of the present invention, apparatus including an annuloplasty system for use on a subject, which includes:

an annuloplasty ring, which includes a sleeve having a lumen;

at least one anchor, shaped so as to define a coupling head and a tissue coupling element, which tissue coupling element is shaped so as to define a longitudinal axis, and is configured to penetrate cardiac tissue of the subject in a direction parallel to the longitudinal axis; and an anchor deployment manipulator, configured to be removably positioned within the lumen of the sleeve, and, while so positioned, to deploy the tissue coupling element from a distal end of the deployment manipulator through a wall of the sleeve into the cardiac tissue in the direction parallel to the longitudinal axis of the tissue coupling element and parallel to a central longitudinal axis of the deployment manipulator through the distal end of the deployment manipulator.

Typically, the annuloplasty ring includes a partial annuloplasty ring.

For some applications, the coupling element is shaped so as to define a shape selected from the group consisting of: a helix, a spiral, and a screw shaft.

In an embodiment, the annuloplasty ring includes a spool coupled to the sleeve, and a flexible contracting member that is coupled to the spool and the sleeve, such that winding the contracting member around the spool tightens the ring.

In an embodiment, the deployment manipulator includes steering functionality. For some applications, the deployment manipulator includes a tube, which is configured to provide the steering functionality; and an anchor driver, which includes an elongated, flexible shaft which is at least partially positioned within the tube.

In an embodiment, the deployment manipulator is configured to deploy the at least one anchor from the distal end of the deployment manipulator through the wall of the sleeve into the cardiac tissue, while the distal end of the deployment manipulator is positioned such that the central longitudinal axis through the distal end of the deployment manipulator forms an angle of between 45 and 90 degrees with the wall of the sleeve at a point at which the anchor penetrates the wall. For some applications, the point on the wall is a first point on the wall, and the angle is a first angle, the at least one anchor is a first anchor of a plurality of anchors that also includes a second anchor most recently deployed before the first anchor through a second point on the wall, and the deployment manipulator is configured to deploy the first anchor while the distal end of the deployment manipulator is positioned such that the central longitudinal axis forms a second angle of between 45 and 90 degrees with a line defined by the first point and the second point.

For some applications, the apparatus further includes a pusher element which is positioned within the sleeve, and which is configured to, upon being pushed distally, move the distal end of the deployment manipulator proximally within the sleeve by engaging an interior surface of the sleeve.

There is further provided, in accordance with an embodiment of the present invention, a method including:
positioning an anchor deployment manipulator at least partially of a sleeve of an annuloplasty ring;
placing, into an atrium of a subject in a vicinity of an annulus of an atrioventricular valve, at least a portion of the sleeve that contains a distal end of the deployment manipulator; and
deploying at least one anchor from the distal end of the deployment manipulator through a wall of the sleeve such that a coupling element of the anchor enters cardiac tissue of the subject in a direction parallel to a central longitudinal axis of the deployment manipulator through the distal end of the deployment manipulator.

In an embodiment, deploying includes deploying the at least one anchor from the distal end of the deployment manipulator through the wall of the sleeve into the cardiac tissue, while the distal end of the deployment manipulator is positioned such that the central longitudinal axis of the deployment manipulator through the distal end of the deployment manipulator forms an angle of between 45 and 90 degrees with the wall of the sleeve at a point at which the anchor penetrates the wall. For some applications, the point on the wall is a first point on the wall, and the angle is a first angle, the at least one anchor is a first anchor of a plurality of anchors that also includes a second anchor most recently deployed before the first anchor through a second point on the wall, and deploying the first anchor includes deploying the first anchor while the distal end of the deployment manipulator is positioned such that the central longitudinal axis forms a second angle of between 45 and 90 degrees with a line defined by the first point and the second point.

Typically, the annuloplasty ring includes a partial annuloplasty ring, and positioning the deployment manipulator includes positioning the deployment manipulator within the lumen of the partial annuloplasty ring.

In an embodiment, the deployment manipulator includes steering functionality, and placing the sleeve includes steering the deployment manipulator using the steering functionality.

For some applications, deploying the anchor includes deploying the anchor from the atrium into an upper region of a ventricular wall near the atrium.

For some applications, the method further includes positioning a pusher element at least partially within the lumen of the sleeve of the annuloplasty ring; and moving the distal end of the deployment manipulator proximally within the sleeve by pushing the pusher element distally such that the pusher element engages an interior surface of the sleeve.

In an embodiment, the method further includes tightening the annuloplasty ring by winding a flexible contracting member of the ring around a spool coupled to the ring.

There is still further provided, in accordance with an embodiment of the present invention, apparatus including an annuloplasty system for use on a subject, which includes:
an annuloplasty ring, which includes a sleeve having a lumen;
at least one anchor; and
an anchor deployment manipulator, configured to be removably positioned within the lumen of the sleeve, and, while so positioned, to deploy the at least one anchor from a distal end of the deployment manipulator through a wall of the sleeve into cardiac tissue of the subject, while the distal end of the deployment manipulator is positioned such that a central longitudinal axis of the deployment manipulator through the distal end of the deployment manipulator forms an angle of between 45 and 90 degrees with the wall of the sleeve at a point at which the anchor penetrates the wall.

Typically, the annuloplasty ring includes a partial annuloplasty ring.

In an embodiment, the deployment manipulator includes steering functionality.

For some applications, the point on the wall is a first point on the wall, and the angle is a first angle, the at least one anchor is a first anchor of a plurality of anchors that also includes a second anchor most recently deployed before the first anchor through a second point on the wall, and the anchor deployment manipulator is configured to deploy the first anchor while the distal end of the deployment manipulator is positioned such that the central longitudinal axis forms a second angle of between 45 and 90 degrees with a line defined by the first point and the second point.

For some applications, the anchor is shaped so as to define a coupling head and a tissue coupling element, which tissue coupling element is shaped so as to define a longitudinal axis, and is configured to penetrate cardiac tissue of the subject in a direction parallel to the longitudinal axis, and the anchor deployment manipulator is configured to deploy the anchor from the distal end of the deployment manipulator such that the coupling element enters the cardiac tissue in a direction parallel to the central longitudinal axis of the deployment manipulator through the distal end of the deployment manipulator.

For some applications, the anchor is shaped so as to define a coupling head and a tissue coupling element, which is shaped so as to define a shape selected from the group consisting of: a helix, a spiral, and a screw shaft.

There is additionally provided, in accordance with an embodiment of the present invention, a method including:
positioning an anchor deployment manipulator at least partially within a lumen of a sleeve of an annuloplasty ring;
placing, into an atrium of a subject in a vicinity of an annulus of an atrioventricular valve, at least a portion of the sleeve that contains a distal end of the deployment manipulator; and
deploying at least one anchor from the distal end of the deployment manipulator through a wall of the sleeve into cardiac tissue of the subject, while the distal end of the deployment manipulator is positioned such that a central longitudinal axis of the deployment manipulator through the distal end of the deployment manipulator forms an angle of between 45 and 90 degrees with the wall of the sleeve at a point at which the anchor penetrates the wall.

For some applications, deploying includes deploying the at least one anchor while the angle is between 75 and 90 degrees.

In an embodiment, the deployment manipulator includes steering functionality, and placing the sleeve includes steering the deployment manipulator using the steering functionality.

Typically, the annuloplasty ring includes a partial annuloplasty ring, and positioning the anchor deployment manipulator includes positioning the anchor deployment manipulator at least partially within the lumen of the partial annuloplasty ring.

For some applications, the point on the wall is a first point on the wall, and the angle is a first angle, the at least one anchor is a first anchor of a plurality of anchors that also includes a second anchor most recently deployed before the first anchor through a second point on the wall, and deploying the first anchor includes deploying the first anchor while the distal end of the deployment manipulator is positioned such that the central longitudinal axis forms a second angle of between 45 and 90 degrees with a line defined by the first point and the second point.

For some applications, deploying the anchor includes deploying the anchor from the distal end of the deployment manipulator such that a coupling element of the anchor enters the cardiac tissue in a direction parallel to the central longitudinal axis.

For some applications, the anchor is shaped so as to define a coupling head and a tissue coupling element, which is shaped so as to define a shape selected from the group consisting of: a helix, a spiral, and a screw shaft, and deploying the anchor includes screwing the tissue coupling element into the cardiac tissue.

In an embodiment, the method further includes tightening the annuloplasty ring by winding a flexible contracting member of the ring around a spool coupled to the ring.

For some applications, deploying the anchor includes deploying the anchor from the atrium into an upper region of a ventricular wall near the atrium.

For some applications, the deployment manipulator includes an anchor driver positioned within a sheath, the at least one anchor includes a plurality of anchors, and deploying the at least one anchor includes:
  loading a first one of the anchors onto the anchor driver;
  deploying the first one of the anchors through a wall of the sleeve and into the cardiac tissue;
  withdrawing the anchor driver from the sheath and a body of the subject, while leaving the sheath lumen of the sleeve;
  subsequently loading a second one of the anchors onto the anchor driver while the anchor driver is outside the body;
  subsequently reintroducing the anchor driver into the body and the sheath; and
  subsequently deploying the second one of the anchors through the wall of the sleeve into the cardiac tissue.

For some applications, placing the at least a portion of the sleeve includes placing the at least a portion of the sleeve into a right atrium of the subject in a vicinity of a tricuspid valve. Alternatively, placing the at least a portion of the sleeve includes placing the at least a portion of the sleeve into a left atrium of the subject in a vicinity of the annulus of a mitral valve.

There is yet additionally provided, in accordance with an embodiment of the present invention, a method including:
  positioning, during a transcatheter procedure, an anchor deployment manipulator at least partially in an atrium of a subject;
  placing, into the atrium in a vicinity of an annulus of an atrioventricular valve, at least a portion of an annuloplasty ring; and
  coupling the annuloplasty ring to cardiac tissue by deploying at least one anchor from the deployment manipulator in the atrium and into an upper region of a ventricular wall near the atrium.

Typically, the atrioventricular valve is selected from the group consisting of: a mitral valve and a tricuspid valve.

In an embodiment, positioning the anchor deployment manipulator includes positioning at least a distal end of the deployment manipulator within a lumen of a sleeve of the annuloplasty ring, and coupling includes coupling the ring to the cardiac tissue by deploying the at least one anchor from the distal end of the deployment manipulator in the atrium, through a wall of the sleeve, and into the upper region of the ventricular wall. For some applications, deploying the anchor includes deploying the anchor into the upper region of the ventricular wall while the distal end of the deployment manipulator is positioned such that a central longitudinal axis of the deployment manipulator through the distal end of the deployment manipulator forms an angle of between 45 and 90 degrees with the wall of the sleeve at a point at which the anchor penetrates the wall.

For some applications, deploying the anchor includes deploying the anchor from the distal end of the deployment manipulator into the upper region of ventricular wall such that a coupling element of the anchor enters the ventricular wall in a direction parallel to a central longitudinal axis of the deployment manipulator through the distal end of the deployment manipulator.

There is also provided, in accordance with an embodiment of the present invention, apparatus including an annuloplasty system for use on a subject, the system including:
  an annuloplasty ring, which includes a sleeve having a lumen;
  at least one anchor;
  an anchor deployment manipulator, which is configured to be removably positioned within the lumen of the sleeve, and which is configure to deploy the at least one anchor through a wall of the sleeve into cardiac tissue of the subject; and
  a pusher element which is positioned within the sleeve, and which is configured to, upon being pushed distally, move the distal end of the deployment manipulator proximally within the sleeve by engaging an interior surface of the sleeve.

In an embodiment, the deployment manipulator includes an outer tube that is shaped so as to define an opening that is within 3 mm of a distal end of the tube; and an anchor driver that is positioned at least partially within the outer tube, and which is configured to deploy the at least one anchor, and the pusher element is positioned such that a proximal portion thereof is within the outer tube, and a distal portion thereof extends out of the tube through the opening and into the lumen of the sleeve.

In an embodiment, the deployment manipulator includes an outer tube; and an anchor driver that is positioned at least partially within the outer tube, and which is configured to deploy the at least one anchor, and the pusher element is positioned outside of the outer tube.

For some applications, the pusher element is configured to, upon being pushed distally, move the distal end of the deployment manipulator proximally within the sleeve by engaging a distal end of the sleeve. Alternatively or additionally, the pusher element is configured to, upon being pushed distally, move the distal end of the deployment manipulator proximally within the sleeve by engaging the wall of the sleeve.

Typically, the annuloplasty ring includes a partial annuloplasty ring.

In an embodiment, the annuloplasty ring includes a spool coupled to the sleeve, and a flexible contracting member that is coupled to the spool and the sleeve, such that winding the contracting member around the spool tightens the ring.

There is further provided, in accordance with an embodiment of the present invention, a method including:
- positioning an anchor deployment manipulator and a pusher element at east partially within a lumen of a sleeve of an annuloplasty ring;
- placing, into an atrium of a subject in a vicinity of an annulus of an atrioventricular valve, at least a portion of the sleeve that contains a distal end of the deployment manipulator and a distal end of the pusher element;
- moving the distal end of the deployment manipulator proximally within the sleeve by pushing the pusher element distally such that the pusher element engages an interior surface of the sleeve; and
- after moving the distal end of the deployment manipulator, deploying an anchor from the distal end of the deployment manipulator through a wall of the sleeve into cardiac tissue.

For some applications, the deployment manipulator includes an outer tube that is shaped so as to define an opening that is within 3 mm of a distal end of the tube, and positioning the pusher element at least partially within the lumen of the sleeve includes positioning the pusher element such that (a) a distal portion of the pusher element extends out of the tube through the opening and into the lumen of the sleeve, and (b) a proximal portion of the pusher element passes through the tube from the opening to a proximal end of the tube.

For some applications, the deployment manipulator includes an outer tube, and positioning the pusher element at least partially within the lumen of the sleeve includes positioning the pusher element outside of the outer tube.

For some applications, moving includes moving the distal end of the deployment manipulator by pushing the pusher element distally such that the pusher element engages a distal end of the sleeve. Alternatively or additionally, moving includes moving the distal end of the deployment manipulator by pushing the pusher element distally such that the pusher element engages the wall of the sleeve.

For some applications, moving the distal end of the deployment manipulator includes moving the distal end of the deployment manipulator a certain distance by pushing the pusher element the certain distance.

There is still further provided, in accordance with an embodiment of the present invention, apparatus including an annuloplasty ring for use on a subject, which includes:
- a sleeve shaped so as to define a lumen therein that is open at a proximal end of the sleeve;
- a contracting mechanism, coupled to the sleeve in a vicinity of a distal end of the sleeve; and
- an elongated contracting member, a first end of which is coupled to the contracting mechanism, and a second end of which is coupled to the sleeve in a vicinity of the proximal end of the sleeve,
- wherein the contracting mechanism includes a driving interface that is positioned so as to be accessible from within the lumen of the sleeve, and
- wherein the contracting mechanism is configured such that rotation of the driving interface shortens the ring by tightening the elongated contracting member.

Typically, the annuloplasty ring includes a partial annuloplasty ring.

For some applications, the apparatus further includes a screwdriver tool, which includes a head and a shaft, and the screwdriver tool is configured to be removably inserted partially into the lumen of the sleeve via the proximal end of the sleeve, such that the head is removably coupled from within the lumen to the driving interface of the contracting mechanism.

In an embodiment, the apparatus further includes at least one anchor; and an anchor deployment manipulator, configured to be removably positioned within the lumen of the sleeve, and, while so positioned, to deploy the anchor from a distal end of the deployment manipulator through a wall of the sleeve into cardiac tissue of the subject.

There is additionally provided, in accordance with an embodiment of the present invention, a method including:
- coupling a sleeve of an annuloplasty ring to cardiac tissue of a subject at a plurality of sites in a vicinity of an annulus of an atrioventricular valve;
- partially inserting a screwdriver tool into a lumen of the sleeve, the tool having a head and a shaft; and
- rotating the screwdriver tool such that the head, while within the lumen of the sleeve, shortens the ring by rotating a contracting mechanism of the ring that tightens an elongated contracting member coupled to the sleeve.

Typically, the annuloplasty ring includes a partial annuloplasty ring, and coupling includes coupling the sleeve of the partial annuloplasty ring to the cardiac tissue.

There is further provided, in accordance with an application of the present invention, apparatus including:
- a plurality of tissue anchors, which are shaped so as to define respective channels along entire longitudinal lengths of the anchors; and
- an anchor deployment tool, which includes:
  - a flexible outer tube, which has a distal tube end;
  - a flexible inner shaft, which is positioned within the flexible outer tube, and has a distal shaft end; and
  - a rotating deployment element, which is coupled to the distal shaft end,
  - wherein the anchor deployment tool is configured to provide an anchor storage area, which is configured to initially store the plurality of tissue anchors, such that the flexible inner shaft passes through the channels of the anchors, and the anchors are within the flexible outer tube, and
  - wherein the rotating deployment element is configured to directly engage the anchors in the anchor storage area one at a time, advance each of the anchors while engaged in a distal direction, and deploy each of the anchors through the distal tube end and into tissue of a subject.

Typically, the anchor deployment tool is configured such that, as the rotating deployment element advances each of the anchors in the distal direction, only the single anchor currently being advanced is within a distal anchor manipulation area of the anchor deployment tool between the distal anchor storage area end and the distal tube end.

For some applications, the anchor deployment tool is configured to deploy each of the anchors into the tissue in a direction parallel to a central longitudinal axis of the outer tube through the distal tube end, and parallel to a central longitudinal axis of the anchor.

For some applications, the anchor storage area has a distal anchor storage end at a distance of between 1 and 90 cm from the distal tube end, such as between 5 and 25 cm.

For some applications, the anchor deployment tool is configured to provide steering functionality to a distal anchor manipulation area of the anchor deployment tool between the distal anchor storage area end and the distal tube end. For some applications, the flexible outer tube is configured to provide the steering functionality to the distal anchor manipulation area. Alternatively or additionally, the flexible inner shaft is configured to provide the steering functionality to the distal anchor manipulation area.

For some applications, the rotating deployment element is configured to pass through one or more of the anchors without engaging the anchors when the rotating deployment element is withdrawn in a proximal direction within the outer tube, and to directly engage one of the anchors when the rotating deployment element is advanced in the distal direction against the one of the anchors. Typically, the rotating deployment element is configured to assume a radially-compressed state when passing through the one or more of the anchors without engaging the anchors, and to assume a radially-expanded state when engaging the one of the anchors.

For some applications, the anchor deployment tool further includes a spring, which is arranged to apply a distally-directed force to a proximal-most one of the anchors stored within the anchor storage area, which force advances the anchors remaining in the anchor storage area in the distal direction, when the rotating deployment element advances a distal-most one of the anchors out of the anchor storage area in the distal direction. Alternatively, for some applications, the anchor storage area is configured to provide a plurality of anchor storage locations, the anchors are initially stored in respective ones of at least a portion of the anchor storage locations, and when the rotating deployment element advances a distal-most one of the anchors out of the anchor storage area in the distal direction, the anchors remaining in the anchor storage area remain in their respective initial anchor storage locations.

For some applications, the plurality of anchors includes at least 6 anchors.

For some applications, the anchor deployment tool further includes an anchor restraining mechanism in a vicinity of a distal end of the anchor storage area, which mechanism is configured to temporarily restrain at least a distal-most one of the anchors currently stored in the anchor storage area from advancing in the distal direction.

For some applications, each of the anchors has a central longitudinal axis, and includes:
  a helical tissue coupling element, having proximal and distal ends; and
  a tool-engaging head, fixed to the proximal end of the tissue coupling element, which tool-engaging head is shaped so as to define a non-circular engaging opening that passes entirely through the tool-engaging head along the axis,
  wherein the tissue coupling element and the tool-engaging head together define the channel of the tissue anchor along an entire length of the tissue anchor, which channel is sized and shaped such that a right circular cylinder could be placed within the channel, coaxial with the tissue anchor, and along the entire length of the tissue anchor, and
  wherein the rotating coupling element is configured to removably engage the tool-engaging head.

For some applications, the cylinder has a diameter of at least 1 mm, such as at least 2 mm.

For some applications, the apparatus further includes an annuloplasty ring, which includes a sleeve having a lumen, and the anchor deployment tool is configured to be removably positioned within the lumen of the sleeve, and, while so positioned, to deploy the anchors from the distal tube end through a wall of the sleeve into the tissue.

For some applications, the distance between the distal anchor storage end and the distal tube end is between 5 and 25 cm.

For some applications, the anchor deployment tool further includes a hemostasis valve, which includes a distal port to which a proximal end of the flexible outer tube is sealingly coupled. The flexible inner shaft passes through the valve, which maintains a seal around the inner shaft, while allowing the inner shaft to slide distally and proximally through the valve.

For some applications, the rotating deployment element is capable of unscrewing an already-deployed one of the anchors from the tissue, withdrawing the anchor in a proximal direction, and subsequently redeploying the anchor into the tissue.

For some applications, the rotating deployment element includes a locking mechanism that is configured to selectively assume (a) a locked state, in which the locking mechanism, even upon withdrawal of the rotating deployment element in a proximal direction, prevents disengagement of the rotating deployment element from one of the anchors which the rotating deployment element engages, and (b) an unlocked state, in which the locking mechanism does not prevent disengagement of the rotating deployment element from the anchor upon the withdrawal of the rotating deployment element in the proximal direction.

There is further provided, in accordance with an application of the present invention, apparatus including a tissue anchor, which has a central longitudinal axis, and which includes:
  a helical tissue coupling element, having proximal and distal ends; and
  a tool-engaging head, fixed to the proximal end of the tissue coupling element, which tool-engaging head is shaped so as to define a non-circular engaging opening that passes entirely through the tool-engaging head along the axis,
  wherein the tissue coupling element and the tool-engaging head together define a channel along an entire length of the tissue anchor, which channel is sized and shaped such that a right circular cylinder could be placed within the channel, coaxial with the tissue anchor, and along the entire length of the tissue anchor.

For some applications, the cylinder has a diameter of at least 1 mm, such as at least 2 mm.

For some applications, the proximal end of the tissue coupling element is fixed to the tool-engaging head near an outer perimeter of the tool-engaging head, such that the tissue coupling element does not block the engaging opening. For some applications, a distance between (a) a center of the proximal end of the tissue coupling element and (b) the outer perimeter of the tool-engaging head is no more than 30% of a width of the tool-engaging head.

For some applications, a portion of the helical tissue coupling element, at the proximal end which is fixed to the tool-engaging head, is generally straight and oriented at angle of between 0 and 15 degrees with the central longitudinal axis.

There is still further provided, in accordance with an application of the present invention, apparatus including:
  a plurality of tissue anchors; and
  an anchor deployment tool, which (a) is configured to provide an anchor storage area that is configured to initially store the plurality of tissue anchors, and (b) includes a rotating deployment element, which is:
    configured to directly engage the anchors in the anchor storage area one at a time, advance each of the anchors while engaged in a distal direction, and deploy each of the anchors through the distal tube end and into tissue of a subject by screwing the anchor into the tissue, and capable of unscrewing an already-deployed one of the anchors from the tissue, withdrawing the anchor in a proximal direction, and subsequently redeploying the anchor into the tissue.

For some applications, the rotating deployment element includes a locking mechanism that is configured to selectively assume (a) a locked state, in which the locking mechanism, even upon withdrawal of the rotating deployment element in the proximal direction, prevents disengagement of the rotating deployment element from one of the anchors which the rotating deployment element engages, and (b) an unlocked state, in which the locking mechanism does not prevent disengagement of the rotating deployment element from the anchor upon the withdrawal of the rotating deployment element in the proximal direction.

There is additionally provided, in accordance with an application of the present invention, a method including:
providing an anchor deployment tool, which includes a flexible outer tube, a flexible inner shaft, which is positioned within the flexible outer tube, and a rotating deployment element, which is coupled to a distal shaft end of the flexible inner shaft;
providing a plurality of tissue anchors, which are shaped so as to define respective channels along entire longitudinal lengths of the anchors, and which are initially stored within an anchor storage area provided by the anchor deployment tool, such that the flexible inner shaft passes through the channels of the anchors, and the anchors are within the flexible outer tube; and
using the rotating deployment element, directly engaging the anchors in the anchor storage area one at a time, advancing each of the anchors while engaged in a distal direction, and deploying each of the anchors through the distal tube end and into tissue of a subject.

For some applications, advancing each of the anchors includes advancing each of the anchors in the distal direction such that only the single anchor currently being advanced is within a distal anchor manipulation area of the anchor deployment tool between the distal anchor storage area end and the distal tube end.

For some applications, deploying includes deploying each of the anchors into the tissue in a direction parallel to a central longitudinal axis of the outer tube through the distal tube end, and parallel to a central longitudinal axis of the anchor.

For some applications, deploying includes steering a distal anchor manipulation area of the anchor deployment tool between the distal anchor storage area end and the distal tube end.

For some applications, directly engaging, advancing, and deploying the anchors includes directly engaging, advancing, and deploying a first one of the anchors into the tissue at a first site; and, thereafter, directly engaging, advancing, and deploying a second one of the anchors into the tissue at a second site, different from the first site. For some applications, directly engaging the second anchor includes withdrawing the rotating deployment element in a proximal direction within the outer tube, such that the rotating deployment element passes through one or more of the anchors without engaging the anchors; and directly engaging the second anchor by advancing the rotating deployment element in the distal direction against the second anchor. For some applications, withdrawing includes withdrawing the rotating deployment element such that the rotating deployment element assumes a radially-compressed state when passing through the one or more of the anchors without engaging the anchors, and engaging includes engaging the second anchor when the rotating deployment element assumes a radially-expanded state.

For some applications, providing the plurality of anchors includes providing at least 6 anchors.

For some applications, deploying includes deploying each of the anchors into cardiac tissue of the subject. For some applications, deploying includes removably positioning the anchor deployment tool within a lumen of a sleeve of an annuloplasty ring, and, while so positioned, to deploying the anchors from the distal tube end through a wall of the sleeve into the tissue.

For some applications, providing the anchor deployment tool includes providing the anchor deployment tool in which the anchor storage area has a distal anchor storage end at a distance of between 1 and 90 cm from the distal tube end, such as between 5 and 25 cm.

For some applications, the method further includes, using the rotating deployment element, unscrewing an already-deployed one of the anchors from the tissue, withdrawing the anchor in a proximal direction, and subsequently redeploying the anchor into the tissue. For some applications, the rotating deployment element includes a locking mechanism that is configured to selectively assume a locked state, in which the locking mechanism, even upon withdrawal of the rotating deployment element in the proximal direction, prevents disengagement of the rotating deployment element from the anchor, the method further includes causing the locking mechanism to assume the locked state, and withdrawing the anchor includes withdrawing the anchor in the proximal direction while the rotating deployment element is in the locked state.

There is yet additionally provided, in accordance with an application of the present invention, a method including:
providing a tissue anchor having proximal and distal ends, which has a central longitudinal axis, and which includes a helical tissue coupling element, and a tool engaging head, fixed to the proximal end of the tissue coupling element, which tool-engaging head is shaped so as to define a non-circular engaging opening that passes entirely through the tool-engaging head along the axis, wherein the tissue coupling element and the tool-engaging head together define a channel along an entire length of the tissue anchor, which channel is sized and shaped such that a right circular cylinder could be placed within the channel, coaxial with the tissue anchor, and along the entire length of the tissue anchor; and
coupling the tissue anchor to tissue of a subject, by rotating the tissue coupling element into the tissue.

For some applications, a distance between (a) a center of the proximal end of the tissue coupling element and (b) the outer perimeter of the tool-engaging head is no more than 30% of a width of the tool-engaging head, and coupling includes coupling a sheet to the tissue using the tissue anchor, sensing increased resistance to rotation of the tissue coupling element when the sheet resists the rotation, and, responsively the sensed increased resistance, ceasing rotating the tissue coupling element into the tissue.

There is also provided, in accordance with an application of the present invention, a method including:
providing a plurality of tissue anchors;
providing an anchor deployment tool, which (a) is configured to provide an anchor storage area, which is configured to initially store the plurality of tissue anchors, and (b) includes a rotating deployment element;

using the rotating deployment element, directly engaging the anchors in the anchor storage area one at a time, advancing each of the anchors while engaged in a distal direction, and deploying each of the anchors through the distal tube end and into tissue of a subject by screwing the anchor into the tissue; and subsequently, using the rotating deployment element, unscrewing an already-deployed one of the anchors from the tissue, withdrawing the anchor in a proximal direction, and subsequently redeploying the anchor into the tissue.

For some applications, the rotating deployment element includes a locking mechanism that is configured to selectively to assume a locked state, in which the locking mechanism, even upon withdrawal of the rotating deployment element in the proximal direction, prevents disengagement of the rotating deployment element from the anchor, the method further includes causing the locking mechanism to assume the locked state, and withdrawing the anchor includes withdrawing the anchor in the proximal direction while the rotating deployment element is in the locked state.

The present invention will be more fully understood from the following detailed description of embodiments thereof, taken together with the drawings, in which:

BRIEF DESCRIPTION OF THE DRAWINGS

FIGS. 1A and 1B are schematic illustrations of an adjustable partial annuloplasty ring in a non-contracted state, in accordance with respective embodiments of the present invention;

FIG. 2 is a schematic longitudinal cross-sectional illustration of an anchor deployment manipulator, in accordance with an embodiment of the present invention;

FIG. 3 is a schematic longitudinal cross-sectional illustration of the anchor deployment manipulator of FIG. 2 advanced into the annuloplasty ring of FIG. 1A, in accordance with an embodiment of the present invention;

FIG. 4 is a schematic cross-sectional illustration of the anchor deployment manipulator of FIG. 2 advanced into the annuloplasty ring of FIG. 1A or 1B, taken along section IV-IV of FIG. 3, in accordance with an embodiment of the present invention;

FIGS. 5A-B are schematic illustrations of a screwdriver tool being used to rotate a spool of a contracting mechanism of the rings of FIGS. 1A and 1B, respectively, in accordance with respective embodiments of the present invention;

FIGS. 6A-I are schematic illustrations of a procedure for implanting the annuloplasty ring of FIG. 1A to repair a mitral valve, in accordance with an embodiment of the present invention;

FIG. 8 is a schematic illustration of the system of FIGS. 1-4 comprising a flexible pusher element, in accordance with an embodiment of the present invention;

FIG. 9 is a schematic illustration of a pusher tube applied to a proximal end of the sleeve of FIGS. 1-4, in accordance with an embodiment of the present invention;

FIGS. 10 and 11 are schematic illustrations of the system of FIGS. 1-4 comprising a steerable tube, in accordance with respective embodiments of the present invention;

FIGS. 13A-B are schematic illustrations of an anchor deployment system, in accordance with an application of the present invention;

FIGS. 14 and 15A-B are schematic illustrations showing the assembly of components of the anchor deployment system of FIGS. 13A-B, in accordance with an application of the present invention;

FIGS. 16A-D are schematic illustrations of the deployment of a single anchor into tissue using an anchor deployment tool of the anchor deployment system of FIGS. 13A-B, in accordance with an application of the present invention;

FIGS. 17A-B are schematic illustrations of an alternative configuration of the anchor deployment system of FIGS. 13A-B, in accordance with an application of the present invention;

FIGS. 18A-C are schematic illustrations of an anchor of the anchor deployment system of FIGS. 13A-B from three different views, in accordance with an application of the present invention;

FIGS. 19A and 19B are schematic illustrations of a rotating deployment element of the anchor deployment system of FIGS. 13A-B in radially-expanded and radially-compressed states, respectively, in accordance with an application of the present invention;

FIGS. 20A and 20B are schematic illustrations of the rotating deployment element of FIGS. 19A-B engaging a tool-engaging head of the anchor of FIGS. 18A-C, with the element in locked and unlocked states, respectively, in accordance with an application of the present invention; and FIGS. 21A-I are schematic illustrations of a procedure for implanting an annuloplasty ring to repair a mitral valve, in accordance with an application of the present invention.

DETAILED DESCRIPTION OF EMBODIMENTS

Figure 6A:
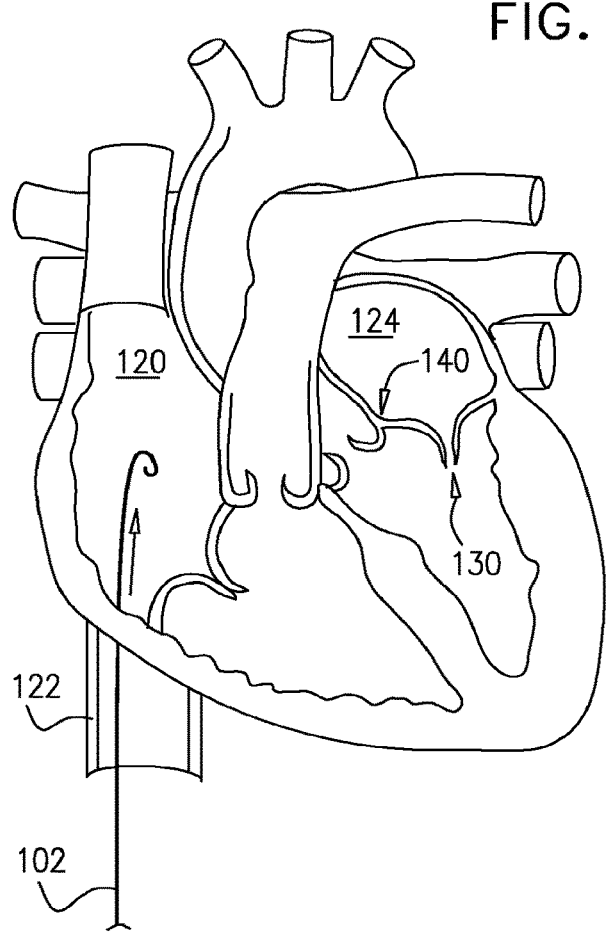

FIGS. 1-4 are schematic illustrations of a system 20 for repairing a dilated atrioventricular valve, such as a mitral valve, in accordance with an embodiment of the present invention. System 20 comprises an adjustable partial annuloplasty ring 22, shown alone in FIGS. 1A and 1B in a non-contracted state, and an anchor deployment manipulator 24, shown alone in FIG. 2. Annuloplasty ring 22 comprises a flexible sleeve 26. Anchor deployment manipulator 24 is advanced into sleeve 26, as shown in FIGS. 3 and 4, and, from within the sleeve, deploys anchors 38 through a wall of the sleeve into cardiac tissue, thereby anchoring the ring around a portion of the valve annulus.

FIGS. 1A and 1B are schematic illustration of annuloplasty ring 22 in a non-contracted state, in accordance with respective embodiments of the present invention. Sleeve 26 is typically configured to be placed only partially around the valve annulus (i.e., to assume a C-shape), and, once anchored in place, to be contracted so as to circumferentially tighten the valve annulus. Alternatively, the ring is configured to be placed entirely around the valve annulus. In order to tighten the annulus, annuloplasty ring 22 comprises a flexible elongated contracting member 30 that extends along the ring.

Annuloplasty ring 22 further comprises a contracting mechanism 40, which facilitates contracting of the annuloplasty ring. Contracting mechanism 40 is described in more detail hereinbelow. In addition, the ring comprises a plurality of anchors 38, typically between about 5 and about 20 anchors, such as about 10 or about 16 anchors. In FIGS. 1A and 1B, anchors 38 are shown prior to their insertion into ring 22, while in FIG. 3 one of the anchors is shown deployed through the wall of sleeve 26, and a second one of the anchors is shown during deployment by anchor deployment manipulator 24. The insertion of the anchors into the sleeve and deployment of the anchors into cardiac tissue is described in detail hereinbelow.

Flexible sleeve 26 may comprise a braided, knitted, or woven mesh or a tubular structure comprising ePTFE. For some applications, the braid comprises metal and fabric fibers. The metal fibers, which may comprise Nitinol for example, may help define the shape of the sleeve, e.g., hold the sleeve open to provide space for passage and manipulation of deployment manipulator 24 within the sleeve. The fabric fibers may promote tissue growth into the braid. Optionally, the sleeve is somewhat elastic, which gives the sleeve a tendency to longitudinally contract, thereby helping tighten the sleeve. For example, the sleeve may be bellows- or accordion-shaped.

Typically, the sleeve is configured to have a tendency to assume a straight shape. This straightness helps the surgeon locate the next site for each subsequent anchor during the implantation procedure, as described hereinbelow with reference to FIGS. 6A-I. For example, because the sleeve assumes a generally straight shape, the sleeve may help provide an indication of distance between adjacent anchoring sites.

For some applications, the sleeve is configured to have a controllably variable stiffness. For example, a somewhat stiff wire may be placed in the sleeve to provide the stiffness, and subsequently be removed at the conclusion of the implantation procedure when the stiffness is no longer useful.

Elongated contracting member 30 comprises a wire, a ribbon, a rope, or a band, which typically comprises a flexible and/or superelastic material, e.g., nitinol, polyester, stainless steel, or cobalt chrome. In some embodiments, contracting member 30 comprises a braided polyester suture (e.g., Ticron). In some embodiments, contracting member 30 is coated with polytetrafluoroethylene (PTFE). In some embodiments, contracting member 30 comprises a plurality of wires that are intertwined to form a rope structure.

For some applications, contracting member 30 is positioned at least partially within a lumen of the sleeve 26, such as entirely within the lumen (as shown in FIGS. 1A-B, 5A-B, 6H, and 6I). For some applications in which the contracting member is positioned partially within the lumen, the contracting member is sewn into the wall of the sleeve, such that the contracting member is alternatingly inside and outside of the sleeve along the length of the sleeve (as shown in FIGS. 3, 8, and 9). Optionally, sleeve 26 defines an internal channel within which member 30 is positioned (configuration not shown). Alternatively, the contracting member is disposed outside the lumen of the sleeve, such as alongside an outer wall of the sleeve. For example, sleeve 26 may define an external channel within which member 30 is positioned, or the sleeve may comprise or be shaped so as to define external coupling elements, such as loops or rings (configuration not shown). For some applications, contracting member 30 is positioned approximately opposite the anchors.

In an embodiment of the present invention, contracting mechanism 40 comprises a housing 44 which houses a spool 46, i.e., a rotatable structure, to which a first end 47 of contracting member 30 is coupled. Spool 46 is positioned in a vicinity of (e.g., within 1 cm of) either a distal end 51 of sleeve 26, as shown in FIGS. 1A and 3, or a proximal end 49 of sleeve 26, as shown in FIG. 1B. A second end 53 of contracting member 30 is coupled to the sleeve in a vicinity of (e.g., within 1 cm of) the end of the sleeve opposite the end to which the spool is positioned. In the configuration shown in FIGS. 1A and 3, second end 53 of contracting member 30 is coupled to the sleeve in a vicinity of proximal end 49 of the sleeve, while in the configuration shown in FIG. 1B, the second end of the contracting member is coupled to the sleeve in a vicinity of distal end 51 of the sleeve. Rotation of spool 46 winds a portion of the contracting member around the spool, thereby pulling the far end of the ring toward the spool and shortening and tightening the ring.

Alternatively, in some configurations, spool 46 is positioned at an intermediary position along the sleeve, rather than in a vicinity of one of the ends. For these configurations, contracting member 30 comprises two contracting members, which are respectively connected to the two ends of the sleeve, and both of which are connected to the spool. Rotating the spool contracts both contracting members. These configurations may be implemented using techniques described in U.S. patent application Ser. No. 12/341,960 to Cabiri, which published as US Patent Application Publication 2010/0161047 and is incorporated herein by reference, with reference to FIG. 15 thereof.

Spool 46 is shaped to provide a hole 42 or other coupling mechanism for coupling first end 47 of contracting member 30 to the spool, and thereby to contracting mechanism 40. Spool 46 is shaped to define a driving interface 48. For some applications, driving interface 48 is female. For example, the interface may be shaped to define a channel which extends through the cylindrical portion of spool 46 from an opening provided by an upper surface 50 of spool 46 to an opening provided by a lower surface 52 of spool 46. Alternatively, driving interface 48 is shaped so as to define an indentation (e.g., a groove) that does not extend entirely through the cylindrical portion of the spool. Further alternatively, driving interface 48 is male, and defines a protrusion, e.g., a hexagonal head or a head having another shape.

A distal portion of a screwdriver tool 80, which is described hereinbelow with reference to FIGS. 5A-B, engages spool 46 via driving interface 48 and rotates spool 46 in response to a rotational force applied to the screwdriver. The rotational force applied to the screwdriver tool rotates spool 46 via the portion of the screwdriver tool that engages driving interface 48 of spool 46.

Spool 46 typically comprises a locking mechanism that prevents rotation of the spool after contracting member 30 has been tightened. For example, locking techniques may be used that are described with reference to FIG. 4 of above-mentioned U.S. application Ser. No. 12/341,960 to Cabiri.

Alternatively, in an embodiment of the present invention, contracting mechanism 40 is configured to tighten contracting member 30, crimp the contracting member to hold the contracting member taut, and subsequently cut the excess length of the contracting member.

FIG. 2 is a schematic longitudinal cross-sectional illustration of anchor deployment manipulator 24, FIG. 3 is a schematic longitudinal cross-sectional illustration of the anchor deployment manipulator advanced into annuloplasty ring 22, and FIG. 4 is a schematic cross-sectional illustration of the anchor deployment manipulator advanced into the annuloplasty ring, taken along section IV-IV of FIG. 3, in accordance with an embodiment of the present invention. Anchor deployment manipulator 24 is advanced into a lumen of sleeve 26, and, from within the lumen, deploys anchors 38 through a wall of the sleeve and into cardiac tissue, thereby anchoring the sleeve around a portion of the valve annulus. Typically, annuloplasty ring 22 and anchor deployment manipulator 24 are introduced into the heart via a sheath 104, as described hereinbelow with reference to FIGS. 6A-I.

In an embodiment of the present invention, at least one of anchors 38 is deployed from a distal end 60 of manipulator 24 while the distal end is positioned such that a central longitudinal axis 62 through distal end 60 of manipulator 24 forms an angle α (alpha) of between about 45 and 90 degrees with the wall of sleeve 26 at the point at which the anchor penetrates the wall, such as between about 75 and 90 degrees, e.g., about 90 degrees. (In FIG. 3, a line 64 schematically illustrates the plane tangential to the wall of the sleeve at the anchor-penetration point.) This anchor-penetration point is typically at a portion of the sleeve that extends distally beyond the distal end of outer tube 66 of deployment manipulator 24 (which is described hereinbelow), i.e., that is no longer in contact with the outer surface of outer tube 66. Typically, all of the anchors are deployed at such angles, with the possible exception of the first anchor deployed near the distal end of the sleeve.

For some applications, at least one of anchors 38 is deployed from distal end 60 of manipulator 24 while distal end 60 is positioned such that longitudinal axis 62 through distal end 60 of manipulator 24 forms an angle (beta) of between about 45 and 90 degrees (such as between about 75 and 90 degrees, e.g., about 90 degrees) with a line 65 defined by (a) a first point 67 at which the anchor currently being deployed penetrates the wall of the sleeve and (b) a second point 69 at which a most recently previously deployed anchor penetrates the wall of sleeve 26. Typically, all of the anchors are deployed at such angles, with the exception of the first anchor deployed near the distal end of the sleeve.

Typically, the anchors are deployed from distal end 60 of manipulator 24 into the cardiac tissue in a direction parallel to central longitudinal axis 62.

In an embodiment of the present invention, anchor deployment manipulator 24 comprises an outer tube 66 and an anchor driver 68 which is at least partially positioned within tube 66. Anchor driver 68 comprises an elongated, flexible shaft 70, having at its distal end a driver head 72. Rotation of the anchor driver screws the anchors into the cardiac tissue. Each of anchors 38 is shaped so as to define a coupling head 74 and a tissue coupling element 76. The anchors are typically rigid. Tissue coupling elements 76 may, for example, be helical or spiral in shape (e.g., having the shape of a corkscrew), as shown in the figures, may comprises screws, or may have other shapes. Coupling heads 74 may be either male (e.g., a hex or square protrusion) or female (e.g., a straight slot, a hex opening, a Phillips opening, or a Robertson opening). The use of helical anchors, which are screwed into the cardiac tissue, generally minimizes the force that needs to be applied during deployment of the anchors into the cardiac tissue. Alternatively, the anchors may comprise staples, clips, spring-loaded anchors, or other tissue anchors described in the references incorporated hereinabove in the Background section, or otherwise known in the art. For some applications, outer tube 66 of deployment manipulator 24 is steerable, as known in the catheter art, while for other applications, a separate steerable tube is provided, as described hereinbelow with reference to FIG. 10 or FIG. 11. To provide steering functionality to deployment manipulator, outer tube 66, steerable tube 300 (FIG. 10), or steerable tube 320 (FIG. 11), as the case may be, typically comprises one or more steering wires, the pulling and releasing of which cause deflection of the distal tip of the tube.

In an embodiment of the present invention, each of tissue coupling elements 76 is shaped so as to define a longitudinal axis 78 (shown in FIGS. 1A-B), and is configured to penetrate the cardiac tissue in a direction parallel to longitudinal axis 78. Deployment manipulator 24 is configured to deploy tissue coupling element 76 from distal end 60 of the manipulator through the wall of sleeve 26 in a direction parallel to longitudinal axis 78 and parallel to central longitudinal axis 62 through distal end 60 of deployment manipulator 24 (shown in FIGS. 2, 3, and 7-10).

For some applications, the plurality of anchors are applied using the manipulator by loading a first one of the anchors onto the anchor driver, and deploying the anchor into the cardiac tissue. The anchor driver is withdrawn from the subject's body (typically while leaving outer tube 66 of the deployment manipulator in place in the sleeve), and a second one of the anchors is loaded onto the anchor driver. The anchor driver is reintroduced into the outer tube of the manipulator, and the second anchor is deployed. These steps are repeated until all of the anchors have been deployed. Alternatively, the entire deployment manipulator, including the anchor driver, is removed from the body and subsequently reintroduced after being provided with another anchor. Further alternatively, the deployment manipulator is configured to simultaneously hold a plurality of anchors, and to deploy them one at a rime (configuration not shown).

Typically, the first anchor 38 is deployed most distally in sleeve 26 (generally at or within a few millimeters of a distal end 51 of the sleeve), and each subsequent anchor is deployed more proximally, such that manipulator 24 is gradually withdrawn in a proximal direction during the anchoring procedure.

Reference is now made to FIGS. 5A-B, which are schematic illustrations of screwdriver tool 80 being used to rotate spool 46 of contracting mechanism 40 of ring 22, in accordance with respective embodiments of the present invention. Screwdriver tool 80 has a head 82 that is either male (e.g., comprising a screwdriver head, having, such as a slot-head, an Allen-head, a Phillips-head, a Robertson-head, or a hex-head) or female (e.g., comprising a wrench head, having, for example, a square or hex opening), as appropriate for the driving interface provided. Typically, the screwdriver tool comprises a shaft 84, at least a portion of which is flexible. For some applications, the screwdriver tool is used that is described in above-referenced U.S. patent application Ser. No. 12/341,960, with reference to FIG. 4 thereof. Alternatively, anchor driver 68 of deployment manipulator 24 serves as screwdriver tool 80, and is used to rotate the spool, in which case driving interface 48 is appropriately shaped to receive driver head 72 of anchor driver 68.

In the configuration shown in FIG. 5A, contracting member 30 is coupled to distal end 51 of sleeve 26, as shown hereinabove in FIGS. 1A and 3. Contracting mechanism 40 is oriented such that driving interface 48 thereof is accessible from within sleeve 26. Screwdriver tool 80 is inserted into sleeve 26, and used to rotate spool 46 via the driving interface. Alternatively, anchor driver 68 of deployment manipulator 24 serves as screwdriver tool 80, and is used to rotate the spool, in which case driving interface 48 is appropriately shaped to engage driver head 72 of anchor driver 68. In either case, the sleeve thus serves to guide the screwdriver tool to driving interface 48. For some applications, an interior surface of the sleeve is tapered near the distal end of the sleeve, to help guide the screwdriver head to the driving interface. For some applications, during the implantation procedure, anchor deployment manipulator 24 is left slightly inserted into proximal end 49 of sleeve 26 after all of anchors 38 have been deployed, in order to facilitate passage of screwdriver tool 80 into sleeve 26.

In the configuration shown in FIG. 5B, access to driving interface 48 is provided from outside sleeve 26. For some applications, contracting mechanism 40 comprises a wire 86 that is attached to the mechanism and passes out of the body of the subject, typically via sheath 104. In order to readily bring the screwdriver tool to driving interface 48, screwdriver tool 80 is guided over (as shown) the wire, or alongside the wire (configuration not shown).

For some applications, contracting mechanism 40 is positioned in a vicinity of e.g., within 1 cm of) distal end 51 of sleeve 26, and access to driving interface 48 is provided from outside sleeve 26, as described with reference to FIG. 5B (in which the contracting mechanism is positioned in a vicinity of proximal end 49 of the sleeve).

For some applications in which access to driving interface 48 is provided from outside sleeve 26, the screwdriver tool is initially removably attached to the driving interface, prior to the commencement of the implantation procedure, and is subsequently decoupled from the driving interface after spool 46 has been rotated. In these applications, contracting mechanism 40 may be positioned in a vicinity of distal end 51 or proximal end 49 of sleeve 26, or at an intermediate location along the sleeve. Optionally, at least a portion of a shaft of the screwdriver tool is positioned within sheath 104, which is described hereinbelow with reference to FIGS. 6A-I.

Reference is now made to FIGS. 6A-I, which are schematic illustrations of a procedure for implanting annuloplasty ring 22 to repair a mitral valve 130, in accordance with an embodiment of the present invention. The procedure is typically performed with the aid of imaging, such as fluoroscopy, transesophageal echo, and/or echocardiography.

The procedure typically begins by advancing a semi-rigid guidewire 102 into a right atrium 120 of the patient, as shown in FIG. 6A.

Figure 6B:
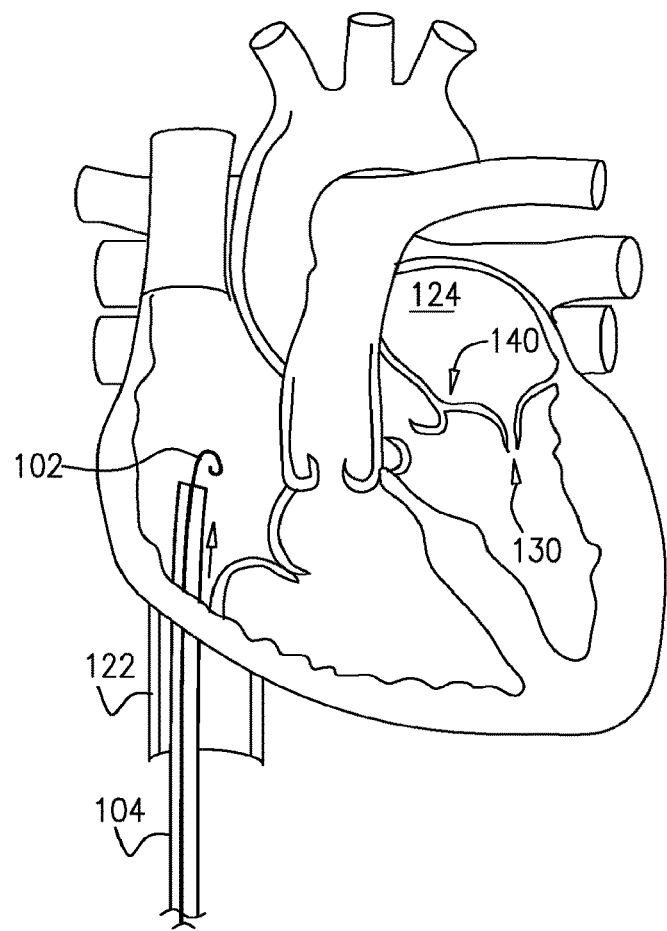
Figure 6C:
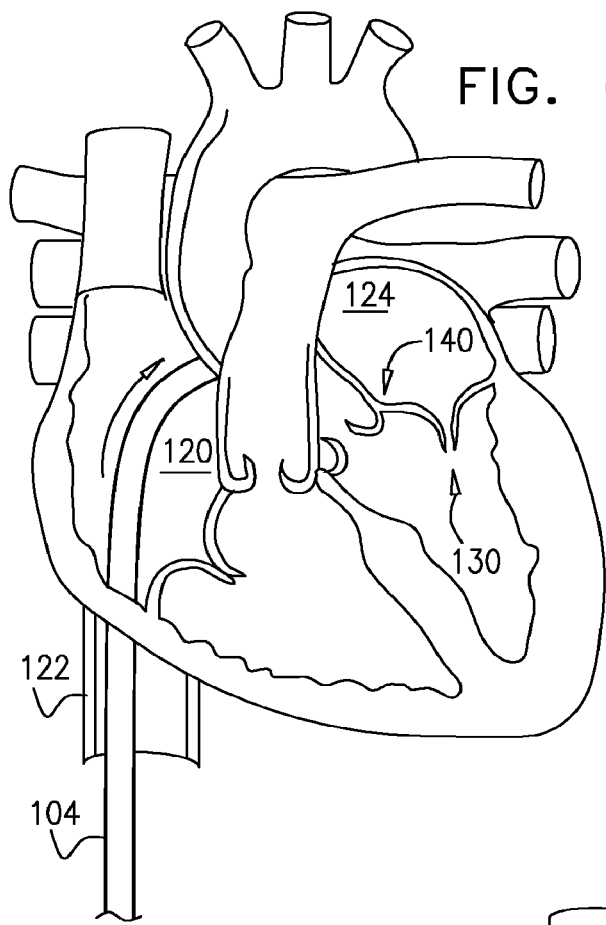

As show in FIG. 6B, guidewire 102 provides a guide for the subsequent advancement of a sheath 104 therealong and into the right atrium. Once sheath 104 has entered the right atrium, guidewire 102 is retracted from the patient's body. Sheath 104 typically comprises a 14-20 F sheath, although the size may be selected as appropriate for a given patient. Sheath 104 is advanced through vasculature into the right atrium using a suitable point of origin typically determined for a given patient. For example:

sheath 104 may be introduced into the femoral vein of the patient, through an inferior vena cava 122, into right atrium 120, and into a left atrium 124 transseptally, typically through the fossa ovalis;

sheath 104 may be introduced into the basilic vein, through the subclavian vein to the superior vena cava, into right atrium 120, and into left atrium 124 transseptally, typically through the fossa ovalis; or sheath 104 may be introduced into the external jugular vein, through the subclavian vein to the superior vena cava, into right atrium 120, and into left atrium 124 transseptally, typically through the fossa ovalis.

In an embodiment of the present invention, sheath 104 is advanced through an inferior vena cava 122 of the patient (as shown) and into right atrium 120 using a suitable point of origin typically determined for a given patient.

Sheath 104 is advanced distally until the sheath reaches the interatrial septum.

Figure 6D:
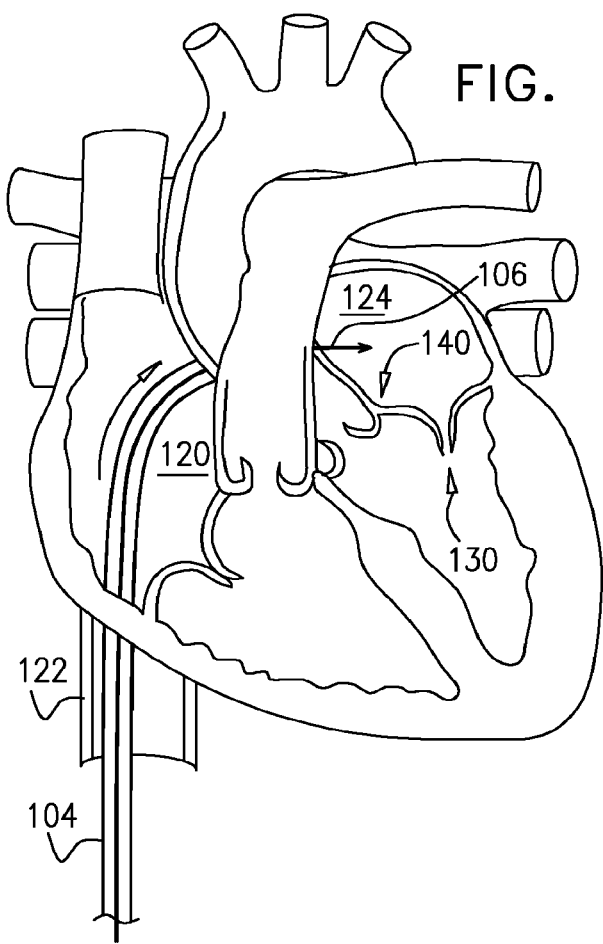

As shown in FIG. 6D, a resilient needle 106 and a dilator (not shown) are advanced through sheath 104 and into the heart. In order to advance sheath 104 transseptally into left atrium 124, the dilator is advanced to the septum, and needle 106 is pushed from within the dilator and is allowed to puncture the septum to create an opening that facilitates passage of the dilator and subsequently sheath 104 therethrough and into left atrium 124. The dilator is passed through the hole in the septum created by the needle. Typically, the dilator is shaped to define a hollow shaft for passage along needle 106, and the hollow shaft is shaped to define a tapered distal end. This tapered distal end is first advanced through the hole created by needle 106. The hole is enlarged when the gradually increasing diameter of the distal end of the dilator is pushed through the hole in the septum.

Figure 6E:
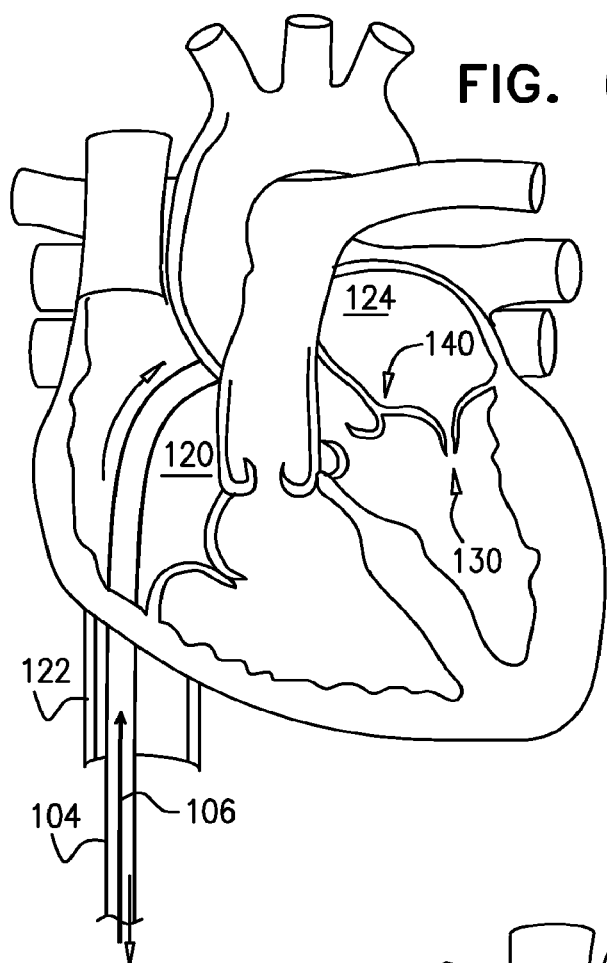

The advancement of sheath 104 through the septum and into the left atrium is followed by the extraction of the dilator and needle 106 from within sheath 104, as shown in FIG. 6E.

Figure 6F:
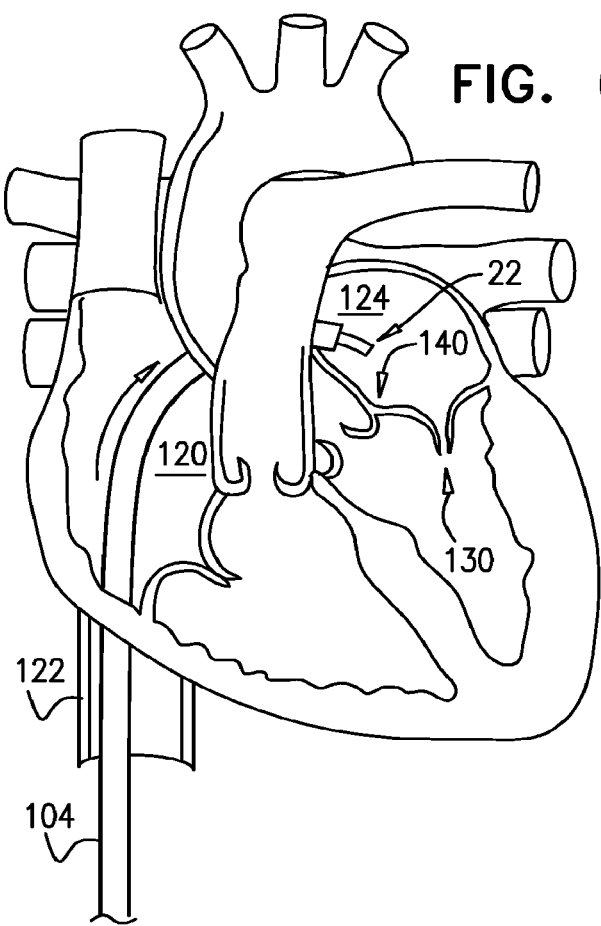

As shown in FIG. 6F, annuloplasty ring 22 (with anchor deployment manipulator 24 therein) is advanced through sheath 104 into left atrium 124.

Figure 6G:
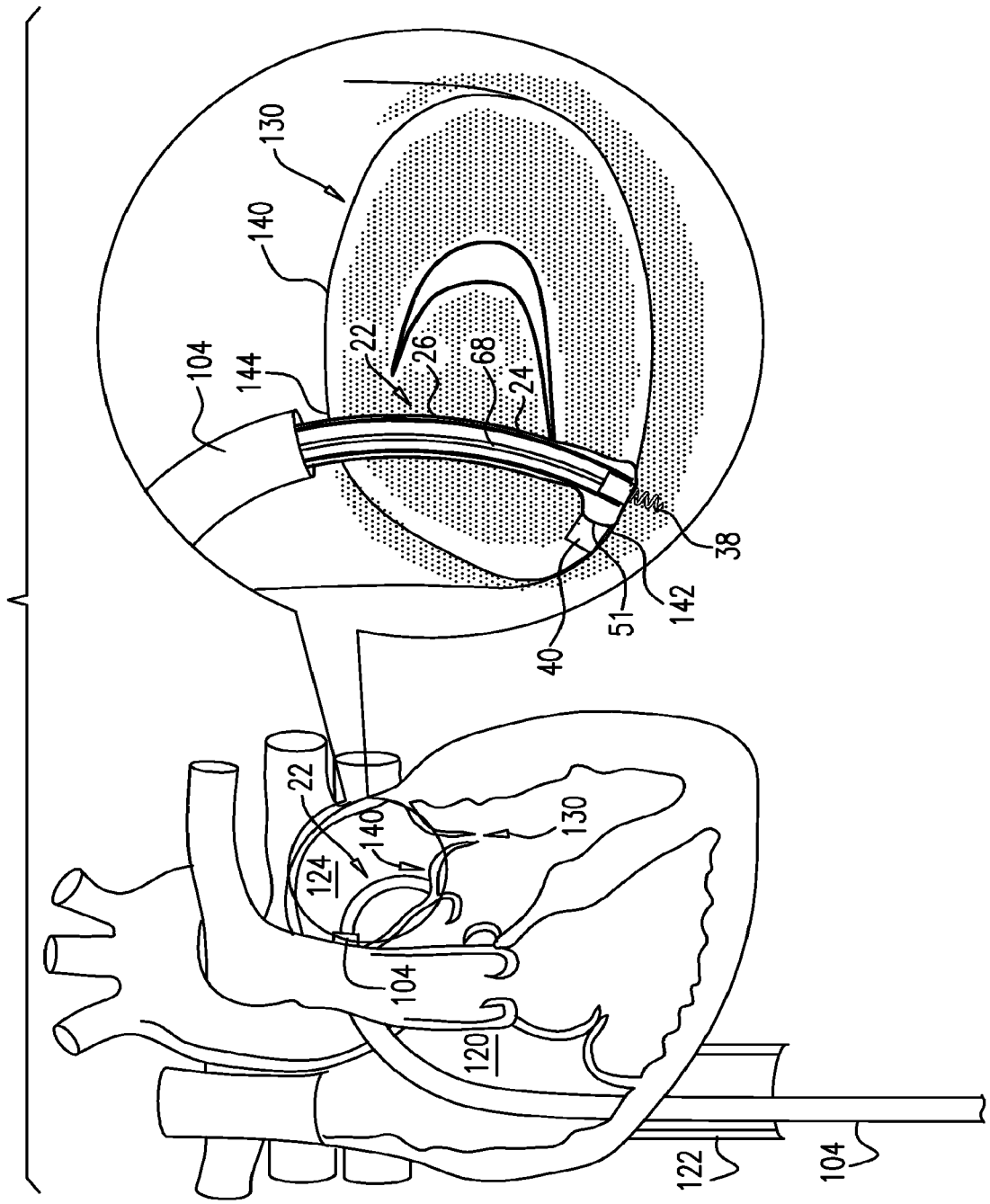

As shown in FIG. 6G, distal end 51 of sleeve 26 is positioned in a vicinity of a left fibrous trigone 142 of an annulus 140 of mitral valve 130. (It is noted that for clarity of illustration, distal end 51 of sleeve 26 is shown schematically in the cross-sectional view of the heart, although left trigone 142 is in reality not located in the shown cross-sectional plane, but rather out of the page closer to the viewer.) Alternatively, the tip is positioned in a vicinity of a right fibrous trigone 144 of the mitral valve (configuration not shown). Further alternatively, the distal tip of the sleeve is not positioned in the vicinity of either of the trigones, but is instead positioned elsewhere in a vicinity of the mitral valve, such as in a vicinity of the anterior or posterior commissure. For some applications, outer tube 66 of anchor deployment manipulator 24 is steerable, as is known in the catheter art, while for other applications, a separate steerable tube is provided, as described hereinbelow with reference to FIG. 10 and FIG. 11. In either case, the steering functionality typically allows the area near the distal end of the manipulator to be positioned with six degrees of freedom. Once positioned at the desired site near the selected trigone, manipulator 24 deploys a first anchor 38 through the wall of sleeve 26 into cardiac tissue near the trigone.

Figure 6H:
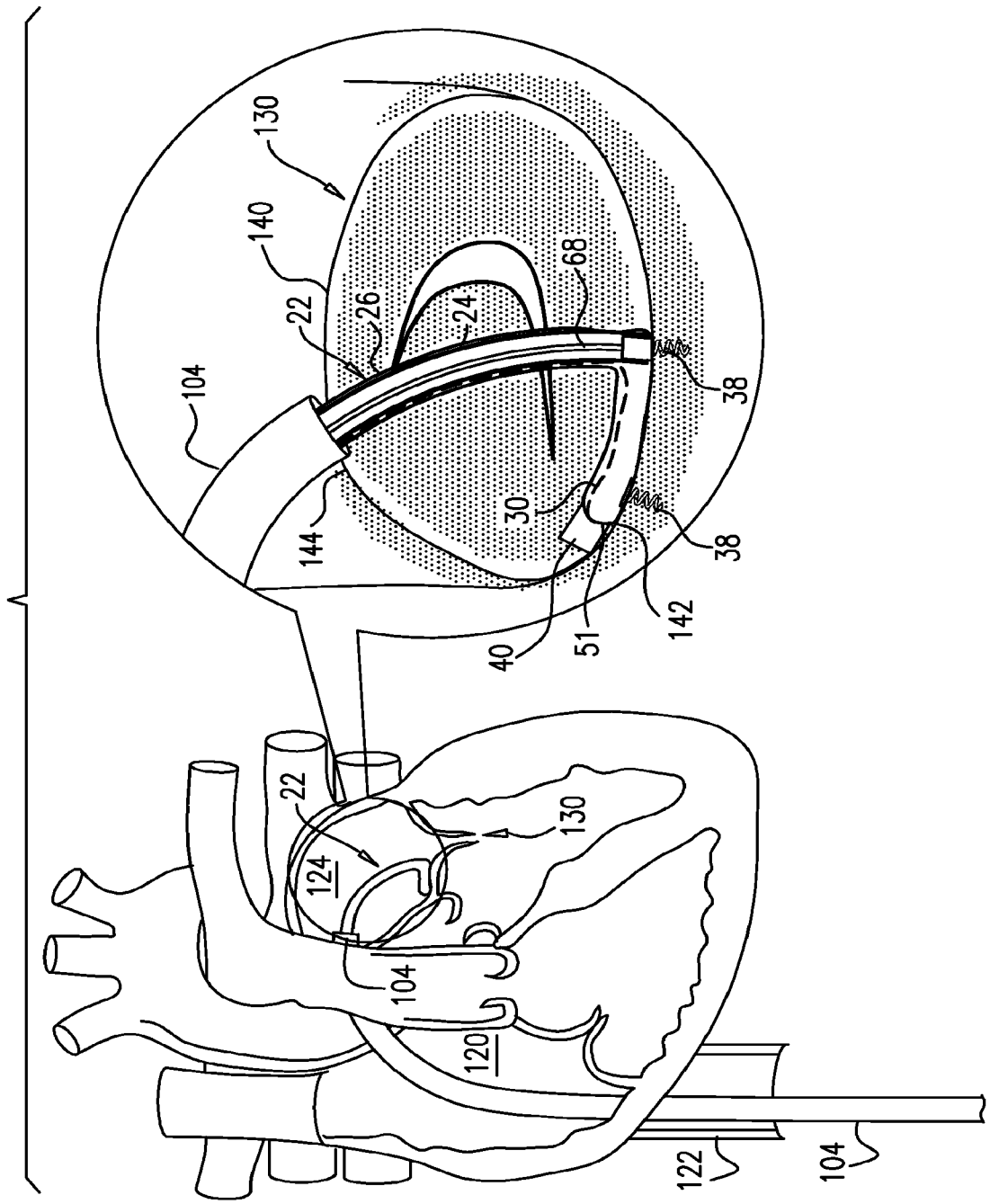

As shown in FIG. 6H, deployment manipulator 24 is repositioned along annulus 140 to another site selected for deployment of a second anchor 38. Typically, the first anchor is deployed most distally in the sleeve (generally at or within a few millimeters of the distal tip of the sleeve), and each subsequent anchor is deployed more proximally, such that the manipulator is gradually withdrawn in a proximal direction during the anchoring procedure. The already-deployed first anchor 38 holds the anchored end of sleeve 26 in place, so that the sleeve is drawn from the site of the first anchor towards the site of the second anchor. Deployment manipulator 24 deploys the second anchor through the wall of the sleeve into cardiac tissue at the second site. Depending on the tension applied between the first and second anchor sites, the portion of sleeve 26 therebetween may remain tubular in shape, or may become flattened, which may help reduce any interference of the ring with blood flow.

For some applications, in order to provide the second and subsequent anchors, anchor driver 68 is withdrawn from the subject's body via sheath 104 (typically while leaving outer tube 66 of the deployment manipulator in place in the sleeve), provided with an additional anchor, and then reintroduced into the subject's body and into the outer tube. Alternatively, the entire deployment manipulator, including the anchor driver, is removed from the body and subsequently reintroduced upon being provided with another anchor. Further alternatively, deployment manipulator 24 is configured to simultaneously hold a plurality of anchors, and to deploy them one at a time at the selected sites.

As shown in FIG. 6I, the deployment manipulator is repositioned along the annulus to additional sites, at which respective anchors are deployed, until the last anchor is deployed in a vicinity of right fibrous trigone 144 (or left fibrous trigone 142 if the anchoring began at the right trigone). Alternatively, the last anchor is not deployed in the vicinity of a trigone, but is instead deployed elsewhere in a vicinity of the mitral valve, such as in a vicinity of the anterior or posterior commissure.

As described hereinabove with reference to FIGS. 1A and 1B, a screwdriver tool or anchor driver 68 of deployment manipulator 24 is used to rotate spool 46 of contracting mechanism 40, in order to tighten ring 22. (For clarity of illustration, contracting member 30 of ring 22, although provided, is not shown in FIGS. 6A-I.) Alternatively, another technique is used to tighten the ring, such as described hereinabove.

For some applications, sleeve 26 is filled with a material (e.g., polyester, polytetrafluoroethylene (PTFE), polyethylene terephthalate (PET), or expanded polytetrafluoroethylene (ePTFE)) after being implanted. The material is packed within at least a portion, e.g., 50%, 75%, or 100%, of the lumen of sleeve 26. The filler material functions to prevent (1) formation within the lumen of sleeve 26 of clots or (2) introduction of foreign material into the lumen which could obstruct the sliding movement of contracting member 30.

For some applications, proximal end 49 of sleeve 26 is closed upon completion of the implantation procedure. Alternatively, the proximal end of the sleeve may have a natural tendency to close when not held open by manipulator 24.

Figure 7:
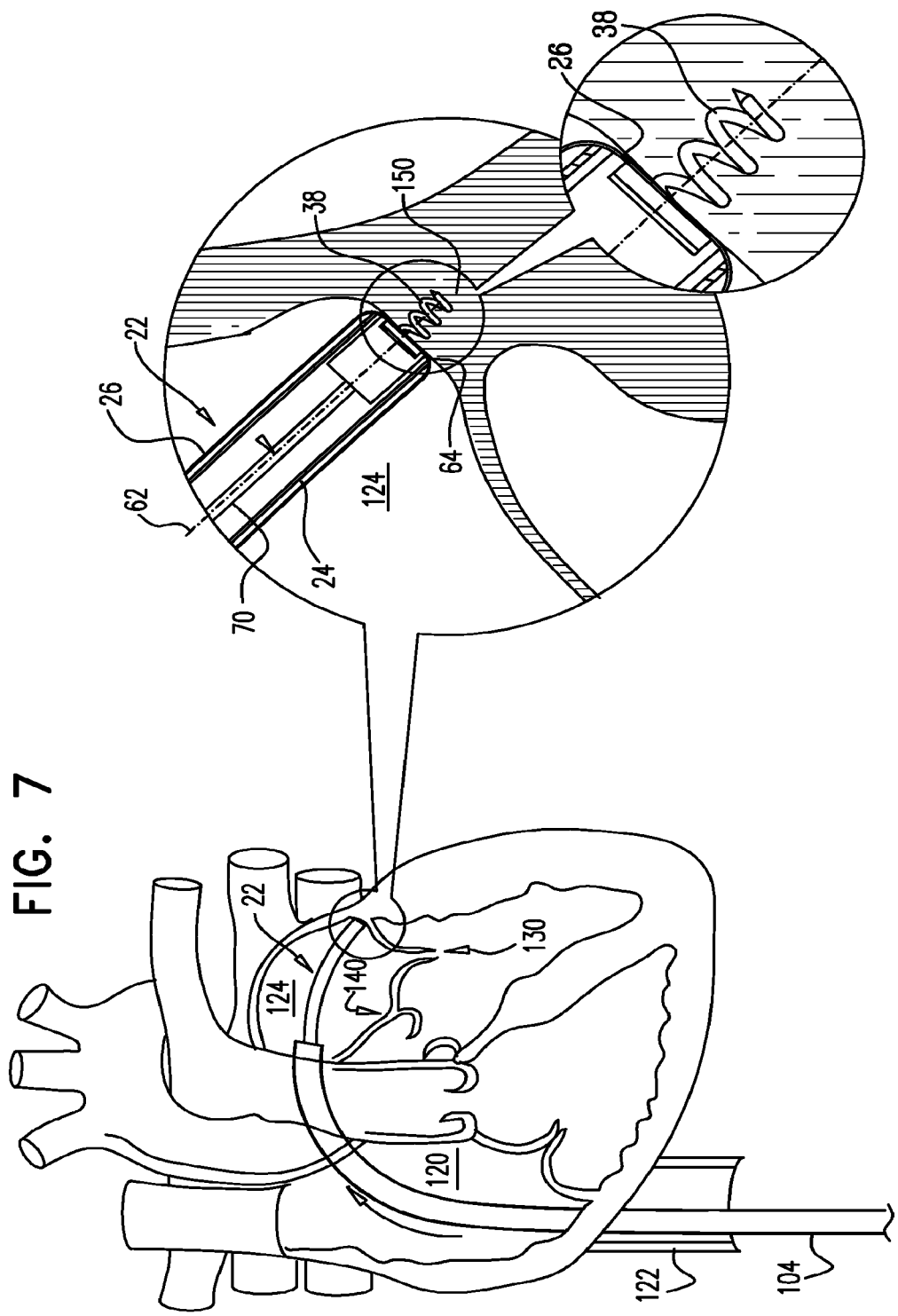
FIG. 7 is a schematic illustration of the deployment of an anchor into cardiac tissue, in accordance with an embodiment of the present invention.

Reference is made to FIG. 7, which is a schematic illustration of the deployment of one of anchors 38 into cardiac tissue, in accordance with an embodiment of the present invention. In this embodiment, one or more (such as all) of anchors 38 are deployed from left atrium 124, through tissue of the atrial wall, and into tissue of an upper region of the ventricular wall 150 near the atrium. Because the tissue of the upper region of ventricular wall is thicker than that of the atrial wall, deploying the anchors into the upper region of the ventricular wall generally provides more secure anchoring. In addition, because the anchors are not deployed laterally through the atrial wall, the risk of perforating the atrial wall is reduced.

Annuloplasty ring 22 may be advanced toward annulus 140 in any suitable procedure, e.g., a transcatheter procedure, a minimally invasive procedure, or an open heart procedure (in which case one or more elements of system 20 are typically rigid). Regardless of the approach, the procedure typically includes the techniques described hereinabove with reference to FIGS. 6G-I and 7.

For some applications, following initial contraction of annuloplasty ring 22 during the implantation procedure, the ring may be further contracted or relaxed at a later time after the initial implantation. Using real-time monitoring, tactile feedback and optionally in combination with fluoroscopic imaging, a screwdriver tool or anchor driver 68 of deployment manipulator 24 is reintroduced into the heart and used to contract or relax annuloplasty ring 22.

Reference is now made to FIG. 8, which is a schematic illustration of system 10 comprising a flexible pusher element 200, in accordance with an embodiment of the present invention. Pusher element 200 aids with accurately positioning successive anchors 38 during an implantation procedure, such as described hereinabove with reference to FIGS. 6H and 6I. For some applications, pusher element 200 is positioned partially within tube 66 of deployment manipulator 24 such that a distal portion 204 of pusher element 200 extends distally out of tube 66, through an opening 206 in a vicinity of a distal end of the tube (e.g., that is within 3 mm of the distal end, such as within 2 mm of the distal end). A proximal portion 202 of pusher element 200 passes through outer tube 66 from opening 206 to the proximal end of tube 66. Opening 206 is provided either through a wall of the tube (as shown in FIG. 8), or through the distal end of the tube (configuration not shown). Alternatively, pusher element 200 is positioned within sleeve 26, but outside of tube 66 (configuration not shown). Typically, the pusher element is elongated, and is as least as long as sleeve 26.

Pusher element 200 helps move the distal end of deployment manipulator 24 from a first site of the annulus at which the manipulator has already deployed a first anchor (e.g., anchor 38A in FIG. 8) to a second site for deployment of a second anchor (e.g., anchor 38B), in a direction indicated schematically by an arrow 210. Pusher element 200 is pushed distally out of opening 206 of tube 66, so that a distal end 212 of pusher element 200 engages and pushes against an interior surface of sleeve 26, in a direction indicated schematically by an arrow 214. The interior surface of the sleeve may be distal end 51 of the sleeve (as shown), or the wall of the sleeve at a location between distal end 51 and opening 206 (not shown). As a result, the distal end of manipulator 24 moves in the opposite direction, i.e., as indicated by arrow 210, toward a subsequent anchoring site. The movement in the direction of arrow 210 is generally along a line or curve defined by the portion of pusher element 200 already extended between the anchors that have already been deployed.

For some applications, as manipulator 24 is positioned at successive deployment sites of the cardiac tissue, pusher element 200 is extended respective distances through opening 206, each of which distances is successively greater. For other applications, after manipulator 24 is positioned at each successive deployment site, the pusher element is pulled back in a proximal direction, and again extended a desired distance in a distal direction, such that the pusher element pushes again the wall of the sleeve (at a different location on the wall for each successive relocation of manipulator 24).

This technique thus aids in locating each subsequent anchoring site for manipulator 24. The pusher element may also help control the distance between adjacent anchoring sites, because they surgeon may push the pusher element a known distance after deploying each anchor.

Pusher element 200 typically comprises a strip, wire, ribbon, or band, and has a cross-section that is circular, elliptical, or rectangular. Pusher element 200 typically comprises a flexible and/or superelastic material, such as a metal such as nitinol, stainless steel, or cobalt chrome. Distal end 212 of pusher element 200 is dull, so that it does not penetrate sleeve 26. For example, the distal end may be folded back, as shown in FIG. 8.

FIG. 9 is a schematic illustration of a pusher tube 250 applied to proximal end 49 of sleeve 26, in accordance with an embodiment of the present invention. Pusher tube 250 pushes gently in a distal direction on proximal end 49 of sleeve 26. For example, if, during withdrawal of outer tube 66 in a proximal direction, the outer tube snags on the wall of sleeve 26 (which, as mentioned above, may comprise braided or woven fabric), such pushing may help free the snag. For some applications, the techniques of this embodiment are practiced in combination with those of the embodiment described hereinbelow with reference to FIG. 12. (Although in the embodiment described with reference to FIG. 9, system 10 typically comprises contracting member 30, for clarity of illustration the contracting member is not shown in the figure.)

FIG. 10 is a schematic illustration of system 10 comprising a steerable tube 300, in accordance with an embodiment of the present invention. In this embodiment, outer tube 66 of deployment manipulator 24 is not steerable. Instead, to provide steering functionality, deployment manipulator 24 comprises a separate steering tube 300, which is positioned around at least a portion of outer tube 66. Outer tube 66, because it does not provide this steering functionality, may have a smaller diameter than in the embodiment described hereinabove with reference to FIG. 3. Because outer tube 66 has a smaller diameter, sleeve 26 may also have a smaller diameter than in the embodiment described hereinabove with reference to FIG. 3. For some applications, the techniques of this embodiment are practiced in combination with those of the embodiment described hereinabove with reference to FIG. 9. (Although in the embodiment described with reference to FIG. 10, system 10 typically comprises contracting member 30, for clarity of illustration the contracting member is not shown in the figure.)

FIG. 11 is a schematic illustration of system 10 comprising a steerable tube 320, in accordance with an embodiment of the present invention. In this embodiment, outer tube 66 of deployment manipulator 24 is not steerable. Steering functionality is instead provided by separate steering tube 320, which is positioned around at least a portion of shaft 70 of anchor driver 68, and within outer tube 66. For some applications, the techniques of this embodiment are practiced in combination with those of the embodiment described hereinabove with reference to FIG. 9. (Although in the embodiment described with reference to FIG. 11, system 10 typically comprises contracting member 30, for clarity of illustration the contracting member is not shown in the figure.)

Figure 12:
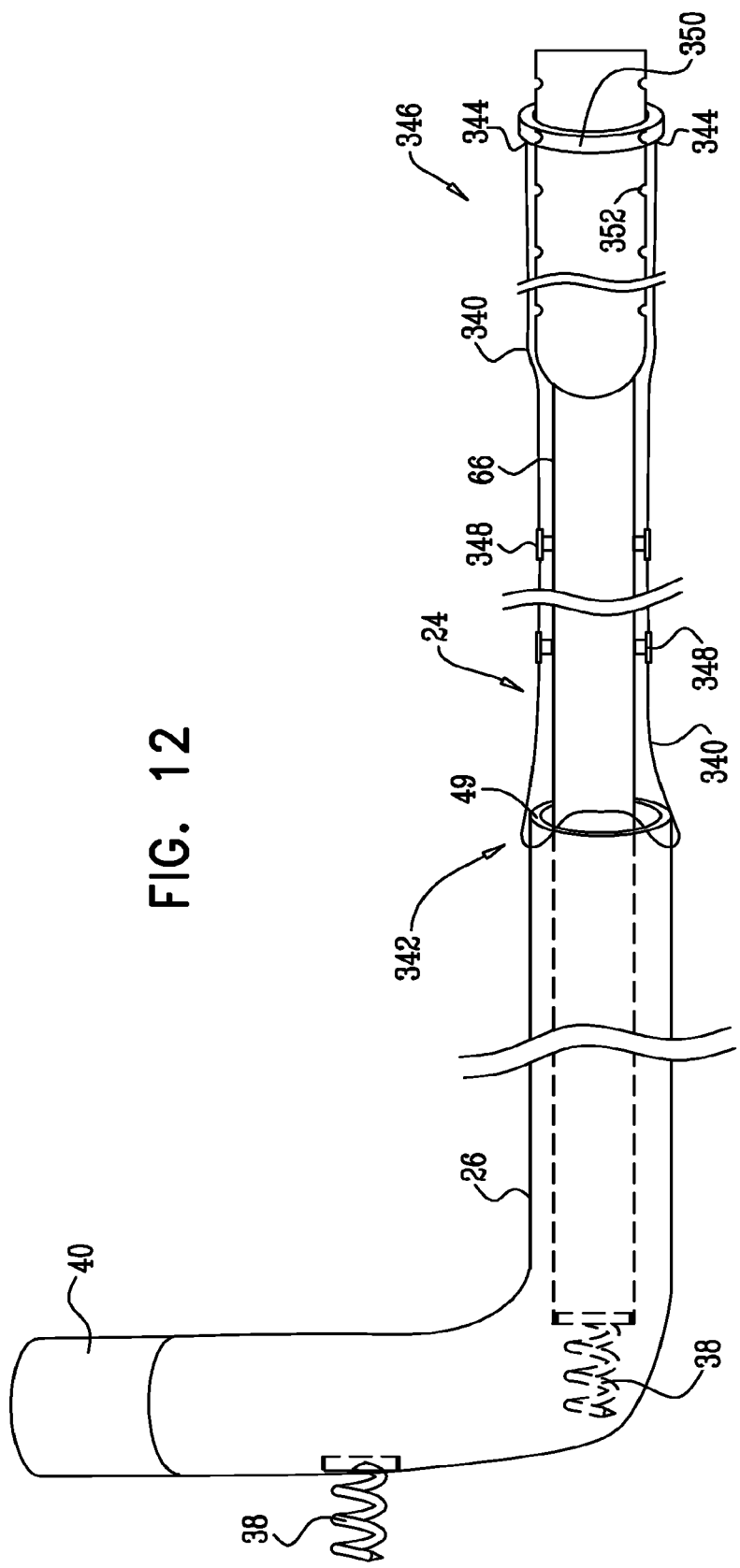
FIG. 12 is a schematic illustration of the system of FIGS. 1-4 comprising a pulling wire, in accordance with an embodiment of the present invention.

FIG. 12 is a schematic illustration of system 10 comprising a pulling wire 340, in accordance with an embodiment of the present invention. A distal portion 342 of pulling wire 340 is coupled to proximal end 49 of sleeve 26, such as by passing through one or more holes near the proximal end. One or more proximal portions 344 of the pulling wire are coupled to an external control handle 346 of system 10, which is manipulated by the surgeon outside of the subject's body. Optionally, a portion of deployment manipulator 24 (e.g., a portion of outer tube 66) which is never inserted in sleeve 26 comprises one or more coupling elements 348, such as loops or tubes, through which pulling wire 340 passes in order to hold the pulling wire close to the external surface of the deployment manipulator.

Pulling wire 340 holds sleeve 26 surrounding deployment manipulator 24. As the pulling wire is released in a distal direction as deployment manipulator 24 is withdrawn in a proximal direction, the release of the sleeve allows the sleeve to gradually be removed from around the deployment manipulator. In FIG. 12, the sleeve is shown partially removed from the manipulator, including the portion of the sleeve through which one of anchors 38 has been deployed.

For some applications, control handle 346 is configured to release pulling wire 340 incrementally, such that each time the wire is further released by a set distance. As a result, the deployment manipulator is withdrawn from the sleeve by this set distance, and subsequently-deployed anchors are approximately this set distance apart from one another. For example, the handle may comprise a control ring 350 that is coupled to proximal portions 344 of the wire, and removably engages slots 352 on the handle that are spaced apart by this set distance. Upon completion of the implantation procedure, in order to detach the pulling wire from the sleeve, one end of the wire may be cut or released, and the wire detached from the sleeve by pulling on the other end of the wire.

(Although in the embodiment described with reference to FIG. 12, system 10 typically comprises contracting member 30, for clarity of illustration the contracting member is not shown in the figure.)

Although annuloplasty ring 22 has been described hereinabove as comprising a partial annuloplasty ring, in some embodiments of the present invention, the ring instead comprises a full annuloplasty ring.

In some embodiments of the present invention, system 20 is used to treat an atrioventricular valve other than the mitral valve, i.e., the tricuspid valve. In these embodiments, annuloplasty ring 22 and other components of system 20 described hereinabove as being placed in the left atrium are instead placed in the right atrium. Although annuloplasty ring 22 is described hereinabove as being placed in an atrium, for some application the ring is instead placed in either the left or right ventricle.

For some applications, techniques described herein are practiced in combination with techniques described in one or more of the references cited in the Background section of the present patent application.

Additionally, the scope of the present invention described hereinabove with reference to FIGS. 1A-12 includes embodiments described in the following applications, which are incorporated herein by reference. In an embodiment, techniques and apparatus described in one or more of the following applications are combined with techniques and apparatus described hereinabove with reference to FIGS. 1A-12:

PCT Publication WO 06/097931 to Gross et at, entitled, "Mitral Valve treatment techniques," filed Mar. 15, 2006;

U.S. Provisional Patent Application 60/873,075 to Gross et al., entitled, "Mitral valve closure techniques," filed Dec. 5, 2006;

U.S. Provisional Patent Application 60/902,146 to Gross et at, entitled, "Mitral valve closure techniques," filed on Feb. 16, 2007;

U.S. Provisional Patent Application 61/001,013 to Gross et al., entitled, "Segmented ring placement," filed Oct. 29, 2007;

PCT Patent Application PCT/IL07/001503 to Gross et al., entitled, "Segmented ring placement," filed on Dec. 5, 2007, which published as PCT Publication WO 08/068756;

U.S. Provisional Patent Application 61/132,295 to Gross et al., entitled, "Annuloplasty devices and methods of delivery therefor," filed on Jun. 16, 2008;

U.S. patent application Ser. No. 12/341,960 to Cabiri, entitled, "Adjustable partial annuloplasty ring and mechanism therefor," filed on Dec. 22, 2008, which published as US Patent Application Publication 2010/0161047;

U.S. Provisional Patent Application 61/207,908 to Miller et al., entitled, "Actively-engageable movement-restriction mechanism for use with an annuloplasty structure," filed on Feb. 17, 2009; and U.S. patent application Ser. No. 12/435,291 to Maisano et al., entitled, "Adjustable repair chords and spool mechanism therefor," filed on May 4, 2009, which published as US Patent Application Publication 2010/0161041.

FIGS. 13A-B are schematic illustrations of an anchor deployment system 420, in accordance with an application of the present invention. Anchor deployment system 420 comprises an anchor deployment tool 430, which is configured to deliver a plurality of anchors 432 to respective sites within a body of a subject, and to couple the anchors to tissue at the sites. For some applications, tool 430 is configured to deploy anchors 432 to cardiac sites within the heart, such as in a vicinity of a valve annulus. Tool 430 comprises a flexible outer tube 434, within which is positioned a flexible inner shaft 436. Tool 430 further comprises a rotating deployment element 438, coupled to a distal shaft end 439 of inner shaft 436.

As shown in FIG. 13A, tool 430 (e.g., flexible outer tube 434) is configured to provide an anchor storage area 440, which is configured to initially store the plurality of anchors 432. The anchors are positioned within outer tube 434 such that inner shaft 436 passes through respective longitudinal channels of the anchors, as described hereinbelow with reference to FIGS. 18A-C. A distal anchor storage end 441 of anchor storage area 440 is typically at distance of at least 1 cm from a distal tube end 442 of outer tube 434, such as at least 3 cm or at least 5 cm, to enable flexibility and manipulation of the tool end. Distal anchor storage end 441 is typically at a distance of no more than 90 cm from distal tube end 442, such as no more than 25 cm, to maintain the comfort and stability level of the user. For some applications, distal anchor storage end 441 is at a distance of between 3 cm and 25 cm from distal tube end 442, such as between 5 cm and 25 cm. Tool 430 typically comprises a spring 444, which is arranged to apply a distally-directed force to the proximal-most anchor within anchor storage area 440, thereby holding the anchors within the storage area, and advancing the remaining anchors distally as each of the anchors is separately deployed.

The portion of tool 430 between distal anchor storage area end 441 and distal tube end 442 of outer tube 434 serves as a distal anchor manipulation area 450 of tool 430. Anchor manipulation area 450 is typically flexible and steerable. Typically, only one anchor at a time is deployed through anchor manipulation area 450 and into the tissue of the subject, such that no more than exactly one anchor is within anchor manipulation area 450 at any given time. As a result, anchor manipulation area 450 retains its flexibility. Because the anchors are typically rigid, when more than one of the anchors are longitudinally contiguously positioned within tool 430, the area of the tool in which the anchors are positioned becomes fairly stiff, substantially losing the flexibility it would otherwise have. Thus, while anchor storage area 440 is fairly rigid, anchor manipulation area 450 remains flexible because it only contains exactly one anchor at a given time. The stiffness of the area of the tool in which the anchors are positioned also may enable the user to better control the exact location of distal-most anchor 432 currently stored in anchor storage area 440.

The steering functionality of distal anchor manipulation area 450 typically allows the area near the distal end of tool 430 to be positioned with six degrees of freedom. For some applications, flexible outer tube 434 is configured to provide the steering functionality to distal anchor manipulation area 450. Flexible outer tube 434 comprises one or more steering wires, the pulling and releasing of which cause deflection of distal tube end 442, using deflection techniques known in the catheter art. Alternatively or additionally, flexible inner shaft 436 is configured to provide the steering functionality to distal anchor manipulation area 450. Flexible inner shaft 436 comprises one or more steering wires for deflecting the distal end of the inner shaft. Still further alternatively or additionally, a separate flexible tube is provided for providing the steering functionality. The separate tube is positioned within flexible outer tube 434 or around the outer tube, and comprises one or more steering wires for deflecting the distal end of the inner shaft. The curvature of the tool may be pre-shaped, or bendable by application of an external force (such as a conventional colonoscope) or using an internal or external wire (configuration not shown). For some applications, the steering functionality is provided by a combination of more than one of flexible outer tube 434, flexible inner shaft 436, and the separate flexible tube, e.g., by (a) flexible outer tube 434 and flexible inner shaft 436, (b) flexible outer tube 434 and the separate flexible tube, (c) flexible inner shaft 436 and the separate flexible tube, or (d) all of flexible outer tube 434, flexible inner shaft 436, and the separate flexible tube.

For some applications, an external control handle is provided for controlling tool 430. The control handle comprises circuitry for manipulating the steering wires to provide the steering functionality.

For some applications, flexible inner shaft 436 comprises stainless steel SS 304, Nitinol, PEEK®, polyester, or another polymer. For some applications, outer tube 434 comprises stainless steel SS 304, Nitinol, PEEK®, polyester, or another polymer. For some applications, flexible inner shaft 436 has a diameter of at least 0.8 mm, no more than 3 mm, and/or between 0.8 and 3 mm, such as between 1 and 2 mm. For some applications, outer tube 434 has an outer diameter of at least 2 mm, no more than 4 mm, and/or between 2 and 4 mm, e.g., 3 mm or 3.2 mm. For some applications, outer tube 434 has an inner diameter of at least 1.5 mm, no more than 3.5 mm, and/or between 1.5 and 3.5 mm, e.g., 2.6 mm.

For some applications, anchor deployment tool 430 further comprises a hemostasis valve 480, as shown in FIG. 13B. Hemostasis valve 480 minimizes leakage of blood, and entrance of air (thereby reducing the risk of air emboli), during a percutaneous procedure performed using system 420. A proximal end of flexible outer tube 434 is sealingly coupled to a distal port of valve 480. Inner shaft 436 passes through valve 480, which maintains a seal around the inner shaft, while allowing the inner shaft to slide distally and proximally through the valve during deployment of anchors 432, as described hereinbelow with reference to FIGS. 16A-D. Valve 480 optionally comprises a side port 482 for flushing the system, as is known in the hemostasis valve art. For other applications, the anchor deployment tool does not comprise the hemostasis valve.

Reference is made to FIGS. 14 and 15A-B, which are schematic illustrations showing the assembly of components of anchor deployment system 420, in accordance with an application of the present invention. Typically, spring 444 is positioned around a proximal portion of flexible inner shaft 436. A distal end 458 of the spring applies a force in a distal direction against the proximal end of the proximal-most anchor 432 (right-most in the figures) stored in anchor storage area 440. The plurality of anchors 432 are initially positioned end-to-end longitudinally contiguously around flexible inner shaft 436 within anchor storage area 440. By way of example, FIG. 14 shows five anchors 432. Typically, system 420 is configured to store between 6 and 20 anchors 432, such as between 8 and 16 anchors 432.

As shown in the blow-up of FIG. 14, and described in more detail hereinbelow with reference to FIGS. 18A-C, each of anchors 432 comprises a helical tissue coupling element 460, and a tool-engaging head 462, fixed to one end of the tissue coupling element. Rotating deployment element 438 is configured to removably engage tool-engaging head 462, as described in more detail hereinbelow with reference to FIGS. 16A-D and 18A-C.

For some applications, tool 430 provides an anchor restraining mechanism 470 in a vicinity of distal anchor storage area end 441. Anchor restraining mechanism 470 is configured to temporarily restrain at least the distal-most anchor 432 currently stored in anchor storage area 440 from advancing in a distal direction as another one of the anchors is deployed through anchor manipulation area 450 and into the tissue of the subject. Optionally, anchor restraining mechanism 470 is also configured to temporarily restrain at least the distal-most anchor 432 from withdrawing in a proximal direction as inner shaft 436 is withdrawn in the proximal direction to load a subsequent one of the anchors.

For some applications, as shown in the blow-up of FIG. 15A, anchor restraining mechanism 470 comprises one or more distal tabs 472 for temporarily restraining the distal-most anchor 432 currently stored in anchor storage area 440 from advancing in the distal direction. The distal tabs may be cut out of flexible outer tube 434, as shown, or they may be provided as separate elements coupled to the outer tube. The distal tabs apply a force in a radially-inward direction against a distal portion of anchor 432, gently squeezing against the distal portion. The force is sufficient to prevent distal motion of distal-most anchor 432 and the other anchors currently stored in anchor storage area 440, which otherwise would be advanced distally by the force applied on the proximal-most anchor 432 by spring 444. However, the force is insufficient to prevent distal advancement of distal-most anchor 432 when the anchor is engaged and advanced distally by rotating deployment element 438, as described hereinbelow with reference to FIGS. 16A-B. For some applications, anchor restraining mechanism 470 comprises two distal tabs 472, typically on opposite sides of the outer tube (typically axially aligned with each other), as shown, while for other applications, the anchor restraining mechanism comprises exactly one distal tab, or three or more distal tabs, e.g., three or four distal tabs (typically axially aligned with one another).

For some applications, anchor restraining mechanism 470 comprises a set 473 of one or more proximal tabs 474 for temporarily restraining the distal-most anchor 432 currently stored in anchor storage area 440 from withdrawing in the proximal direction. The proximal tabs may be cut out of flexible outer tube 434, as shown, or they may be provided as separate elements coupled to the outer tube. The distal ends of the proximal tabs engage the proximal end of the tool-engaging head of distal-most anchor 432. For some applications, set 473 comprises two proximal tabs 474, typically on opposite sides of the outer tube (typically axially aligned with each other), as shown, while for other applications, the set comprises exactly one proximal tab, or three or more proximal tabs, e.g., three or four proximal tabs (typically axially aligned with one another).

Reference is made to FIGS. 16A-D, which are schematic illustrations of the deployment of a single one of anchors 432 into tissue using anchor deployment tool 430, in accordance with an application of the present invention. As shown in FIG. 16A, the anchor to be deployed is the distal-most one of the anchors stored in anchor storage area 440, and is initially restrained in the anchor storage area by anchor restraining mechanism 470. Flexible inner shaft 436 is advanced in a distal direction until rotating deployment element 438 directly engages tool-engaging head 462 of the anchor (by "directly engages," it is meant that rotating deployment element 438 comes in direct contact with the anchor, rather than indirect contact via one or more of the other anchors). Rotating deployment element 438 assumes its radially-expanded state, as described hereinbelow with reference to FIG. 19A, to enable this engagement.

As shown in FIG. 16B, flexible inner shaft 436 is advanced in the distal direction, until rotating deployment element 438 brings the anchor into contact with tissue 490 of a subject at a first site. For example, the tissue may be cardiac tissue. Typically, anchor deployment tool 430 is configured such that, as rotating deployment element 438 advances each of the anchors in the distal direction, only the single anchor 432 currently being advanced is within distal anchor manipulation area 450. Rotating deployment element 438 is rotated, in order to screw helical tissue coupling element 460 of the anchor into the tissue. For some applications, rotating deployment element 438 is rotated by rotating flexible inner shaft 436. For other applications, rotating deployment element 438 is rotated by rotating an additional rotation shaft provided within flexible inner shaft 436, which additional shaft is coupled to rotating deployment element 438. Rotation of rotating deployment element 438 typically rotates only the anchor currently engaged by the deployment element, while the other anchors still stored in the storage area typically are not rotated.

Typically, anchor 432 is deployed from distal tube end 442 of outer tube 434 of tool 430 into cardiac tissue 490 in a direction parallel to a central longitudinal axis 492 of outer tube 434 through distal tube end 442, and/or parallel to central longitudinal axis 500 of anchor 432, as described hereinbelow with reference to FIGS. 18A-C.

Also as shown in FIG. 16B, the evacuation of the distal-most anchor from anchor restraining mechanism 470 frees up the anchor restraining mechanism for the next distal-most anchor remaining in anchor storage area 440. Spring 444 distally advances all of anchors 432 remaining in anchor storage area 440, until the next distal-most anchor is positioned within anchor restraining mechanism 470.

As shown in FIG. 16C, after the anchor has been coupled to tissue 490, rotating deployment element 438 is disengaged from the anchor by withdrawing the rotating deployment element in a proximal direction. As the rotating deployment element passes through the next anchor in the proximal direction, the rotating deployment element is squeezed by the engaging opening of tool-engaging head 462 of the next anchor, causing the rotating deployment element to assume its radially-compressed state, as described hereinbelow with reference to FIG. 19B.

As shown FIG. 16D, anchor deployment tool 430 is repositioned to deploy a second anchor 432 at a second site of tissue 490, different from the first site. Such repositioning is typically accomplished using the steering functionality of distal anchor manipulation area 450, as described hereinabove. The steps of the deployment method are repeated, until as many anchors 432 as desired have been deployed, at respective sites, e.g., a first site, a second site, a third site, a fourth site, etc.

Reference is made to FIGS. 17A-B, which are schematic illustrations of an alternative configuration of anchor deployment system 420, in accordance with an application of the present invention. In this configuration, anchor restraining mechanism 470 typically comprises one or more distal tabs 472, as in the configuration described hereinabove with reference to FIGS. 14, 15A-B, and 16A-D. Unlike in the configuration described hereinabove with reference to FIGS. 14, 15A-B, and 16A-D, in this configuration anchor restraining mechanism 470 comprises a plurality of sets 473 of proximal tabs 474, labeled 473A, 473B, 473C, . . . in FIGS. 17A-B. Each set of proximal tabs 474 engages exactly one anchor 432. For example, the distal ends of proximal tabs 474 of set 473A engage the proximal end of the tool-engaging head of distal-most anchor 432, and the distal ends of proximal tabs 474 of set 473B engage the proximal end of the tool-engaging head of second-to-distal-most anchor 432.

Sets 473 thus provide respective anchor storage locations. Therefore, the anchor restraining mechanism comprises a number of sets 473 greater than or equal to the number of anchors 432 initially stored in anchor storage area 440. For some applications, anchor restraining mechanism 470 comprises between 6 and 20 sets 473, such as between 8 and 16 sets 473. For some applications, each of sets 473 comprises two proximal tabs 474, typically on opposite sides of the outer tube (typically axially aligned with each other), as shown, while for other applications, each of the sets comprises exactly one proximal tab, or three or more proximal tabs, e.g., three or four proximal tabs (typically axially aligned with one another).

For some applications, each of sets 473 (except the proximal-most set 473) additionally functions as a distal tab 472 for the anchor proximally adjacent to the set. For example, set 473A, in addition to engaging distal-most anchor 432A, also prevents distal motion of second-to-distal-most anchor 432.

Unlike in the configuration described hereinabove with reference to FIGS. 14, 15A-B, and 16A-D, in the present configuration each of anchors 432 remains in place in its initial, respective anchor storage location in anchor storage area 440, until the anchor is individually advanced out of anchor storage area 440 during deployment by anchor deployment tool 430. Spring 444 is thus typically not provided in this configuration. Deployment of the anchors is typically performed as described hereinabove with reference to FIGS. 16A-D, except:

at the step described with reference to FIG. 16B, spring 444 does not distally advance the remaining anchors (as mentioned above, spring 444 is typically not provided in this configuration); and at the step described with reference to FIG. 16C, anchor deployment tool 430 is withdrawn further proximally, until the anchor deployment tool reaches the next remaining anchor 432 in anchor storage area 440. The next anchor, as mentioned above, has remained in its original location even after deployment of more distally positioned anchor(s) 432.

Reference is now made to FIGS. 18A-C, which are schematic illustrations of one of anchors 432 from three different views, in accordance with an application of the present invention. As described above, each of anchors 432 comprises helical tissue coupling element 460, and tool-engaging head 462, fixed to one end of the tissue coupling element (the proximal end of the tissue coupling element, opposite the distal end that first penetrates the tissue). Anchor 432 comprises a hard material, such as metal, e.g., steel, Nitinol, or stainless steel SS316LVM. Anchor 432 may be manufactured from a single piece of material, or coupling element 460 and tool-engaging head 462 may be manufactured from separate pieces of material and fixed together.

Typically, helical tissue coupling element 460 has an inner diameter D1 of at least 1.5 mm, no more than 2.5 mm, and/or between 1.5 and 2.5 mm, e.g., 1.8 mm, along an entire length thereof along a central longitudinal axis 500 of anchor 432 (although inner diameter D1 is shown as being constant along the entire length of coupling element 460, the inner diameter optionally varies along the length of the coupling element). Inner diameter D1 is sufficiently large to allow passage through helical tissue coupling element 460 of flexible inner shaft 436 and rotating deployment element 438, optionally even when rotating deployment element 438 is in its radially-expanded state, as described hereinbelow with reference to FIG. 19A. An outer diameter D2 of helical tissue coupling element 460 may be, for example, at least 2.4 mm, no more than 5 mm, and/or between 2.4 and 5 mm, e.g., 2.4 mm.

Tool-engaging head 462 is shaped so as to define an engaging opening 502 that passes entirely through the tool-engaging head along axis 500. The engaging opening is typically at least partially non-circular, in order to engage rotating deployment element 438. For example, as shown in FIGS. 18A-C, engaging opening 502 may be shaped so as to define a proximal non-circular internal engaging surface 466, and a distal circular non-engaging surface 464. Proximal engaging surface 466 is shaped to engage rotating deployment element 438, such that rotation of the deployment element rotates tool-engaging head 462 and anchor 432. For example, proximal engaging surface 466 may be rectangular (e.g., square), teethed (e.g., defining a plurality of squares with which rotating element 438 can engage, for applications in which engaging elements 520A and 520B together have a square cross-sectional shape), star-shaped, polygonal (e.g., octagonal), or any other appropriate non-circular shape.

A portion of deployment element 438 may pass partially or completely through distal non-engaging surface 464, without engaging this surface. The non-engaging surface may serve as a shoulder, which pushes against tissue 490, providing resistance when the anchor has been sufficiently screwed into the tissue. Optionally, deployment element 438 does not pass entirely through distal non-engaging surface 464, such that the deployment element does not press against or into the tissue. Alternatively, the deployment element may protrude slightly from the distal non-engaging surface 464, as shown in FIGS. 20A-B, when no force is applied to the deployment element by the tissue. Optionally, when the anchor is pressed against the tissue, inner spaces in the tool-engagement head 462 of the anchor allow the deployment element to sink into the anchor, and not press against the tissue.

Engaging opening 502 typically has a cross-sectional area (perpendicular to axis 500) of at least 0.8 mm2, such as at least 1.2 mm2. The area is sufficient large to allow passage through engaging opening 502 of flexible inner shaft 436 and rotating deployment element 438, when the rotating deployment element assumes its radially-compressed state by being withdrawn in a proximal direction (from tissue coupling element 460 toward tool-engaging head 462), as described hereinbelow with reference to FIG. 19B.

For some applications, the anchor is used to couple a sheet of material, such as a fabric, to tissue 490. For these applications, because the tissue coupling element is fixed near the edge of the tool-engaging head, the sheet resists further rotation of the anchor once the anchor is fully screwed into the tissue and the tool-engaging head contacts the sheet. Such resistance prevents accidental over-rotation of the anchor, which could tear the tissue or the sheet. In contrast, in anchors in which the tissue coupling element is fixed at or near the center of the tool-engaging head, the sheet does not resist rotation of the anchor after the anchor has been fully screwed into the tissue and the tool-engaging head contacts the sheet. For some applications, the surgeon or a sensor sense increased resistance to rotation of the tissue coupling element when the sheet resists the rotation, and, responsively the sensed increased resistance, the surgeon ceases rotating the tissue coupling element into the tissue For some applications, anchor deployment system 420 comprises a torque-limiting element, as is known for conventional screwdrivers, to prevent over-application of torque. Alternatively or additionally, for some applications, anchor deployment system 420 comprises a sensor (e.g., a torque transducer), for measuring the resistance to rotation of anchor 432. When the measured resistance exceeds a threshold value, the system generates a signal alerting the surgeon, and/or discontinues rotation of inner shaft 436. The increased resistance is typically caused by the sheet, as described above, and/or the non-engaging surface (shoulder) of the anchor head, as described above.

For some applications, a proximal-most portion 506 of helical tissue coupling element 460, at the end which is fixed to tool-engaging head 462, is generally straight and oriented generally parallel to axis 500, i.e., at angle of between 0 and 15 degrees with the axis, such as 0 degrees. Proximal-most portion 506 typically has a length of between 0.5 and 2 mm, such as about 1 mm.

The outer perimeter of tool-engaging head 462 is typically circular, and an outer diameter D3 of tool-engaging head 462 may be, for example, at least 2 mm, no more than 7 mm, and/or between 2 and 7 mm, such as between 2.5 and 5 mm, e.g., 2.4 mm, 2.5 mm, or 3 mm.

The outer diameter of anchor 432 is typically equal to outer diameter D3 of tool-engaging head 462, or, alternatively, to outer diameter D2 of coupling element 460. The outer diameter of anchor 432 may be, for example, at least 2 mm, no more than 7 mm, and/or between 2 and 7 mm, such as between 2.5 and 5 mm. The entire length of anchor 432, measured along axis 500, is typically at least 2.5 mm, no more than 6 mm, and/or between 2.5 and 6 mm, such as between 3 and 4.5 mm.

The proximal end of tissue coupling element 460 is typically fixed to tool-engaging head 462 near the outer perimeter of the tool-engaging head, such that the tissue coupling element does not block engaging opening 502. For example, as labeled in the top-view of the anchor in FIG. 18C, the tissue coupling element may be fixed to the tool-engaging head such that one or more of the following dimension characterize the anchor.

a distance D5 between (a) a center 510 of the proximal end of tissue coupling element 460 and (b) an outer perimeter of tool-engaging head 462 is no more than 20% of a width D3 of tool-engaging head 462 (the width is a diameter for applications in which the head is circular), such as no more than 10% of width D3. For example, distance D5 may be between 0.1 and 0.3 mm, e.g., 0.2 mm;

a distance D6 between (a) a most radially-inward portion 512 of the proximal end of tissue coupling element 460 (i.e., the portion of the proximal end that is closest to central longitudinal axis 500 of the anchor) and (b) the outer perimeter of tool-engaging head 462 is no more than 40% of width D3 of tool-engaging head 462 (the width is a diameter for applications in which the head is circular), such as no more than 30% of width D3, or no more than 20% of width D3. For example, distance D6 may be between 0.3 and 0.5 mm, e.g., 0.4 mm; and/or a distance between (a) a most radially-outward portion 514 of the proximal end of tissue coupling element 460 (i.e., the portion of the proximal end that is furthest from central longitudinal axis 500 of the anchor) and (b) the outer perimeter of tool-engaging head 462 is no more than 10% of width D3 of tool-engaging head 462 (the width is a diameter for applications in which the head is circular), such as no more than 5% of width D3, e.g., 0. For example, distance D6 may be between 0 and 0.1 mm, e.g., 0 mm.

Anchor 432, including both helical tissue coupling element 460 and tool-engaging head 462, is thus shaped so as to provide a channel along the entire length of the anchor, through which flexible inner shaft 436 can pass, and through which rotating deployment element 438 can pass when in its radially-compressed state, as described hereinabove with reference to FIGS. 13A-4D. More generally, as shown in FIG. 18B, the channel is sized and shaped such that a right circular cylinder 504 could be placed within the channel, coaxial with anchor 432 (i.e., the axis of the cylinder coincides with central longitudinal axis 500 of anchor 432), and along the entire length of the tissue anchor, the cylinder having a diameter D4 of at least 1 mm, such as at least 2 mm. Typically, diameter D4 is between 0.05 and 1 mm greater than diameter D3 of tool-engaging head 462. It is to be understood that cylinder 504 is an abstract geometric shape, rather than an element of an embodiment of the invention, and, as such, is perfectly cylindrical, i.e., is not shaped so as to define any grooves or other surface or internal anomalies. No portion of anchor 432 intersects central longitudinal axis 500.

Reference is made to FIGS. 19A and 7B, which are schematic illustrations of rotating deployment element 438 in radially-expanded and radially-compressed states, respectively, in accordance with an application of the present invention. For some applications, rotating deployment element 438 is shaped so as to define at least two prongs 524A and 524B that extend in a distal direction from a proximal base 522 of the deployment element. Engagement elements 520A and 520B extend in a distal direction from prongs 524A and 524B, respectively. The engagement elements are typically male, and, for example, may together have a cross-sectional shape that is rectangular, e.g., square. Optionally, rotating deployment element 438 comprises more than two prongs and two engagement elements, e.g., three or four of each.

Rotating deployment element 438 is typically configured to assume a radially-expanded state as its resting state, as shown in FIG. 19A. In this expanded state, engagement elements 520A and 520B, as well as prongs 524A and 524B, are positioned apart from one another. In this state, the engagement elements are shaped and sized to engage tool-engaging head 462 of anchor 432, as shown, for example, in FIG. 16B.

As shown in FIG. 19B, the rotating deployment element 438 assumes a radially-compressed state, when the engagement elements and prongs are squeezed together, such as by passing through the engaging opening of tool-engaging head 462 of anchor 432, as described hereinabove with reference to FIG. 16C.

Reference is now made to FIGS. 20A and 20B, which are schematic illustrations of rotating deployment element 438 engaging tool-engaging head 462 of anchor 432, with the element 438 in locked and unlocked states, respectively, in accordance with an application of the present invention. In accordance with this application, rotating deployment element 438 comprises a locking mechanism 528, which is configured to selectively assume locked and unlocked states. When locking mechanism 528 assumes the locked state, the locking mechanism prevents disengagement of rotating deployment element 438 from the anchor which rotating deployment element 438 currently engages anchor. This locking allows deployment element 438 to proximally withdraw anchor 432 if necessary, without coming disengaged therefrom. Disengagement is thus prevented even upon withdrawal of the rotating deployment element in the proximal direction. When the locking mechanism assumes the unlocked state, the locking mechanism does not prevent disengagement of the rotating deployment element from the anchor upon withdrawal of rotating deployment element 438 in the proximal direction. The rotating deployment element thus can be disengaged and withdrawn from the anchor in a proximal direction. It is noted that even when the locking mechanism assumes the unlocked state, the rotating deployment element generally does not disengage from the anchor unless the rotating deployment element is withdrawn in the proximal direction. As mentioned above with reference to FIG. 19A, rotating deployment element 438 is typically configured to assume a radially-expanded state as its resting state. In this radially-expanded state, engagement elements 520A and 520B are positioned apart from each other, and engage tool-engaging head 462 of anchor 432.

For some applications, locking mechanism 528 comprises a pin 530. In order to cause the locking mechanism to assume the locked position, pin 530 is advanced distally between engagement elements 520A and 520B. The pin holds the engagement elements in their radially-expanded state, as described hereinabove with reference to FIG. 19A, thereby preventing the engagement elements from assuming the radially-compressed state shown in FIG. 19B and disengaging from the anchor. In the radially-expanded state, the engagement elements engage proximal engaging surface 466 of tool-engaging head 462 of anchor 432. In order to cause locking mechanism 528 to assume the unlocked state, pin 530 is withdrawn proximally from between engagement elements 520A and 520B. As a result, the engagement elements may assume the radially-compressed state shown in FIG. 19B when deployment element 438 is withdrawn in the proximal direction. In the radially-compressed state, the engagement elements do not engage the tool-engaging head of the anchor.

Providing this selective, actively-controllable engagement and release of the anchor allows rotating deployment element 438 to be used to unscrew an already-deployed anchor from the tissue, and/or to proximally withdraw an anchor, without deployment element 438 unintentionally disengaging from the anchor head. Such unscrewing or proximal withdrawal may allow an anchor to be repositioned if it is initially coupled to the tissue in an incorrect location. Rotating deployment element 438 is capable of performing this redeployment for both (a) the anchor that has been most recently deployed into the tissue, and to which the deployment element 438 is still coupled, and (b) an anchor that was previously deployed, and from which deployment element 438 has already been decoupled (and, optionally, even after another anchor has subsequently been deployed). In the latter case, deployment element 438 re-engages the anchor that is to be redeployed.

Reference is now made to FIGS. 21A-I, which are schematic illustrations of a procedure for implanting an annuloplasty ring 622 to repair a mitral valve 630, in accordance with an application of the present invention. This procedure is one exemplary procedure that can be performed using anchor deployment system 420.

Annuloplasty ring 622 is used to repair a dilated valve annulus of an atrioventricular valve, such as mitral valve 630. For some applications, the annuloplasty ring is configured to be placed only partially around the valve annulus (e.g., to assume a C-shape), and, once anchored in place, to be contracted so as to circumferentially tighten the valve annulus. The annuloplasty ring comprises a flexible sleeve 626 and a plurality of anchors 432. Anchor deployment tool 430 is advanced into a lumen of sleeve 626, and, from within the lumen, deploys the anchors through a wall of the sleeve and into cardiac tissue, thereby anchoring the sleeve around a portion of the valve annulus. For some application, annuloplasty ring 622 is implemented using techniques described in U.S. application Ser. No. 12/437,103, filed May 7, 2009, and/or U.S. application Ser. No. 12/689,635, filed Jan. 19, 2010, both of which are assigned to the assignee of the present application and are incorporated herein by reference. For some application, annuloplasty ring 622 comprises a contracting mechanism 640. The contracting mechanism comprises a rotatable structure, such as a spool, arranged such that rotation of the rotatable structure contracts the implant structure. The implant further comprises a longitudinal member, such as a wire, which is coupled to the contracting mechanism. A rotation tool is provided for rotating the rotatable structure. The tool is configured to be guided along (e.g., over, alongside, or through) the longitudinal member, to engage the rotatable structure, and to rotate the rotatable structure in response to a rotational force applied to the tool.

Figure 21A:
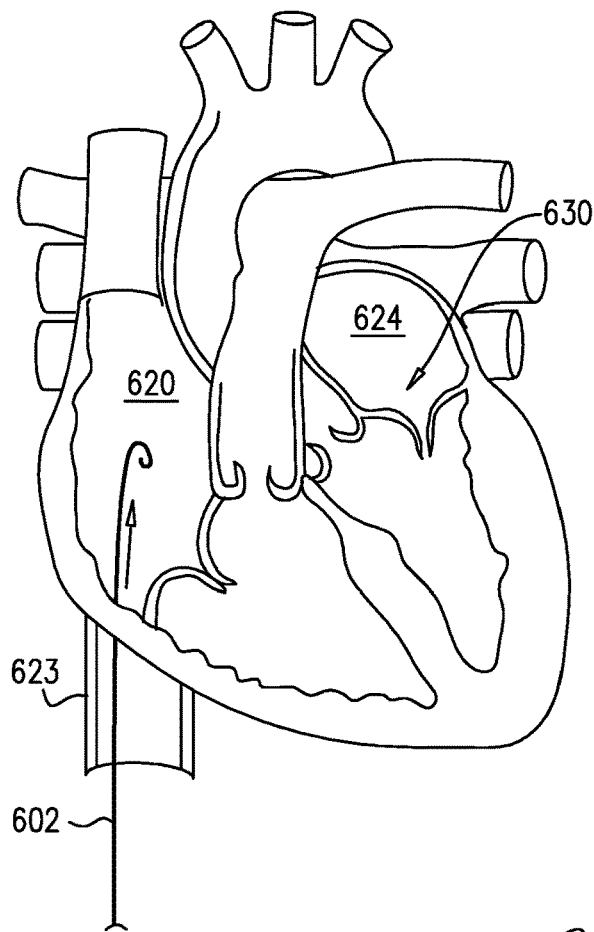

As shown in FIG. 21A, the procedure typically begins by advancing a semi-rigid guidewire 602 into a right atrium 620 of the patient. The procedure is typically performed with the aid of imaging, such as fluoroscopy, transesophageal echo, and/or echocardiography.

Figure 21B:
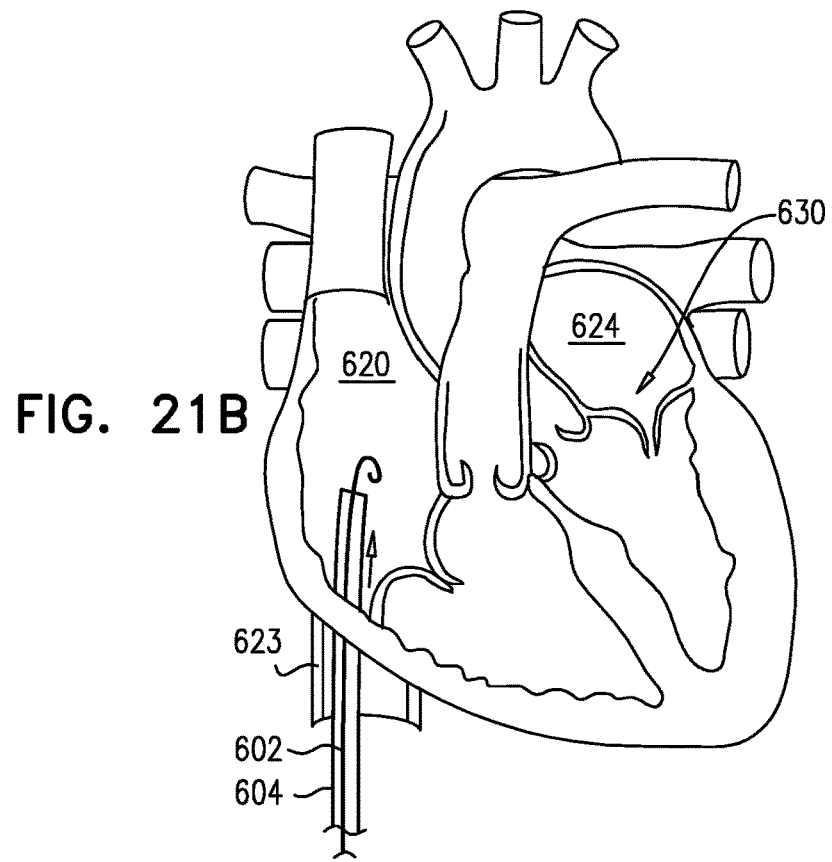

As show in FIG. 21B, guidewire 602 provides a guide for the subsequent advancement of a sheath 604 therealong and into the right atrium. Once sheath 604 has entered the right atrium, guidewire 602 is retracted from the patient's body. Sheath 604 typically comprises a 14-20 F sheath, although the size may be selected as appropriate for a given patient. Sheath 604 is advanced through vasculature into the right atrium using a suitable point of origin typically determined for a given patient. For example:

sheath 604 may be introduced into the femoral vein of the patient, through an inferior vena cava 623, into right atrium 620, and into a left atrium 624 transseptally, typically through the fossa ovalis;

sheath 604 may be introduced into the basilic vein, through the subclavian vein to the superior vena cava, into right atrium 620, and into left atrium 624 transseptally, typically through the fossa ovalis; or sheath 604 may be introduced into the external jugular vein, through the subclavian vein to the superior vena cava, into right atrium 620, and into left atrium 624 transseptally, typically through the fossa ovalis.

For some applications of the present invention, sheath 604 is advanced through inferior vena cava 623 of the patient (as shown) and into right atrium 620 using a suitable point of origin typically determined for a given patient.

Figure 21C:
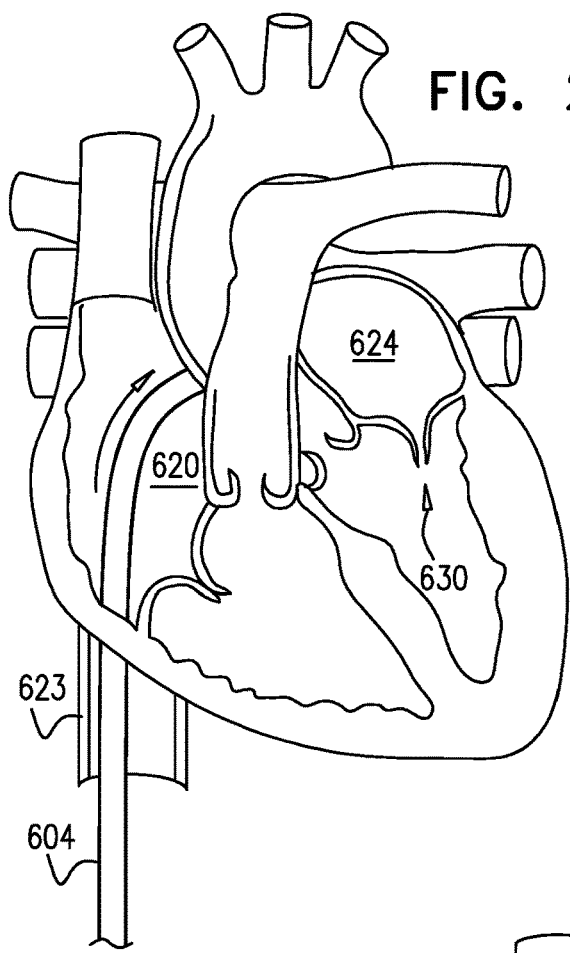

Sheath 604 is advanced distally until the sheath reaches the interatrial septum, and guidewire 602 is withdrawn, as shown in FIG. 21C.

Figure 21D:
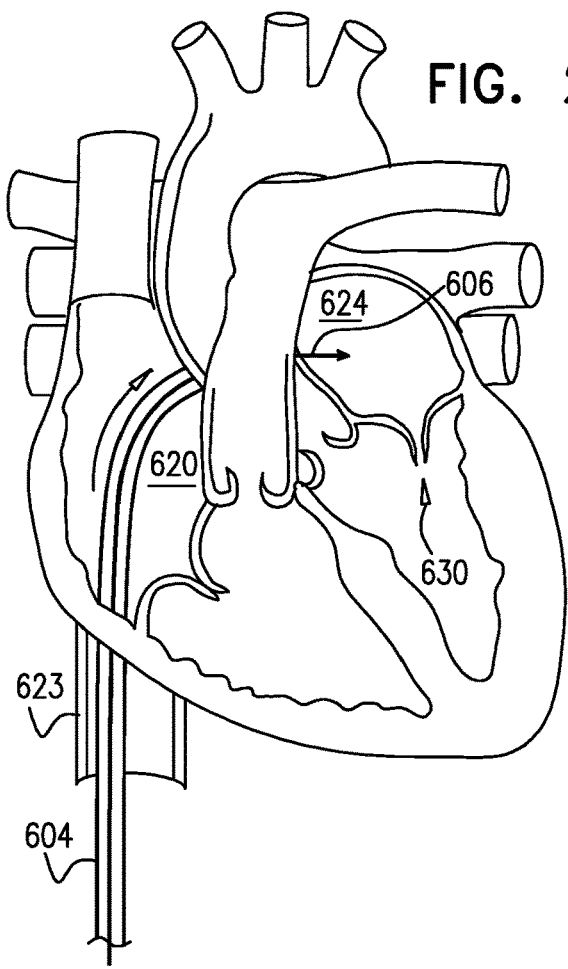

As shown in FIG. 21D, a resilient needle 606 and a dilator (not shown) are advanced through sheath 604 and into the heart. In order to advance sheath 604 transseptally into left atrium 624, the dilator is advanced to the septum, and needle 606 is pushed from within the dilator and is allowed to puncture the septum to create an opening that facilitates passage of the dilator and subsequently sheath 604 therethrough and into left atrium 624. The dilator is passed through the hole in the septum created by the needle. Typically, the dilator is shaped to define a hollow shaft for passage along needle 606, and the hollow shaft is shaped to define a tapered distal end. This tapered distal end is first advanced through the hole created by needle 606. The hole is enlarged when the gradually increasing diameter of the distal end of the dilator is pushed through the hole in the septum.

Figure 21E:
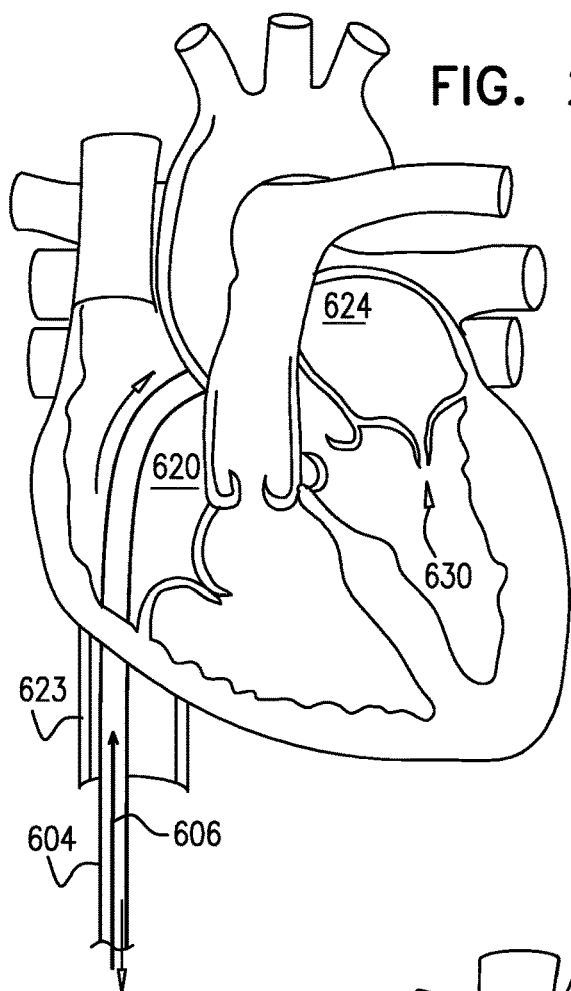

The advancement of sheath 604 through the septum and into the left atrium is followed by the extraction of the dilator and needle 606 from within sheath 604, as shown in FIG. 21E.

Figure 21F:
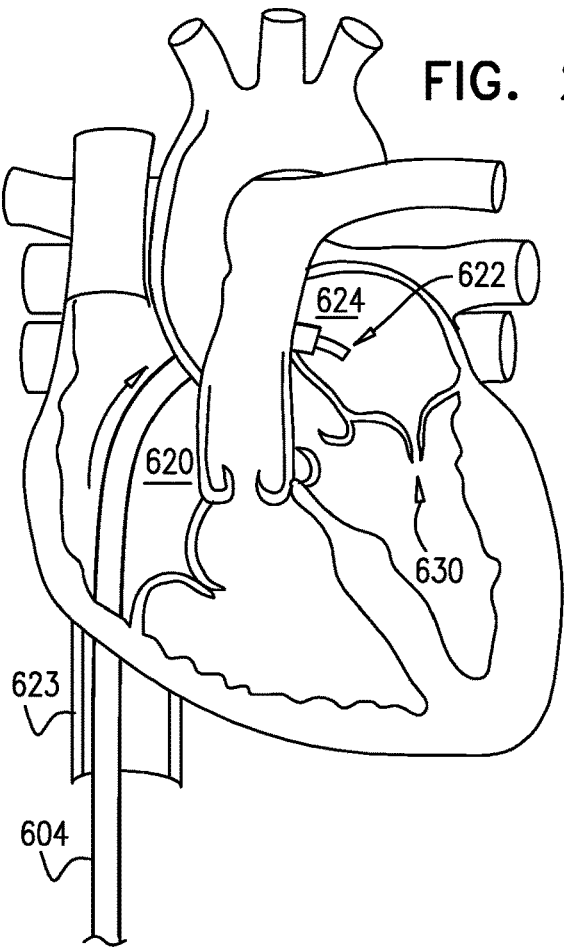

As shown in FIG. 21F, annuloplasty ring 622 (with anchor deployment tool 430 therein) is advanced through sheath 604 into left atrium 624.

Figure 21G:
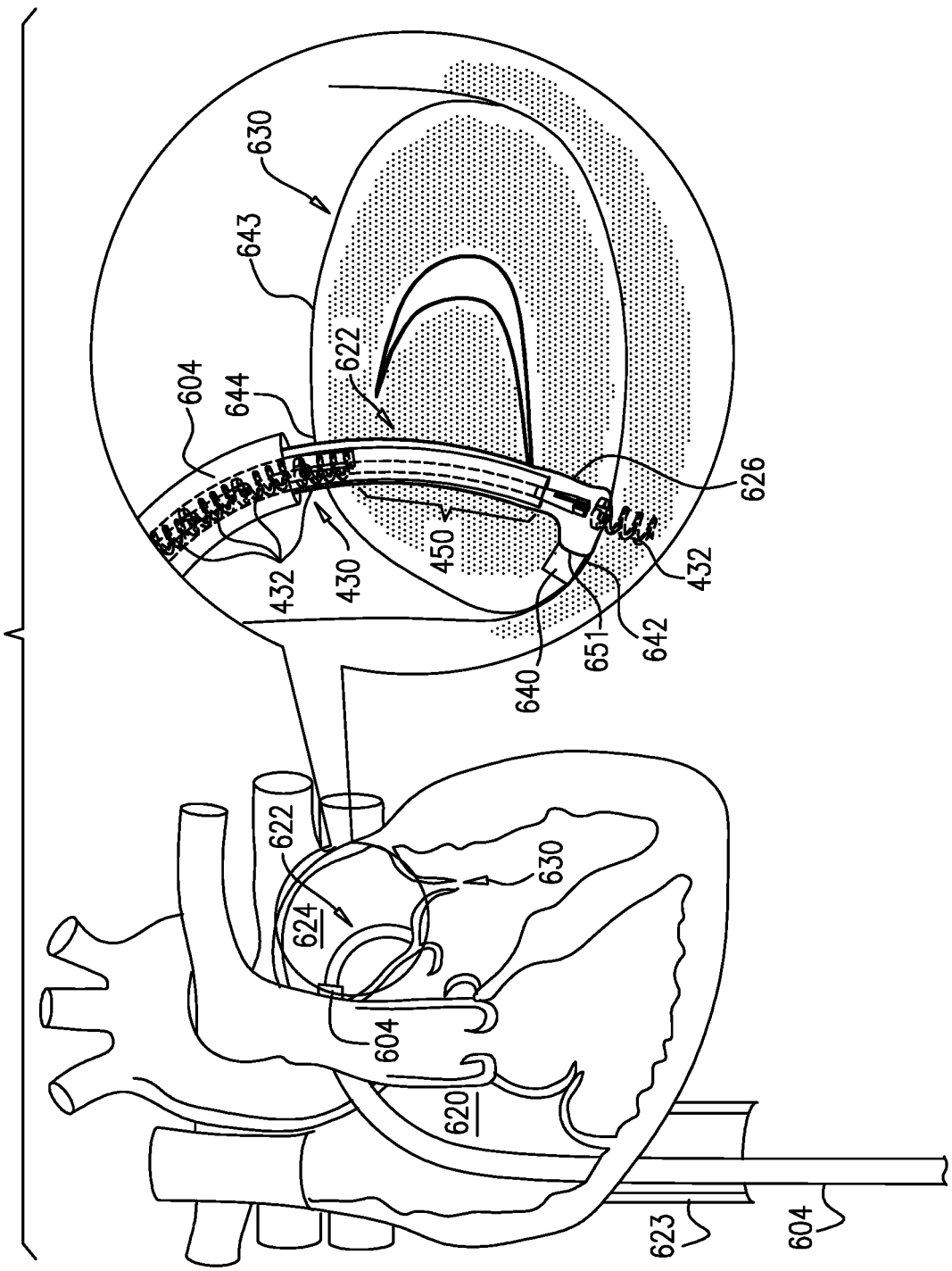

As shown in FIG. 21G, a distal end 651 of sleeve 626 is positioned in a vicinity of a left fibrous trigone 642 of an annulus 643 of mitral valve 630. (It is noted that for clarity of illustration, distal end 651 of sleeve 626 is shown schematically in the cross-sectional view of the heart, although left trigone 642 is in reality not located in the shown cross-sectional plane, but rather out of the page closer to the viewer.) Alternatively, the tip is positioned in a vicinity of a right fibrous trigone 644 of the mitral valve (configuration not shown). Further alternatively, the distal tip of the sleeve is not positioned in the vicinity of either of the trigones, but is instead positioned elsewhere in a vicinity of the mitral valve, such as in a vicinity of the anterior or posterior commissure. The steering functionality of anchor manipulation area 450 typically allows the area near the distal end of the deployment tool to be positioned with six degrees of freedom. Once positioned at the desired site near the selected trigone, deployment tool 430 deploys a first anchor 432 through the wall of sleeve 626 into cardiac tissue near the trigone, using the techniques described hereinabove with reference to FIGS. 16A-C.

As shown in FIG. 21H, deployment tool 430 is repositioned along annulus 643 to another site selected for deployment of a second anchor 432. Typically, the first anchor is deployed most distally in the sleeve (generally at or within a few millimeters of the distal tip of the sleeve and each subsequent anchor is deployed more proximally, such that the sleeve is gradually pulled off (i.e., withdrawn from) the deployment tool in a distal direction during the anchoring procedure. The already-deployed first anchor 432 holds the anchored end of sleeve 626 in place, so that the sleeve is drawn from the site of the first anchor towards the site of the second anchor. Typically, as the sleeve is pulled off (i.e., withdrawn from) the deployment tool, the deployment tool is moved generally laterally along the cardiac tissue, as shown in FIG. 21H. Deployment tool 430 deploys the second anchor through the wall of the sleeve into cardiac tissue at the second site. Depending on the tension applied between the first and second anchor sites, the portion of sleeve 626 therebetween may remain tubular in shape, or may become flattened, which may help reduce any interference of the ring with blood flow.

The techniques described hereinabove with reference to FIG. 16D, followed again by those described with reference to FIGS. 16A-C, are used to provide and deploy the second and subsequent anchors one at a time at the selected sites, respectively.

Figure 21I:
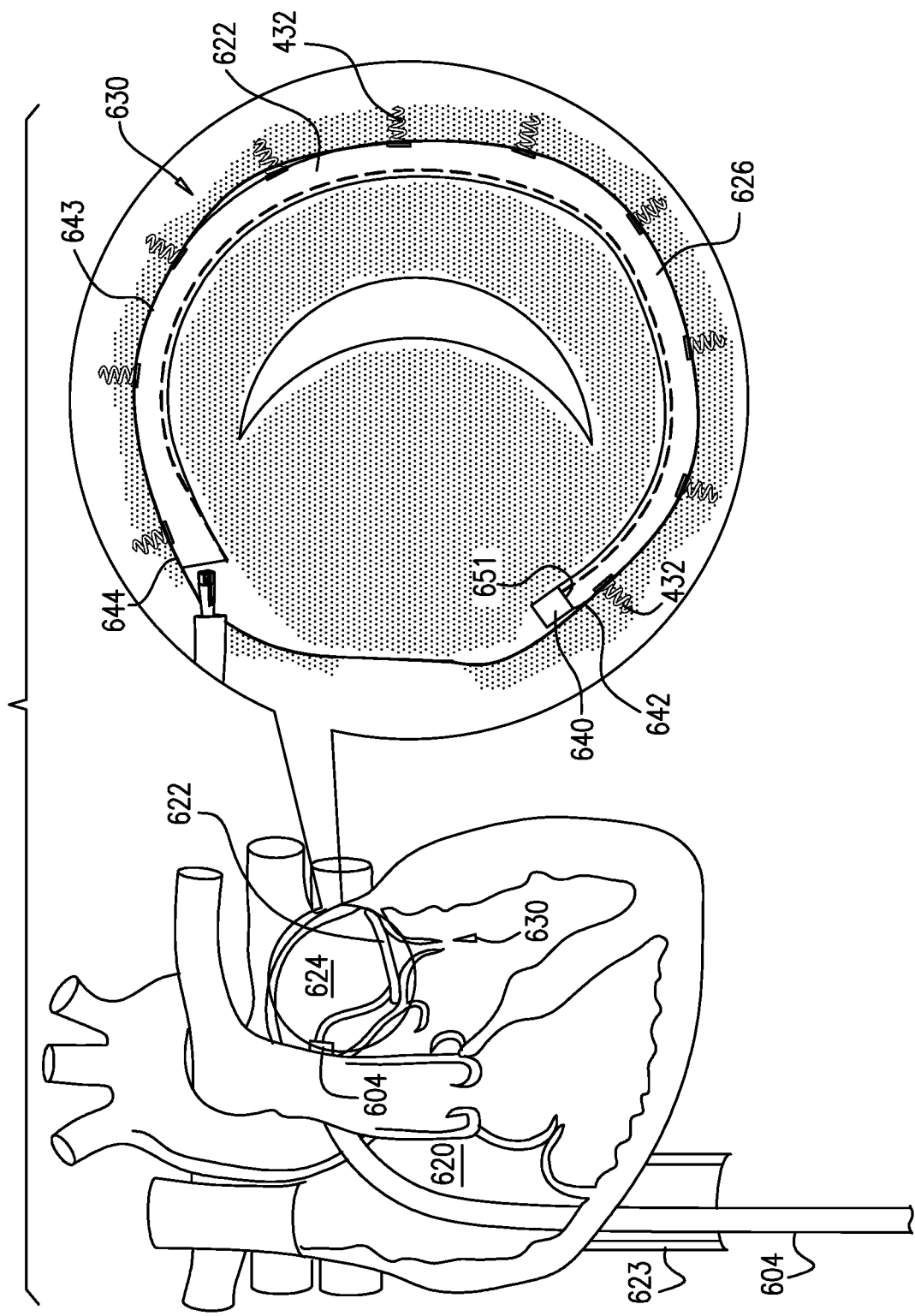

As shown in FIG. 21I, deployment tool 430 is repositioned along the annulus to additional sites, at which respective anchors are deployed, until the last anchor is deployed in a vicinity of right fibrous trigone 644 (or left fibrous trigone 642 if the anchoring began at the right trigone). Alternatively, the last anchor is not deployed in the vicinity of a trigone, but is instead deployed elsewhere in a vicinity of the mitral valve, such as in a vicinity of the anterior or posterior commissure. A rotation tool or anchor driver is used to rotate the spool of contracting mechanism 640, in order to tighten ring 622.

Alternatively, annuloplasty ring 622 is implanted by right or left thoracotomy, mutatis mutandis.

For some applications of the present invention, annuloplasty ring 622 is used to treat an atrioventricular valve other than the mitral valve, i.e., the tricuspid valve. For these applications, ring 622 and other components of system 420 described hereinabove as being placed in the left atrium are instead placed in the right atrium. Although annuloplasty ring 622 is described hereinabove as being placed in an atrium, for some application the ring is instead placed in either the left or right ventricle.

In an application of the present invention, anchor deployment system 420 is used in combination with mitral valve repair system 400, described with reference to FIGS. 17A-F, 18A-B, 19A-E, and 20A-B of International Application PCT/IL2009/000593, filed Jun. 15, 2009, which published as PCT Publication WO 10/004546, and which is incorporated herein by reference. Instead of passing anchors through the lumen of the catheter from a site outside the body of the patient, as described with reference to FIG. 20B, the anchors are stored in anchor storage area 440 of anchor deployment tool 430.

For some applications, techniques described hereinabove with reference to FIGS. 13A-21I are practiced in combination with techniques described in one or more of the references cited in the Background section of the present patent application.

Additionally, the scope of the present invention described hereinabove with reference to FIGS. 13A-21I includes embodiments described in the following applications, which are incorporated herein by reference. In an embodiment, techniques and apparatus described in one or more of the following applications are combined with techniques and apparatus described hereinabove with reference to FIGS. 13A-21I:

PCT Publication WO 06/097931 to Gross et al., entitled, "Mitral Valve treatment techniques," filed Mar. 15, 2006;

U.S. Provisional Patent Application 60/873,075 to Gross et al, entitled, "Mitral valve closure techniques," filed Dec. 5, 2006;

U.S. Provisional Patent Application 60/902,146 to Gross et al., entitled, "Mitral valve closure techniques," filed Feb. 16, 2007;

U.S. Provisional Patent Application 61/001,013 to Gross et al., entitled, "Segmented ring placement," filed Oct. 29, 2007;

PCT Patent Application PCT/IL07/001503 to Gross et al., entitled, "Segmented ring placement," filed Dec. 5, 2007, which published as PCT Publication WO 2008/068756;

U.S. patent application Ser. No. 11/950,930 to Gross et al., entitled, "Segmented ring placement," filed Dec. 5, 2007, which published as US Patent Application Publication 2008/0262609;

U.S. Provisional Patent Application 61/132,295 to Gross et al., entitled, "Annuloplasty devices and methods of delivery therefor," filed Jun. 16, 2008;

U.S. patent application Ser. No. 12/341,960 to Cabiri, entitled, "Adjustable partial annuloplasty ring and mechanism therefor," filed Dec. 22, 2008, which issued as U.S. Pat. No. 8,241,351;

U.S. Provisional Patent Application 61/207,908 to Miller et al., entitled, "Actively-engageable movement-restriction mechanism for use with an annuloplasty structure," filed Feb. 17, 2009;

U.S. patent application Ser. No. 12/435,291 to Maisano et al., entitled, "Adjustable repair chords and spool mechanism therefor," filed May 4, 2009, which issued as U.S. Pat. No. 8,147,542;

U.S. patent application Ser. No. 12/437,103 to Zipory et al., entitled, "Annuloplasty ring with intra-ring anchoring," filed May 7, 2009, which issued as U.S. Pat. No. 8,715,342;

PCT Patent Application PCT/IL2009/000593 to Gross et al., entitled, "Annuloplasty devices and methods of delivery therefor," filed Jun. 15, 2009, which published as PCT Publication WO 10/004546;

U.S. patent application Ser. No. 12/548,991 to Maisano et al., entitled, "Implantation of repair chords in the heart," filed Aug. 27, 2009, which issued as U.S. Pat. No. 8,808,368;

U.S. patent application Ser. No. 12/608,316 to Miller et al., entitled, "Tissue anchor for annuloplasty ring," filed Oct. 29, 2009, which issued as U.S. Pat. No. 8,277,502;

U.S. Provisional Patent Application 61/265,936 to Miller et al., entitled, "Delivery tool for implantation of spool assembly coupled to a helical anchor," filed Dec. 2, 2009;

PCT Patent Application PCT/IL2009/001209 to Cabiri et al., entitled, "Adjustable annuloplasty devices and mechanisms therefor," filed Dec. 22, 2009, which published as PCT Publication WO 2010/073246;

U.S. patent application Ser. No. 12/689,635 to Zipory et al., entitled, "Over-wire rotation tool," filed Jan. 19, 2010, which issued as U.S. Pat. No. 8,545,553;

U.S. patent application Ser. No. 12/689,693 to Hammer et al., entitled, "Deployment techniques for annuloplasty ring," filed Jan. 19, 2010, which issued as U.S. Pat. No. 8,911,494;

U.S. patent application Ser. No. 12/706,868 to Miller et al., entitled, "Actively-engageable movement-restriction mechanism for use with an annuloplasty structure," filed Feb. 17, 2010, which published as US Patent Application Publication 2010/0211166;

PCT Patent Application PCT/IL2010/000357 to Maisano et al., entitled, "Implantation of repair chords in the heart," filed May 4, 2010, which published as PCT Publication WO 2010/128502;

PCT Patent Application PCT/IL2010/000358 to Zipory et al., entitled, "Deployment techniques for annuloplasty ring and over-wire rotation tool," filed May 4, 2010, which published as PCT Publication WO 10/128503; and/or U.S. application Ser. No. 12/785,717 to Miller et al., entitled, "Adjustable artificial chordeae tendineae with suture loops," filed May 24, 2010, which issued as U.S. Pat. No. 8,790,394.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

What is claimed is:

1. A system comprising:
an implantable device; and
an anchor deployment tool, which comprises:
(a) a flexible tube including a distal anchor manipulation portion that is steerable; and
(b) a rotating deployment element, which is positionable within the flexible tube, and is configured to, while the distal anchor manipulation portion is proximate the implantable device:
(i) engage one or more tissue anchors in the flexible tube,
(ii) advance the one or more tissue anchors in a distal direction to the distal anchor manipulation portion, and
(iii) anchor the implantable device to tissue of a subject by deploying each of the tissue anchors through the implantable device and into the tissue,
wherein the anchor deployment tool is configured such that one or more tissue anchors are advanced by the rotating deployment element; and
wherein the rotating deployment element is configured to assume a state in which the rotating deployment element is passable through one or more of the tissue anchors without engaging them.

2. The apparatus according to claim 1, wherein the distal anchor manipulation portion is flexible.

3. The apparatus according to claim 1, wherein the anchor deployment tool comprises one or more steering wires, which are arranged such that pulling and releasing of the steering wires cause deflection of a distal end of the anchor deployment tool, thereby providing steering functionality to the distal anchor manipulation portion.

4. The apparatus according to claim 1, wherein the rotating deployment element is configured to assume the state when withdrawn in a proximal direction within the flexible tube.

5. The apparatus according to claim 1, wherein the state is a radially-compressed state, and wherein the rotating deployment element is configured to assume a radially-expanded state when engaging each of the one or more tissue anchors.

6. The apparatus according to claim 1, wherein the anchor deployment tool is configured to deploy each of the one or more tissue anchors into the tissue in a direction parallel to a central longitudinal axis of the tube through the distal tube end, and parallel to a central longitudinal axis of the tissue anchor.

7. The apparatus according to claim 1, wherein the rotating deployment element is configured such that it can unscrew an already-deployed tissue anchor from the tissue, withdraw the tissue anchor in a proximal direction, and subsequently redeploy the tissue anchor into the tissue.

8. The apparatus according to claim 1, wherein the implantable device is an annuloplasty device comprising a sleeve.

9. The apparatus according to claim 1, wherein the rotating deployment element is configured to deploy each of the one or more tissue anchors through the distal tube end and into the tissue by rotating only the tissue anchor directly engaged by the rotating deployment element, without rotating the tissue anchors stored in an anchor storage area.

10. The apparatus according to claim 1, wherein the length of the distal anchor manipulation portion is at least 5 cm.

11. The apparatus according to claim 1, wherein the anchor deployment tool is usable to deploy at least 6 tissue anchors.

12. A system comprising:
an anchor deployment tool, which comprises:
(a) a flexible tube having an anchor holding area in which tissue anchors are held before deployment, and a distal anchor manipulation portion is steerable; and
(b) a deployment element positionable within the flexible tube and configured to:
(i) engage the tissue anchors in the anchor storage area,
(ii) advance one or more of the tissue anchors in a distal direction into the distal anchor manipulation portion, and
(iii) anchor the one or more tissue anchors into the tissue,
wherein the anchor deployment tool is configured such that one anchor is advanced at a time by the deployment element; and
wherein the deployment element is configured to assume a state in which the deployment element is passable through one or more of the tissue anchors without engaging them.

13. The apparatus according to claim 12, wherein the distal anchor manipulation portion is flexible.

14. The apparatus according to claim 12, wherein the anchor deployment tool comprises one or more steering wires, which are arranged such that pulling and releasing of the steering wires cause deflection of the distal anchor manipulation portion, thereby providing steering functionality to the distal anchor manipulation portion.

15. The apparatus according to claim 12, wherein the deployment element is configured to assume the state when withdrawn in a proximal direction within the tube.

16. The apparatus according to claim 12, wherein the anchor deployment tool is configured to deploy each of the tissue anchors into the tissue in a direction parallel to a central longitudinal axis of the tube through the distal tube end, and parallel to a central longitudinal axis of the tissue anchor.

17. The apparatus according to claim 12, comprising an annuloplasty device having a sleeve.

18. A system comprising:
an implantable device; and
an anchor deployment tool, which comprises:
(a) a flexible tube including a distal anchor manipulation portion that is flexible and steerable; and
(b) a deployment element, which is positionable within the flexible tube, and is configured to, while the distal anchor manipulation portion is proximate the implantable device:
(i) engage one or more tissue anchors in the flexible tube,
(ii) advance the one or more tissue anchors in a distal direction to the distal anchor manipulation portion, and
(iii) anchor the implantable device to tissue of a subject by deploying each of the tissue anchors through the implantable device and into the tissue,
wherein the anchor deployment tool is configured such that one or more tissue anchors are advanced by the deployment element, and wherein the deployment element is configured such that it can unscrew a deployed tissue anchor from the tissue, withdraw the deployed tissue anchor in a proximal direction, and subsequently redeploy the tissue anchor into the tissue; and
wherein the deployment element is configured to assume a state in which the deployment element is passable through one or more of the tissue anchors without engaging them.

* * * * *

UNITED STATES PATENT AND TRADEMARK OFFICE
CERTIFICATE OF CORRECTION

PATENT NO.       : 10,856,987 B2                            Page 1 of 1
APPLICATION NO.  : 15/948140
DATED            : December 8, 2020
INVENTOR(S)      : Oz Cabiri et al.

It is certified that error appears in the above-identified patent and that said Letters Patent is hereby corrected as shown below:

On the Title Page

Item (63), Related U.S. Application Data:
Page 2, Column 1, Line 7, delete the word "which" and insert in its place -- and application No. 13/749,153, filed on Jan. 24, 2013, now Pat. No. 9,119,719 --

Signed and Sealed this
Eighteenth Day of May, 2021

Drew Hirshfeld
*Performing the Functions and Duties of the
Under Secretary of Commerce for Intellectual Property and
Director of the United States Patent and Trademark Office*